(12) United States Patent
Hanney et al.

(10) Patent No.: US 9,102,673 B2
(45) Date of Patent: Aug. 11, 2015

(54) SUBSTITUTED PYRROLO[3,2-C]PYRIDINES AS TRKA KINASE INHIBITORS

(75) Inventors: Barbara Hanney, Pennsburg, PA (US); Peter Manley, Harleysville, PA (US); Michael T. Rudd, Collegeville, PA (US); John M. Sanders, Collegeville, PA (US); Shawn J. Stachel, Perkasie, PA (US); Darrell Henze, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 20 days.

(21) Appl. No.: 14/131,861

(22) PCT Filed: Jul. 6, 2012

(86) PCT No.: PCT/US2012/045638
§ 371 (c)(1),
(2), (4) Date: Jan. 9, 2014

(87) PCT Pub. No.: WO2013/009582
PCT Pub. Date: Jan. 17, 2013

(65) Prior Publication Data
US 2014/0155413 A1    Jun. 5, 2014

Related U.S. Application Data

(60) Provisional application No. 61/506,735, filed on Jul. 12, 2011.

(51) Int. Cl.
| | |
|---|---|
| *A61K 31/437* | (2006.01) |
| *C07D 471/04* | (2006.01) |
| *C07D 401/04* | (2006.01) |
| *C07D 403/04* | (2006.01) |
| *C07D 405/04* | (2006.01) |
| *C07D 417/04* | (2006.01) |
| *C07D 487/04* | (2006.01) |

(52) U.S. Cl.
CPC ............ *C07D 471/04* (2013.01); *C07D 401/04* (2013.01); *C07D 403/04* (2013.01); *C07D 405/04* (2013.01); *C07D 417/04* (2013.01); *C07D 487/04* (2013.01)

(58) Field of Classification Search
CPC .............................. A61K 31/437; C07D 471/04
USPC ........... 514/300; 544/333, 405; 546/148, 152, 546/208, 276.7; 548/131, 202, 235, 373.1, 548/518; 549/356, 429
See application file for complete search history.

(56) References Cited

U.S. PATENT DOCUMENTS

| | | | |
|---|---|---|---|
| 4,831,144 A * | 5/1989 | Dormoy et al. | ............... 546/113 |
| 6,029,114 A | 2/2000 | Shamovsky et al. | |
| 6,281,227 B1 * | 8/2001 | Choi-Sledeski et al. | ...... 514/307 |
| 6,441,004 B1 | 8/2002 | Faull et al. | |
| 2008/0045496 A1 | 2/2008 | Fink et al. | |
| 2009/0137624 A1 | 5/2009 | Lamb et al. | |

FOREIGN PATENT DOCUMENTS

| | | |
|---|---|---|
| EP | 1181318 | 5/2000 |
| WO | WO01/078698 | 10/2001 |
| WO | WO0178698 | 10/2001 |
| WO | WO2004/005184 | 7/2004 |
| WO | WO200405184 | 7/2004 |
| WO | WO2004/096122 | 11/2004 |
| WO | WO2004096122 | 11/2004 |
| WO | WO2005/019266 | 3/2005 |
| WO | WO2005019266 | 3/2005 |
| WO | WO2005/061540 | 7/2005 |
| WO | WO2005061540 | 7/2005 |
| WO | WO2005/110994 | 11/2005 |
| WO | WO2005110994 | 11/2005 |
| WO | WO2006/012135 | 2/2006 |
| WO | WO2006/137106 | 6/2006 |

(Continued)

OTHER PUBLICATIONS

Bardelli et al., Mutational Analysis of the Tryosine Kinome in Colorectal Cancers, Science, May 9, 2003, pp. 949, 300.

(Continued)

*Primary Examiner* — Douglas M Willis
(74) *Attorney, Agent, or Firm* — Sylvia A. Ayler; John C. Todaro

(57) ABSTRACT

The present invention is directed to compounds of formula I and Ia: which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

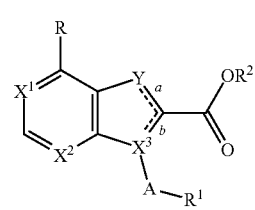

and

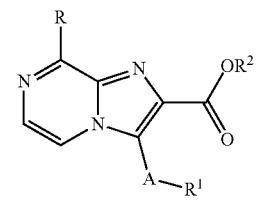

14 Claims, No Drawings

(56) References Cited

FOREIGN PATENT DOCUMENTS

| WO | WO2006137106 | 6/2006 |
|---|---|---|
| WO | WO2006/013673 | 7/2006 |
| WO | WO07013673 | 7/2006 |
| WO | WO2006/087538 | 8/2006 |
| WO | WO2006087538 | 8/2006 |
| WO | WO2006/115452 | 11/2006 |
| WO | WO2006/123113 | 11/2006 |
| WO | WO2006115452 | 11/2006 |
| WO | WO2006123113 | 11/2006 |
| WO | WO2006/131952 | 12/2006 |
| WO | WO2006131952 | 12/2006 |
| WO | WO2007/025540 | 3/2007 |
| WO | WO2007025540 | 3/2007 |
| WO | WO2007/068621 | 6/2007 |
| WO | WO2008/052734 | 5/2008 |
| WO | WO2008052734 | 5/2008 |
| WO | WO2008/131000 | 10/2008 |
| WO | WO2010/033941 | 3/2010 |
| WO | WO2010033941 | 3/2010 |
| WO | WO2010/077680 | 7/2010 |
| WO | WO2010077680 | 7/2010 |

OTHER PUBLICATIONS

Raychaudhuri et al., K252a, a High-Affinity Nerve Growth Factor Receptor Blocker,, J. of Investigative Dermatology, 2004, pp. 812-819, 122.

Zahn et al., Effect of Blockade of Nerve Growth Factor and Tumor Necrosis Factor on Pain Behaviors After Plantar Incision, J. Pain, 2004, pp. 157-163, 5.

Chaulet et al., Desulfonylation of Indoles and 7-Azaindoles Using Sodium Tert-Butoxide, Synlett, 2010, pp. 1481-1484, 2010.

Sall et al., Use of Conformatoionally Restricted Benzamidines as Arginine Surrogates in the Desing of Platelet GPIIB-IIIA Receptor Antagonists, J. Medicinal Chemistry, 1997, pp. 2843-2857, 40.

Verniest et al., Heteroaryl Cross-Coupling as an Entry Toward the Synthesis of Lavendamycin Analogues: A Model Study, J. Of Organic Chemistry, 2010, pp. 424-433, 75.

Assumi et al., Expression of Neurotrophins and Their Receptors (TRK) During Fracture Healing, Bone, 2000, pp. 625-633, 26.

Bardelli et al., Mutational Analysis of the Tryosine Kinome in Colorectal Cancers, Science, May 9, 2003, pp. 949-300.

Brodeur et al., Neuroblastoma: Biological Insights into a Clincal Enigma, Nat. Rev Cancer, 2003, pp. 203-216, 3.

Dang et al., Expression of Nerve Growth Factor Receptors is Correlated with Progression and Prognosis of Human Pancreatic Cancer, J. Of Gastroenterology and Hepatology, 2006, pp. 850-858, 21.

Delafoy et al., Role of Nerve Growth Factor in the Trinitrobenzene Sulfonic Acid-Induced Colonic Hypersensitivity, Pain, 2003, pp. 489-497, 105.

Di Mola, Nerve Growth Factor and TRK HIHG Affinity Receptor (TRkA) Gene Expression in Inflammatory Bowel Disease, Gut, 2000, pp. 670-678, 46.

Dionne et al., Cell cycle-independent death of prostate adenocarcinoma is Induced by the TRK Tyrosine Kinase Inhibitor CEP-751 (KT6587), Clinical Cancer Research, 1998, pp. 1887-1898, 4.

Dou et al., Increased nerve growth factor and its receptors in atopic dermatitis:, Archives of Dermatological Research, 2006, pp. 31-37, 298.

Freund-Michel et al., The Nerve Growth Factor and Its Receptors in Airway Inflammatory Diseases, Pharmacology & Thereapeutics, 2008, pp. 52-76, 117.

Hu et al., Decrease in Bladder Overactivity With REN1820 in Rats, J. Of Urology, 2005, pp. 1016-1021, 173.

Iannone, Increased Expression of Nerve Growth Factoer (NGF) and high Affinity NGF Receptor (p140 TrkA) in Human Osteoarthritic Chondrocytes, Rheumatology, 2002, pp. 1413-1418, 4.

Jaggar et al., Inflammation of the Rat Urinary Bladder is associated with a Referred Thermal Hyperalgesia Which is Nerve Growth Factor Dependent, Br. J. Anaesth., 1999, pp. 442-448, 83.

Kruettgen et al., The Dark Side of the NGF Family: Neurotrophin in Neoplasia, Brain Pathology, 2006, pp. 304-310, 16.

Lamb et al., Nerve Growth Factor and Gastric Hyperalgesia in the Rat, Neurogastroenterol Motil., 2003, pp. 355-361, 15.

Ma et al., The Progressive Tactile Hyperalgesia Induced by Peripheral Inflammation is Nerve Growth Factor Dependent, Neuroreport, 1997, pp. 807-810, 8.

Marchetti et al., Frequent Mutations in the Neuroptrophic Trrosine Receptor Kinase Gene Family in Large Cell Neuroendocrine Carcinioma of the Lung, Rapid Communication, 2008, pp. 609-616, 29.

McMahon et al., The Biologgical Effects of Endogenous Nerve Growth Factor on Adult Sensory Neurons Revealed by a trkA-IgG Fusion Molecule, Nature Medicine, 1995, pp. 774-780, 1.

Raychaudhuri et al., K252a, a High-Affinity Nerve Growth Factor Receptor Blocker J. Of Investigative Dermatology, 2004, pp. 812-819, 122.

Shelton et al., Nerve growth factor mediates hyperalgesia and cachexia, Pain, 2005, pp. 8-16, 116.

Sohrabji et al., Estrogen—BDNF interactions: Implications, Frontiers in Neuroendocrinology, 2006, pp. 404-414, 27.

Tripathy et al., TrkA kinase inhibitors from a library of modified and isosteric, Bioganic & Medicinal Chemistry Letters, 2008, pp. 3551-3555, 18.

Undevia et al., Phase I Clinical Trial of CEP-2563 Dihydrochloride, A Receptor Tyrosine Kinase Inhibitor, in Patients with Refractory Solid Tumors, Investigational New Drugs, 2003, pp. 449-458, 22.

Wang et al., Trk Kinase Inhibitors as New Treatments for Cancer and Pain, Expert Opinion, 2009, pp. 305-319, 19 (3).

Woolf, Nerve Growth Factor Contributes to the Generation of Inflammatory Sensory Hypersenstivity, Neuroscience, 1994, pp. 327-331, 62.

Zhan et al., Effect of Blockade of Nerve Growth Factor and Tumor Necrosis Factor on Pain Behaviors After Plantar Incision, J. Pain, 2004, pp. 157-163, 5.

Zhu et al., Nerve Growth Factor Expression Correlation with Perineural Invasion and Pain in Human Pancreatic Cancer, J. Of Clinicl Oncology, 1999, pp. 2419-2428, 17.

\* cited by examiner

SUBSTITUTED PYRROLO[3,2-C]PYRIDINES AS TRKA KINASE INHIBITORS

CROSS REFERENCE TO RELATED APPLICATIONS

This application is a 371 of International Application No. PCT/US2012/045638 filed on Jul. 6, 2012, which claims the benefit under 35 U.S.C. 119(e) of U.S. Provisional Application No 61/506,735, filed Jul. 12, 2011.

FIELD OF THE INVENTION

The invention is directed to a class of substituted pyridotriazole and benztriazole compounds, their salts, pharmaceutical compositions comprising them and their use in therapy of the human body. In particular, the invention is directed to a class of substituted pyridotriazole and benztriazole compounds, which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

Trks are high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members, TrkA, TrkB and TrkC, that bind to and mediate the signal transduction derived from the Neurotrophins. NGF activates TrkA, BDNF and NT-4/5 activate TrkB and NT3 activates TrkC.

Inhibitors of the Trk/neurotrophin pathway have been demonstrated to be highly effective in numerous pre-clinical animal models of pain. Antagonistic NGF and TrkA antibodies have been shown to be efficacious in inflammatory and neuropathic pain animal models and in human clinical trials. See Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motu.* 15, 355-361; and Jaggar, S. I. et al. (199) *Br. J. Anaesth.* 83, 442-448. Through gene disruption studies in mice the Trka-NGF interaction was found to be required for the survival of certain peripheral neuron populations involved in mediating pain signaling in the case of pancreatic cancer—an increase in the expression of TrkA was shown to correlate with an increase level of pain signaling (Zhu et al., *Journal of Clinical oncology*, 17:2419-2428 (1999)). Increased expression of NGF and TrkA was also observed in human osteoarthritis chondrocytes (Iarmone et al, *Rheumatology* 41:1413-1418 (2002)). In particular, anti-TrkA antibodies and anti-NGF antibodies have been demonstrated to be effective analgesics in in vivo models of inflammatory and neuropathic pain. See WO2006/131952, WO2005/061540, EP1181318 and WO01/78698, WO2004/058184 and WO2005/019266, respectively. See also WO2004/096122 and WO2006/137106 which describe the use of an anti-TrkA antibody in combination with an opioid analgesic for the treatment or prevention of pain.

Trk inhibitors that can induce apotosis of proliferating osteoblast may be useful in treating diseases related to an imbalance of the regulation of bone remodeling, such as osteoporosis, rheumatoid arthritis and bone metastases. The expression of TrkA and TrkC receptors in the bone forming area in mouse models of bone fracture and localization of NGF in almost all bone forming cells have been observed (K. Asaumi, et al., Bone (2000) 26(6) 625-633). See also Exper Opin. Ther. Patents (2009) 19(3)), WO2006/115452 and WO2006/087538, WO6123113, WO10033941, WO10077680, WO2005110994, *Investigational New Drugs* (2004), 22, 449-458 and R. Tripathy, et al., Bioorganic & Medicinal Chem. Ltrs., 2008, 18, 3551-3555. The association between overexpression, activation, amplification and/or mutation of Trks and several cancers as seen with studies conducted on neuroblastoma (Brodeur, G. M., Nat. Rev. Cancer 2003, 3, 203-216), ovarian cancer (Kruettgen et al., *Brain Pathology* 2006, 16: 304-310), prostate cancer (Dionne et al., Clin. Cancer Res. 1998, 4(8): 1887-1898), pancreatic cancer (Dang et al., *J of Gastroenterology and Hepatology* 2006, 21(5): 850-858), large cell neuroendocrine tumors (Marchetti et al., *Human Mutation* 2008, 29(5), 609-616, and colorectal cancer (Bardelli, A., *Science* 2003, 300, 949) supports the reasoning that therapeutic implications of an effective Trk inhibitor may extend far beyond pain therapy. See also WO07013673, WO07025540 and WO08052734.

Also promising is the utility of Trk inhibitors in the treatment of inflammatory lung diseases such as asthma (Freund-Michel, V; et al., *Pharmacology & Therapeutics* (2008), 117 (1), 52-76), interstitial cystitis (Hu Vivian Y; et. al., *J of Urology* (2005, 173(3), 1016-21), inflammatory bowel disease including ulcerative colitis and Chron's disease (Di Mola, F. F., et al., *Gut* (2000), 46(5), 670-678 and inflammatory skin diseases such as atopic dermatitis (Dou, Y. C., et. Al., *Archives of Dermatological Research* (2006), 298(1), 31-37, eczema and psoriasis (Raychaudhuri, S. P. et. al., *J of Investigative Dermatology* (2004), 122(3), 812-819).

Modulation of the neurotrophin/Trk pathway also has been shown to have an effect in the etiology of neurodegenerative diseases including multiple sclerosis, Parkinson's disease and Alzheimer's disease (Sohrabji, et. al., Neuroendocrinology (2006), 27(4), 404-414).

Thus, the compounds of the invention, which are Trk inhibitors, may be useful in the treatment of multiple types of acute and chronic pain including but not limited to inflammatory pain, neuropathic pain, and pain associated with cancer, surgery and bone fracture. The compounds may also useful in the treatment of cancer, inflammation, neurodegenerative diseases and certain infectious diseases.

SUMMARY OF THE INVENTION

The present invention is directed to compounds of generic formula I and Ia below or pharmaceutically acceptable salts thereof that are useful as a Trk kinase mediator of NGF driven biological responses, an inhibitor of TrkA and other Trk kinases.

The invention is further directed to methods of treating a patient (preferably a human) for diseases or disorders in which the NGF receptor Trk kinases are involved, in particular TrkA. The invention further involves use of the compounds as NGF receptor TrkA inhibitor and/or antagonist for the preparation of a medicament for the treatment and/or prevention of diseases associated with inhibiting TrkA, which may include pain, cancer, restenosis, atherosclerosis, psoriasis, thrombosis, or a disease, disorder, or injury relating to dysmyelination or demyelination. The invention is also directed to pharmaceutical compositions which include an effective amount of a compound of formula I and Ia, or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula I and Ia

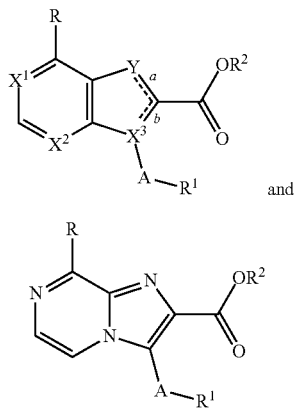

and pharmaceutically acceptable salts thereof, wherein
———— is a bond that when present forms a double bond with bond a or bond b;
$X^1$ is —N, —N=O or —$CR^3$;
$X^2$, $X^3$ and Y are independently selected from —N, or —CH;
R is a $C_{6-10}$ aryl, $C_{5-10}$ heteroaryl, halo, or hydrogen, said aryl and heteroaryl optionally substituted with 1 to 3 groups of $R^a$;
$R^1$ is a $(CH_2)_nC_{6-10}$ aryl, $(CH_2)_nC_{5-10}$ heteroaryl, or hydrogen, said aryl and heteroaryl optionally substituted with 1 to 3 groups of $R^b$;
$R^2$ is H, or $C_{1-6}$ alkyl;
A is $C_{1-6}$ alkyl, $C_{2-6}$ alkenyl, $C_{2-6}$ alkynyl, —$(CH_2)_nO$—, —$(CH_2)_nS(O)_2$—, —$CH_2C(O)NH$—, —O—, or —$NR^2$—,
$R^3$ is hydrogen, CN, or $C_{5-10}$ heterocyclyl, said heterocyclyl optionally substituted with 1 to 3 groups of $R^a$
$R^a$ is —CN, —$C_{1-4}$haloalkyl, halo, —$C_{1-6}$alkyl, —OR, —$NR^2R^2$, or —$NH(CH_2)_nOH$;
$R^b$ is —CN, —$C_{1-4}$haloalkyl, —$OC_{1-4}$haloalkyl, —O$(CH_2)_n$haloalkyl, —$C_{1-6}$alkyl, —$C_{1-6}$alkenyl, —$C_{1-6}$alkynyl, —$(CH_2)_nC_{6-10}$ aryl, —$(CH_2)_nC_{5-10}$ heterocyclyl, —$(CH_2)_nO$—$C_{6-10}$aryl, —$(CH_2)_nO$—$C_5$-10 heterocyclyl, —$C(O)C_{6-10}$aryl, —$NHC_{6-10}$aryl, halo, —OR, —$NR^2R^2$, $SO_2R^2$, said aryl and heterocyclyl optionally substituted with 1 to 3 groups of $R^a$; and
n is 0-4.

An embodiment of this invention is realized when $R^1$ is hydrogen and all other variables are as originally described.

In another embodiment of this invention $R^1$ is optionally substituted $C_{6-10}$ aryl and all other variables are as originally described. A subembodiment of this invention is realized when $R^1$ is optionally substituted phenyl.

In another embodiment of this invention $R^1$ is optionally substituted $C_{5-10}$ heterocyclyl and all other variables are as originally described. A subembodiment of this invention is realized when $R^1$ is optionally substituted oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl. In a further subembodiment of this invention $R^1$ is oxadiazolyl, quinolinyl or isoquinolinyl.

In yet another embodiment of this invention R is halo and all other variables are as originally described.

In another embodiment of this invention R is hydrogen and all other variables are as originally described.

In still another embodiment of this invention R is optionally substituted $C_{6-10}$ aryl and all other variables are as originally described. In a subembodiment of this invention R is optionally substituted phenyl.

In another subembodiment of this invention R is optionally substituted $C_{5-10}$ heteroaryl and all other variables are as originally described. A subembodiment of this invention is realized when R is optionally substituted quinolinyl, indolyl, isoquinolinyl, pyridyl, thiazolyl, or pyrimidinyl, preferably quinolinyl or isoquinolinyl.

In still another embodiment of this invention A is $C_{1-6}$ alkyl and all other variables are as originally described.

In another embodiment of this invention A is —$(CH_2)_nO$—, and all other variables are as originally described.

In another embodiment of this invention A is —$NR^2$— and all other variables are as originally described.

In yet another embodiment of this invention $R^3$ is CN and all other variables are as originally described.

In another embodiment of this invention $R^3$ is hydrogen and all other variables are as originally described.

In another embodiment of this invention $R^3$ is optionally substituted C5-10 heterocyclyl and all other variables are as originally described. A subembodiment of this invention is realized when $R^3$ is optionally substituted pyrazolyl, pyrazinyl, pyrimidinyl, isothiazolyl, pyridyl, furanyl, or thiazolyl.

In another embodiment of this invention $X^1$ is —N and all other variables are as originally described.

In still another embodiment of this invention $X^1$ is $CR^3$ and all other variables are as originally described.

In another embodiment of this invention $X^1$ is —N=O and all other variables are as originally described.

In another embodiment of this invention Y is —N and all other variables are as originally described.

In another embodiment of this invention Y is —CH— and all other variables are as originally described.

In another embodiment of this invention $X^2$ is —N and all other variables are as originally described.

In another embodiment of this invention $X^2$ is —CH— and all other variables are as originally described.

In another embodiment of this invention $X^3$ is —N and all other variables are as originally described.

In another embodiment of this invention $X^3$ is —CH— and all other variables are as originally described.

In another embodiment of this invention ———— forms a double bond with bond a, $X^1$ is —N=O and $X^2$ is —CH, $X^3$ is N, Y is —CH, and all other variables are as originally described.

In another embodiment of this invention ———— forms a double bond with bond a, $X^1$ is —N and $X^2$ is —CH, $X^3$ is N, Y is —CH, and all other variables are as originally described.

In another embodiment of this invention ———— forms a double bond with bond b, $X^1$ is —$CR^3$, and $X^2$ and $X^3$ are —CH, Y is —CH, and all other variables are as originally described. A subembodiment of this invention is realized when $R^3$ is selected from the group consisting of CN and optionally substituted pyrazolyl, pyrazinyl, pyrimidinyl, isothiazolyl, pyridyl, furanyl, and thiazolyl.

In another embodiment of this invention ———— forms a double bond with bond a, $X^1$ is —N and $X^2$ is —CH, $X^3$ is N, Y is —N, and all other variables are as originally described.

In another embodiment of this invention ———— forms a double bond with bond b, $X^1$ is —$CR^3$, and $X^2$ and $X^3$ are —CH, Y is —N, and all other variables are as originally described. A subembodiment of this invention is realized when $R^3$ is selected from the group consisting of CN and optionally substituted pyrazolyl, pyrazinyl, pyrimidinyl, isothiazolyl, pyridyl, furanyl, and thiazolyl.

In another embodiment n is 0 to 3, preferably 0 to 2 and more preferably 0 to 1.

Still in another embodiment the compounds of the invention are represented by structural formula I and pharmaceutically acceptable salts thereof, wherein R, $R^1$, $R^2$, $X^1$, $X^2$, $X^3$, and A are as originally described.

In another embodiment the compounds of formula I is represented by structural formula II:

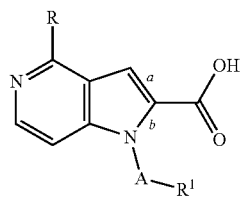

II and pharmaceutically acceptable salts thereof, wherein R, $R^1$ and A are as originally described. A subembodiment of formula II is realized when R is optionally substituted phenyl, quinolinyl, indolyl, isoquinolinyl, pyridyl, thiazolyl, or pyrimidinyl. Another subembodiment of formula II is realized when R is optionally substituted phenyl. Another subembodiment of formula II is realized when A is —$(CH_2)_nO$— or $C_{1-6}$ alkyl, preferably —$(CH_2)_nO$—. Still another embodiment of formula II is realized when $R^1$ is optionally substituted phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl. Yet another embodiment of formula II is realized when $R^1$ is optionally substituted phenyl.

Still another embodiment of the invention of formula II is realized when R is optionally substituted phenyl, A is —$(CH_2)_nO$—, and $R^1$ is optionally substituted phenyl.

In another embodiment the compounds of formula I is represented by structural formula IIa:

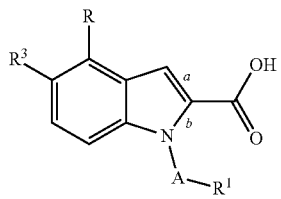

IIa and pharmaceutically acceptable salts thereof, wherein $R^3$, R, $R^1$, and A are as originally described. A subembodiment of formula IIa is realized when R is optionally substituted phenyl, quinolinyl, indolyl, isoquinolinyl, pyridyl, thiazolyl, or pyrimidinyl. Another subembodiment of formula IIa is realized when R is optionally substituted phenyl. Another subembodiment of formula IIa is realized when A is —$(CH_2)_nO$— or $C_{1-6}$ alkyl, preferably —$(CH_2)_nO$—. Still another embodiment of formula IIa is realized when $R^1$ is optionally substituted phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl. Yet another embodiment of formula IIa is realized when $R^1$ is optionally substituted phenyl. Another embodiment of formula IIa is realized when $R^3$ is CN or optionally substituted pyrazolyl, pyrazinyl, pyrimidinyl, isothiazolyl, pyridyl, furanyl, or thiazolyl.

Still another embodiment of the invention of formula IIa is realized when R is optionally substituted phenyl, A is —$(CH_2)_nO$—, and $R^1$ is optionally substituted phenyl.

In another embodiment the compounds of formula I is represented by structural formula IIb:

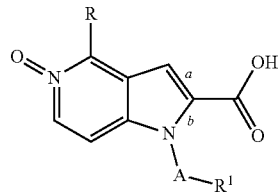

IIb and pharmaceutically acceptable salts thereof, wherein R, $R^1$, and A are as originally described. A subembodiment of formula IIb is realized when R is optionally substituted phenyl, quinolinyl, indolyl, isoquinolinyl, pyridyl, thiazolyl, or pyrimidinyl. Another subembodiment of formula rib is realized when R is optionally substituted phenyl. Another subembodiment of formula IIb is realized when A is —$(CH_2)_nO$— or $C_{1-6}$ alkyl, preferably —$(CH_2)_nO$—. Still another embodiment of formula IIb is realized when $R^1$ is optionally substituted phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl. Yet another embodiment of formula fib is realized when $R^1$ is optionally substituted phenyl.

Still another embodiment of the invention of formula IIb is realized when R is optionally substituted phenyl, A is —$(CH_2)_nO$—, and $R^1$ is optionally substituted phenyl.

In another embodiment the compounds of the invention are represented by structural Ia':

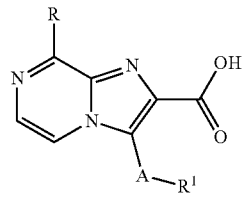

Ia' and pharmaceutically acceptable salts thereof, wherein R, $R^1$, and A are as originally described. A subembodiment of formula Ia' is realized when R is optionally substituted phenyl, quinolinyl, indolyl, isoquinolinyl, pyridyl, thiazolyl, or pyrimidinyl. Another subembodiment of formula Ia' is realized when R is optionally substituted phenyl. Another subembodiment of formula Ia' is realized when A is —$(CH_2)_nO$— or $C_{1-6}$ alkyl, preferably —$(CH_2)_nO$—. Still another embodiment of formula Ia' is realized when $R^1$ is optionally substituted phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl. Yet another embodiment of formula Ia' is realized when $R^1$ is optionally substituted phenyl.

Still another embodiment of the invention of formula Ia' is realized when R is optionally substituted phenyl, A is —(CH$_2$)$_n$O—, and R$^1$ is optionally substituted phenyl.

Examples of compounds of this invention include those in Table 1:

4-(3-Methoxyphenyl)-1-(3-phenylpropyl)-1H-pyrrolo[3,2-c]pyridine-2-carboxylic acid,
4-(3-Methoxyphenyl)-1-[(2E)-3-phenylprop-2-en-1-yl]-1H-pyrrolo[3,2-c]pyridine-2-carboxylic acid,
3:4-(3-Methoxyphenyl)-1-[2-oxo-2-(phenylamino)ethyl]-1H-pyrrolo[3,2-c]pyridine-2-carboxylic acid,
1-[2-(Benzylamino)-2-oxoethyl]-4-(3-methoxyphenyl)-1H-pyrrolo[3,2-c]pyridine-2-carboxylic acid,
5:4-(3-Methoxyphenyl)-1-(3-phenylprop-2-yn-1-yl)-1H-pyrrolo[3,2-c]pyridine-2-carboxylic acid,
4-(3-Ethoxyphenyl)-1-(2-phenoxyethyl)-1H-pyrrolo[3,2-c]pyridine-2-carboxylic acid,
4-(3-ethoxyphenyl)-1-(2-phenylethyl)-1H-pyrrolo[3,2-c]pyridine-2-carboxylic acid,
4-(3-ethoxyphenyl)-1-(3-phenoxypropyl)-1H-pyrrolo[3,2-c]pyridine-2-carboxylic acid,
1-[2-(4-chlorophenoxy)ethyl]-4-(3-ethoxyphenyl)-1H-pyrrolo[3,2-c]pyridine-2-carboxylic acid,
1-(biphenyl-4-ylmethyl)-4-(3-ethoxyphenyl)-1H-pyrrolo[3,2-c]pyridine-2-carboxylic acid,
1-[2-(benzylsulfonyl)ethyl]-4-(3-ethoxyphenyl)-1H-pyrrolo[3,2-c]pyridine-2-carboxylic acid,
4-(3-ethoxyphenyl)-1-[2-(phenylsulfonyl)ethyl]-1H-pyrrolo[3,2-c]pyridine-2-carboxylic acid,
1-[2-(benzyloxy)ethyl]-4-(3-ethoxyphenyl)-1H-pyrrolo[3,2-c]pyridine-2-carboxylic acid,
4-(3-ethoxyphenyl)-1-(4-phenoxybenzyl)-1H-pyrrolo[3,2-c]pyridine-2-carboxylic acid,
4-(3-ethoxyphenyl)-1-[4-(phenoxymethyl)benzyl]-1H-pyrrolo[3,2-c]pyridine-2-carboxylic acid,
1-[(5-phenyl-1,2,4-oxadiazol-3-yl)methyl]-4-(quinolin-5-yl)-1H-pyrrolo[3,2-c]pyridine-2-carboxylic acid,
1-[2-(4-chlorophenoxy)ethyl]-4-[3-(propan-2-yloxy)phenyl]-1H-pyrrolo[3,2-c]pyridine-2-carboxylic acid,
1-[2-(4-chlorophenoxy)ethyl]-4-(3-propoxyphenyl)-1H-pyrrolo[3,2-c]pyridine-2-carboxylic acid,
1-[2-(4-chlorophenoxy)ethyl]-4-[3-(2-methylpropoxy)phenyl]-1H-pyrrolo[3,2-c]pyridine-2-carboxylic acid,
4-(3-ethoxyphenyl)-7-{2-[4-(trifluoromethoxy)phenoxy]ethyl}-7H-pyrrolo[2,3-d]pyrimidine-6-carboxylic acid,
4-(3-Ethoxyphenyl)-1-[(1-phenylpyrrolidin-3-yl)methyl]-1H-pyrrolo[3,2-c]pyridine-2-carboxylic acid,
4-(3-Ethoxyphenyl)-1-[(5-phenyl-1H-pyrazol-3-yl)methyl]-1H-pyrrolo[3,2-c]pyridine-2-carboxylic acid,
4-(3-ethoxyphenyl)-1-[(5-oxo-1-phenylpyrrolidin-3-yl)methyl]-1H-pyrrolo[3,2-c]pyridine-2-carboxylic acid,
1-(2-{[1-(phenylcarbonyl)piperidin-4-yl]oxy}ethyl)-4-(3-propoxyphenyl)-1H-pyrrolo[3,2-c]pyridine-2-carboxylic acid,
1-{2-[(1-benzylpiperidin-4-yl)oxy]ethyl}-4-(3-propoxyphenyl)-1H-pyrrolo[3,2-e]pyridine-2-carboxylic acid,
4-(3-ethoxyphenyl)-1-({2-[4-(trifluoromethoxy)phenyl]-1,3-thiazol-4-yl}methyl)-1H-pyrrolo[3,2-c]pyridine-2-carboxylic acid,
4-(3-ethoxyphenyl)-1-({2-[4-(trifluoromethoxy)phenyl]-1,3-oxazol-4-yl}methyl)-1H-pyrrolo[3,2-c]pyridine-2-carboxylic acid,
4-(3-ethoxyphenyl)-1-[2-(quinolin-5-yloxy)ethyl]-1H-pyrrolo[3,2-c]pyridine-2-carboxylic acid,
4-(3-ethoxyphenyl)-1-[2-(isoquinolin-5-yloxy)ethyl]-1H-pyrrolo[3,2-c]pyridine-2-carboxylic acid,
4-(3-ethoxyphenyl)-1-[2-(isoquinolin-8-yloxy)ethyl]-1H-pyrrolo[3,2-c]pyridine-2-carboxylic acid,
4-(3-Ethoxyphenyl)-1-{2-[4-(trifluoromethoxy)phenoxy]ethyl}-1H-pyrrolo[3,2-c]pyridine-2-carboxylic acid,
1-[2-(2,4-dichlorophenoxy)ethyl]-4-(3-ethoxyphenyl)-1H-pyrrolo[3,2-c]pyridine-2-carboxylic acid,
1-[2-(3,4-dichlorophenoxy)ethyl]-4-(3-ethoxyphenyl)-1H-pyrrolo[3,2-c]pyridine-2-carboxylic acid,
1-[2-(4-cyanophenoxy)ethyl]-4-(3-ethoxyphenyl)-1H-pyrrolo[3,2-c]pyridine-2-carboxylic acid,
4-(3-ethoxyphenyl)-1-{2-[4-(methylsulfonyl)phenoxy]ethyl}-1H-pyrrolo[3,2-c]pyridine-2-carboxylic acid,
4-(3-ethoxyphenyl)-1-{2-[4-(trifluoromethyl)phenoxy]ethyl}-1H-pyrrolo[3,2-c]pyridine-2-carboxylic acid,
4-(3-Ethoxyphenyl)-1-(2-{[6-(trifluoromethyl)pyridin-3-yl]oxy}ethyl)-1H-pyrrolo[3,2-c]pyridine-2-carboxylic acid,
1-{2-[(5-chloropyridin-2-yl)oxy]ethyl}-4-(3-ethoxyphenyl)-1H-pyrrolo[3,2-c]pyridine-2-carboxylic acid,
4-(3-ethoxyphenyl)-1-{2-[4-(2,2,2-trifluoroethoxy)phenoxy]ethyl}-1H-pyrrolo[3,2-c]pyridine-2-carboxylic acid,
4-(3-ethoxyphenyl)-1-[2-(4-phenoxyphenoxy)ethyl]-1H-pyrrolo[3,2-c]pyridine-2-carboxylic acid,
4-(3-ethoxyphenyl)-1-(2-{[2-(trifluoromethyl)pyrimidin-5-yl]oxy}ethyl)-1H-pyrrolo[3,2-c]pyridine-2-carboxylic acid,
4-(3-ethoxyphenyl)-1-(2-{[1-methyl-3-(trifluoromethyl)-1H-pyrazol-5-yl]oxy}ethyl)-1H-pyrrolo[3,2-c]pyridine-2-carboxylic acid,
1-[2-(4-benzylphenoxy)ethyl]-4-(3-ethoxyphenyl)-1H-pyrrolo[3,2-c]pyridine-2-carboxylic acid,
4-(3-ethoxyphenyl)-1-{2-[4-(phenylamino)phenoxy]ethyl}-1H-pyrrolo[3,2-c]pyridine-2-carboxylic acid,
4-(3-ethoxyphenyl)-1-{2-[4-(tetrahydro-2h-pyran-4-yloxy)phenoxy]ethyl}-1H-pyrrolo[3,2-c]pyridine-2-carboxylic acid,
4-(3-ethoxyphenyl)-1-{2-[4-(tetrahydrofuran-3-yloxy)phenoxy]ethyl}-1H-pyrrolo[3,2-c]pyridine-2-carboxylic acid,
4-(3-ethoxyphenyl)-1-{2-[4-(trifluoromethoxy)phenoxy]ethyl}-1H-pyrrolo[3,2-c]pyridine,
4-[(3-Methoxyphenyl)amino]-1-[(5-phenyl-1,2,4-oxadiazol-3-yl)methyl]-1H-pyrrolo[3,2-c]pyridine-2-carboxylic acid,
1-[(5-Phenyl-1,2,4-oxadiazol-3-yl)methyl]-4-(quinolin-8-yl)-1H-pyrrolo[3,2-c]pyridine-2-carboxylic acid,
4-(isoquinolin-5-yl)-1-[(5-phenyl-1,2,4-oxadiazol-3-yl)methyl]-1H-pyrrolo[3,2-c]pyridine-2-carboxylic acid,
4-(1-methyl-1H-indol-4-yl)-1-[(5-phenyl-1,2,4-oxadiazol-3-yl)methyl]-1H-pyrrolo[3,2-c]pyridine-2-carboxylic acid,
4-(Isoquinolin-4-yl)-1-[(5-phenyl-1,2,4-oxadiazol-3-yl)methyl]-1H-pyrrolo[3,2-c]pyridine-2-carboxylic acid,
1-[2-(4-Chlorophenoxy)ethyl]-4-(2-ethoxypyridin-4-yl)-1H-pyrrolo[3,2-c]pyridine-2-carboxylic acid,
4-(2-Ethoxy-1,3-thiazol-4-yl)-1-{2-[4-(trifluoromethoxy)phenoxy]ethyl}-1H-pyrrolo[3,2-c]pyridine-2-carboxylic acid,
4-[2-(propylamino)pyridin-4-yl]-1-{2-[4-(trifluoromethoxy)phenoxy]ethyl}-1H-pyrrolo[3,2-c]pyridine-2-carboxylic acid,
4-[2-(propylamino)-1,3-thiazol-5-yl]-1-{2-[4-(trifluoromethoxy)phenoxy]ethyl}-1H-pyrrolo[3,2-c]pyridine-2-carboxylic acid,
4-[2-(propylamino)pyrimidin-4-yl]-1-{2-[4-(trifluoromethoxy)phenoxy]ethyl}-1H-pyrrolo[3,2-c]pyridine-2-carboxylic acid, 4-{2-[(2-Hydroxyethyl)amino]pyridin-4-yl}-1-{2-[4-(trifluoromethoxy)phenoxy]ethyl}-1H-pyrrolo[3,2-c]pyridine-2-carboxylic acid, 4-(3-Ethoxyphenyl)-1-(2-{[4-(2,2,2-trifluoroethoxy)phenyl]amino}ethyl)-1H-pyrrolo[3,2-c]pyridine-2-carboxylic acid4-[2-(3-Methylpyrrolidin-1-yl)-1,3-thiazol-5-yl]-1-{2-[4-(trifluoromethoxy)phenoxy]ethyl}-1H-pyrrolo[3,2-c]pyridine-2-carboxylic acid, 1-[2-(4-Tert-butoxyphenyl)ethyl]-4-(3-ethoxyphenyl)-1H-pyrrolo[3,2-c]pyridine-2-carboxylic acid, 4-(isoquinolin-5-yl)-1-{2-[4-(trifluoromethoxy)phenoxy]ethyl}-1H-pyrrolo[3,2-c]pyridine-2-carboxylic acid, 4-(quinolin-5-yl)-1-{2-[4-(trifluoromethoxy)phenoxy]ethyl}-1H-pyrrolo[3,2-c]pyridine-2-carboxylic acid, 4-(quinolin-4-yl)-1-{2-[4-(trifluoromethoxy)phenoxy]ethyl}-1H-pyrrolo[3,2-c]pyridine-2-carboxylic acid, 4-(isoquinolin-4-yl)-1-{2-[4-(trifluoromethoxy)phenoxy]ethyl}-1H-pyrrolo[3,2-c]pyridine-2-carboxylic acid, 4-(3-Ethoxyphenyl)-1-{2-[4-(pyridin-3-yloxy)phenoxy]ethyl}-1H-pyrrolo[3,2-c]pyridine-2-carboxylic acid, 4-(3-ethoxyphenyl)-1-{2-[4-(pyridin-2-yloxy)phenoxy]ethyl}-1H-pyrrolo[3,2-c]pyridine-2-carboxylic acid, 4-(3-ethoxyphenyl)-1-{2-[4-(pyridin-4-yloxy)phenoxy]ethyl}-1H-pyrrolo[3,2-c]pyridine-2-carboxylic acid, 4-(3-ethoxyphenyl)-1-{2-[4-(pyrimidin-2-yloxy)phenoxy]ethyl}-1H-pyrrolo[3,2-c]pyridine-2-carboxylic acid, 4-(3-ethoxyphenyl)-1-{2-[4-(pyrimidin-5-yloxy)phenoxy]ethyl}-1H-pyrrolo[3,2-c]pyridine-2-carboxylic acid, 4-(3-ethoxyphenyl)-1-{2-[4-(pyrazin-2-yloxy)phenoxy]ethyl}-1H-pyrrolo[3,2-c]pyridine-2-carboxylic acid, 4-(3-ethoxyphenyl)-1-{2-[4-(1,3-thiazol-2-yloxy)phenoxy]ethyl}-1H-pyrrolo[3,2-c]pyridine-2-carboxylic acid, 1-{2-[4-(Trifluoromethoxy)phenoxy]ethyl}-1H-pyrrolo[3,2-c]pyridine-2-carboxylic acid, 5-cyano-1-{2-[4-(trifluoromethoxy)phenoxy]ethyl}-1H-indole-2-carboxylic acid, 5-(1H-pyrazol-4-yl)-1-{2-[4-(trifluoromethoxy)phenoxy]ethyl}-1H-indole-2-carboxylic acid, 5-(pyrazin-2-yl)-1-{2-[4-(trifluoromethoxy)phenoxy]ethyl}-1H-indole-2-carboxylic acid, 5-pyrimidin-5-yl-1-{2-[4-(trifluoromethoxy)phenoxy]ethyl}-1H-indole-2-carboxylic acid, 5-(1H-pyrazol-3-yl)-1-{2-[4-(trifluoromethoxy)phenoxy]ethyl}-1H-indole-2-carboxylic acid, 5-isothiazol-4-yl-1-{2-[4-(trifluoromethoxy)phenoxy]ethyl}-1H-indole-2-carboxylic acid, 5-pyridin-3-yl-1-{2-[4-(trifluoromethoxy)phenoxy]ethyl}-1H-indole-2-carboxylic acid, 5-furan-3-yl-1-{2-[4-(trifluoromethoxy)phenoxy]ethyl}-1H-indole-2-carboxylic acid, 5-pyrimidin-4-yl-1-{2-[4-(trifluoromethoxy)phenoxy]ethyl}-1H-indole-2-carboxylic acid, 5-pyridin-4-yl-1-{2-[4-(trifluoromethoxy)phenoxy]ethyl}-1H-indole-2-carboxylic acid, 5-isothiazol-3-yl-1-{2-[4-(trifluoromethoxy)phenoxy]ethyl}-1H-indole-2-carboxylic acid, 5-(1,3-thiazol-2-yl)-1-{2-[4-(trifluoromethoxy)phenoxy]ethyl}-1H-indole-2-carboxylic acid, 5-(1,3-thiazol-4-yl)-1-{2-[4-(trifluoromethoxy)phenoxy]ethyl}-1H-indole-2-carboxylic acid, 5-pyridin-2-yl-1-{2-[4-(trifluoromethoxy)phenoxy]ethyl}-1H-indole-2-carboxylic acid, 5-furan-2-yl-1-{2-[4-(trifluoromethoxy)phenoxy]ethyl}-1H-indole-2-carboxylic acid, 7-chloro-3-{2-[4-(trifluoromethoxy)phenoxy]ethyl}-1H-pyrrolo[2,3-c]pyridine-2-carboxylic acid, 7-(3-ethoxyphenyl)-3-{2-[4-(trifluoromethoxy)phenoxy]ethyl}-1H-pyrrolo[2,3-c]pyridine-2-carboxylic acid, 8-(3-ethoxyphenyl)-3-{2-[4-(trifluoromethoxy)phenoxy]ethyl}imidazo[1,2-a]pyrazine-2-carboxylic acid, and pharmaceutically acceptable salts thereof.

Particular examples of the compounds of this invention are:

4-[2-(propylamino)pyrimidin-4-yl]-1-{2-[4-(trifluoromethoxy)phenoxy]ethyl}-1H-pyrrolo[3,2-c]pyridine-2-carboxylic acid, 4-[2-(propylamino)pyridin-4-yl]-1-{2-[4-(trifluoromethoxy)phenoxy]ethyl}-1H-pyrrolo[3,2-c]pyridine-2-carboxylic acid.

1-[2-(4-Tert-butoxyphenyl)ethyl]-4-(3-ethoxyphenyl)-1H-pyrrolo[3,2-c]pyridine-2-carboxylic acid.

5-pyrimidin-5-yl-1-{2-[4-(trifluoromethoxy)phenoxy]ethyl}-1H-indole-2-carboxylic acid.

5-(1H-pyrazol-4-yl)-1-{2-[4-(trifluoromethoxy)phenoxy]ethyl}-1H-indole-2-carboxylic acid, 5-cyano-1-{2-[4-(trifluoromethoxy)phenoxy]ethyl}-1H-indole-2-carboxylic acid, 7-(3-ethoxyphenyl)-3-{2-[4-(trifluoromethoxy)phenoxy]ethyl}-1H-pyrrolo[2,3-c]pyridine-2-carboxylic acid, 8-(3-ethoxyphenyl)-3-{2-[4-(trifluoromethoxy)phenoxy]ethyl}imidazo[1,2-a]pyrazine-2-carboxylic acid, 4-(3-Ethoxyphenyl)-1-{2-[4-(trifluoromethoxy)phenoxy]ethyl}-1H-pyrrolo[3,2-c]pyridine-2-carboxylic acid, 4-(3-ethoxyphenyl)-1-[2-(4-phenoxyphenoxy)ethyl]-1H-pyrrolo[3,2-c]pyridine-2-carboxylic acid, 1-[2-(4-benzylphenoxy)ethyl]-4-(3-ethoxyphenyl)-1H-pyrrolo[3,2-c]pyridine-2-carboxylic acid and pharmaceutically acceptable salts thereof.

The invention is also directed to methods of treating a patient (preferably a human) for diseases or disorders in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a therapeutically effective amount of a compound of the invention, or a pharmaceutically acceptable salt thereof.

The invention is also directed to the use of a compound of the invention for treating a disease or disorder in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a compound of the invention, or a pharmaceutically acceptable salt thereof.

The invention is also directed to medicaments or pharmaceutical compositions for the treatment of diseases or disorders in a patient (preferably a human) in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, which comprise a compound of the invention, or a pharmaceutically acceptable salt thereof, and a pharmaceutically acceptable carrier.

The invention is also directed to a method for the manufacture of a medicament or a pharmaceutical composition for treating diseases in which TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA comprising combining a compound of the invention or a pharmaceutically acceptable salt thereof, with a pharmaceutically acceptable carrier.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. Co alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl), benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

When a heterocyclyl group as defined herein is substituted, the substituent may be bonded to a ring carbon atom of the heteroaryl group, or on a ring heteroatom (L e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

As used herein, unless otherwise specifically defined, substituted alkyl, substituted cycloalkyl, substituted aryl, substituted heteroaryl, and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1\text{-}C_6 \text{ alkyl})_2$, $NO_2$, CN, $(C_1\text{-}C_6 \text{ alkyl})O$—, (aryl)O—, —OH, $(C_1\text{-}C_6 \text{ alkyl})S(O)_m$—, $(C_1\text{-}C_6 \text{ alkyl})C(O)NH$—, $H_2N$—C(NH)—, $(C_1\text{-}C_6 \text{ alkyl})C(O)$—, $(C_1\text{-}C_6 \text{ alkyl})OC(O)$—, $(C_1\text{-}C_6 \text{ alkyl})OC(O)NH$—, phenyl, pyridyl, imidazolyl, oxazolyl, isoxazolyl, thiazolyl, thienyl, furyl, isothiazolyl and $C_1\text{-}C_{20}$ alkyl.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula (I). For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula (I) can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term "TrkA" refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members TrkA, TrkB and TrkC that bind to and mediate the signal transduction derived from the Neurotrophins. Inhibitors of the Trk/neurotrophin pathway have been demonstrated to be highly effective in numerous preclinical animal models of pain. The compounds of the invention are modulators of the Trk receptors, particularly TrkA.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formula (I) disclosed herein as TrkA inhibitors in a patient or subject such as a mammal in need of such activity, comprising the administration of an effective amount of the compound. In addition to humans, a variety of other mammals can be treated according to the method of the present invention.

The compounds of the present invention may have utility in treating or ameliorating pain disorders (including pain associated with cancer, surgery, and bone fracture, acute pain, inflammatory pain and neuropathic pain). The compounds of formula I and Ia are also useful for treating cancers including neuroblastoma, ovarian, pancreatic and colorectal cancer. Other conditions that may be treated by the compounds of the invention include inflammation and certain infectious diseases, interstitial cystitis, painful bladder syndrome, urinary incontinence, asthma, anorexia, atopic dermatitis, and psoriasis. Treatment of demyelination and dysmyelination, by promoting myelination, neuronal survival, and oligodendrocyte differentiation via blocking Sp35-TrkA interaction may also be possible with the compounds of the present invention.

The compounds of formula I and Ia may also be useful in the treatment of bone-related diseases (e.g., those involved in bone resorption). Examples of bone-related diseases include metastatic bone disease, treatment-induce bone loss, osteoporosis, rheumatoid arthritis, ankylosing spondylitis, Paget's disease, and periodontal disease. Another bone disorder or disease that can be treated with the compounds of the claimed invention is metastatic tumor-induced osteolysis. Cancers known to cause tumor induced osteolysis are hematological malignancies such as myeloma and lymphoma and solid tumors such as breast, prostate, lung, renal and thyroid.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno- synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally mammals such a human being, male or female, in whom Trk-A and/or Trk-B modulation is desired. Thus, an aspect of the present invention is a method of treating diseases with an inhibitor of Trk-A and/or Trk-B comprising administering to said mammal one or more compounds of formula I and Ia or a pharmaceutically acceptable salt thereof in an amount effective to treat or prevent said disorder. A particular aspect of the invention is directed to a method of treating pain, cancer, inflammation, neurodegenerative disease or Typanosoma cruzi infection by administering to said mammal a therapeutically effective amount of a compound of formula I and Ia or a pharmaceutically acceptable salt thereof. Still another aspect of the present invention is directed to a method of treating osteolytic disease in a mammal by administering a therapeutically effective amount of a compound of formula I and Ia or a pharmaceutically acceptable salt thereof. For purposes of this invention mammals include dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of potential combinations of the compounds include combinations with agents for the treatment of pain, for example steroids such as dexamethasone, cortisone, and fluticasone, non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B 1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor JO modulators (e.g., a GABA- A receptor agonist); matrix metalloprotease (MMP) inhibitors; thrombolytic agents; chemotherapeutic agents, opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NIU antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

Another aspect of the present invention is directed to a pharmaceutical composition comprising a compound of formula I and Ia or a pharmaceutically acceptable salt thereof and a pharmaceutically acceptable diluent or carrier. Still another aspect of the present invention is directed to a compound of formula I and Ia or a pharmaceutically acceptable salt thereof, for use in the treatment of a condition treatable with an inhibitor of Trk-A and/or Trk-B, such as the disorders, conditions and/or diseases described herein. Still another aspect is directed to use of a compound of formula I and Ia or a pharmaceutically acceptable salt thereof in the treatment of pain, cancer, inflammation, neurodegenerative disease or typanosoma cruzi infection.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formula I and Ia, is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

During any of the synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P. G. M. Wuts, *Protective Groups in Organic Synthesis*, John Wiley & Sons, 1999. The protecting groups may be removed at a convenient sequent stage using methods known from the art.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The following abbreviations are used throughout the text:
ACN Acetonitrile
$BOC_2O$ Di-tert-butyl dicarbonate
CDI N,N'-Carbonyl diimidazole
$CH_3CN$ Acetonitrile
$Cs_2CO_3$ Cesium carbonate
CsF Cesium fluoride
DBU 1,8-Diazabicyclo[5.4.0]undec-7-ene
DCE Dichloroethane
DCM Dichloromethane
DIAD Diisopropyl azodicarboxylate
DIPEA Diisoproylethylamine
DMAP 4-Dimethylamino pyridine
DMF Dimethylformamide
DMSO Dimethyl sulfoxide
EDC N-(3-Dimethylaminopropyl)-N'-ethylcarbodiimide
$Et_3N$ Triethylamine
$Et_2O$ Diethyl ether
EtOAc Ethyl acetate
EtOH Ethanol
HATU O-(7-Azabenzotriazol-1-yl)-N,N,N',N'-tetramethyluronium hexafluorophosphate
HBr Hydrobromic acid
HCl Hydrochloric acid
$H_2O$ Water
HOAc Acetic acid
HOAt 1-Hydroxy-7-azabenzotriazole
$K_2CO_3$ Potassium carbonate
$KHSO_4$ Potassium bisulfate
LiOH Lithium hydroxide
mCPBA Meta-chloro-perbenzoic acid
MeCN Acetonitrile
MeOH Methanol
$MgSO_4$ Magnesium sulfate
MTBE Methyl tert-butyl ether
2-MeTHF 2-Methyl tetrahydrofuran
$N_2$ Nitrogen gas or atmosphere
$Na_2SO_4$ Sodium sulfate
$NaHCO_3$ Sodium bicarbonate
NaOH Sodium hydroxide
$NH_4Cl$ Ammonium chloride
$NH_4OH$ Ammonium hydroxide
NMO N-methylmorpholine N-oxide
NMP N-Methyl pyrrolidinone
Pd/C Palladium on carbon
$Pd(PPh_3)_4$ Tetrakis(triphenylphosphine)palladium (0)
PhMe Toluene
$PPh_3$ Triphenylphosphine
PPTS Pyridium p-toluenesulfonate
RT Room temperature
r.t. Room temperature
$SOCl_2$ Thionyl chloride
S-Phos 2-Dicyclohexylphosphino-2',6'-dimethoxybiphenyl SiO₂ Silica or silica gel
TBAF Tetrabutylammonium fluoride
TBTU O-Benzotriazol-1-yl-N,N,N',N'-tetramethyluronium tetrafluoroborate
TFA Trifluoroacetic acid
THF Tetrahydrofuran
X-Phos 2-Dicyclohexylphosphino-2',4',6'-triisopropylbiphenyl Reaction Scheme I illustrates the preparation of the compounds of the invention, starting with a commercially available pyridyl-iodide I-1. This material can be converted to the corresponding azaindole I-2. Intermediate I-2 reacts with either alkylating reagents to give I-3 or organometallic reagents to give I-4, both of which are converted to I-5 in several steps.

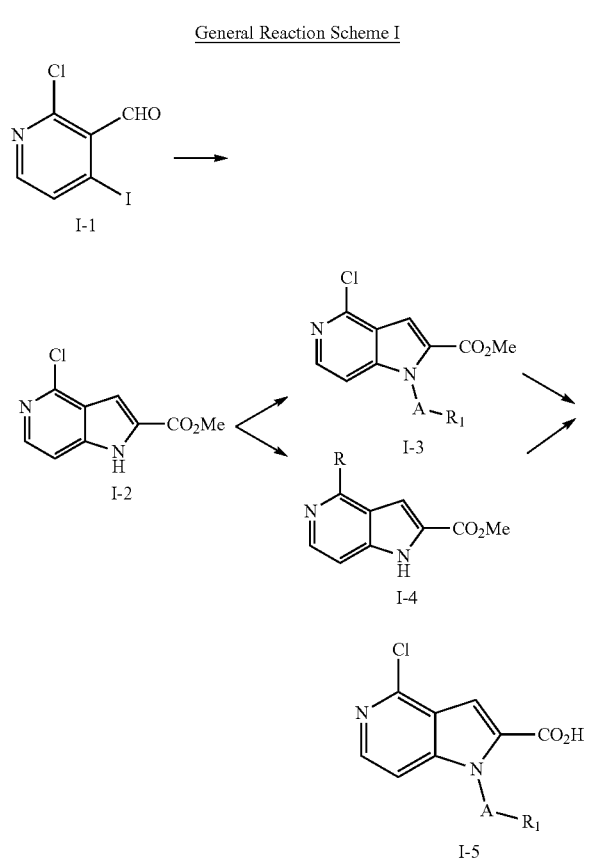

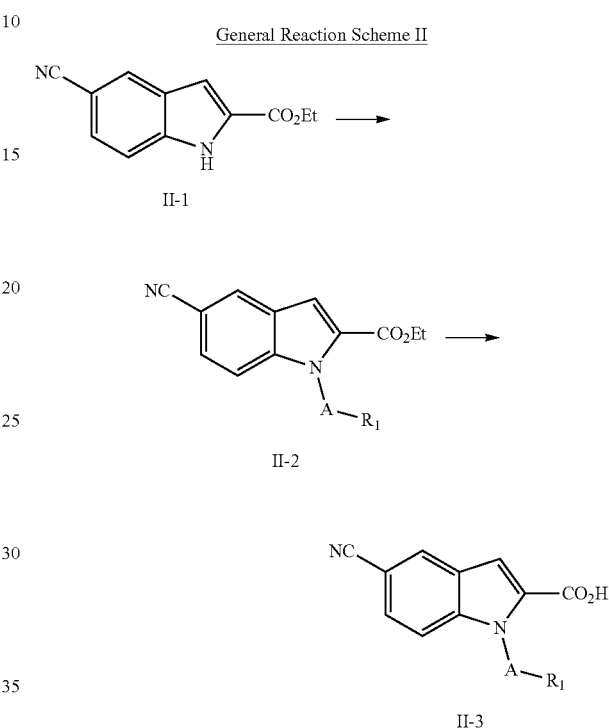

Reaction Scheme II illustrates the preparation of the compounds of the invention, starting with a commercially available cyano indole II-1. This material reacts with alkylating reagents to provide II-2. Intermediate II-2 is then hydrolyzed to II-3.

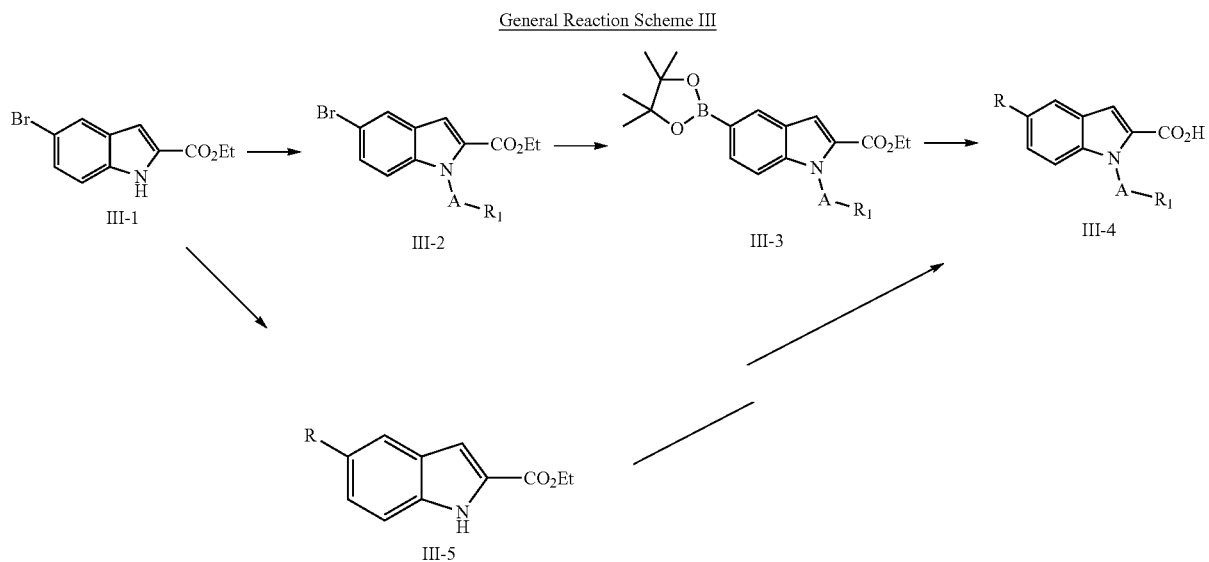

Reaction Scheme III illustrates the preparation of the compounds of the invention, starting with a commercially available bromo-indole III-1. This material reacts with alkylating agents to provide III-2. Intermediate III-2 was borylated to provide III-3 and III-4 is produced via reaction with organometallic reagents and hydrolysis. Alternatively, arylation can occur in the first step to give III-5 which is then converted to III-4 via alkylation/hydrolysis.

Reaction Scheme IV

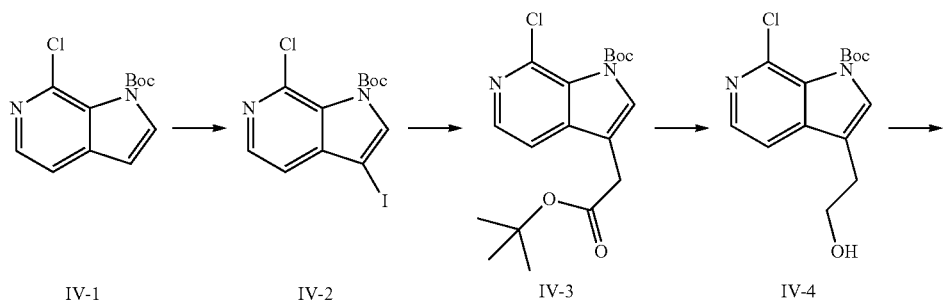

IV-1    IV-2    IV-3    IV-4

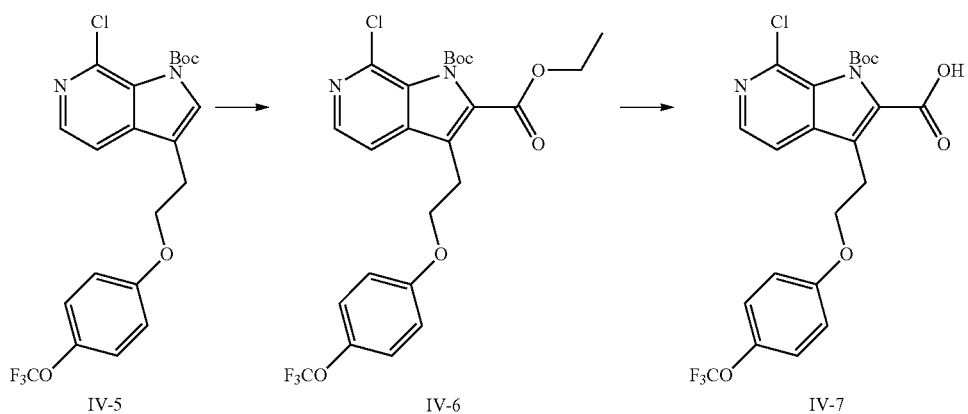

IV-5    IV-6    IV-7

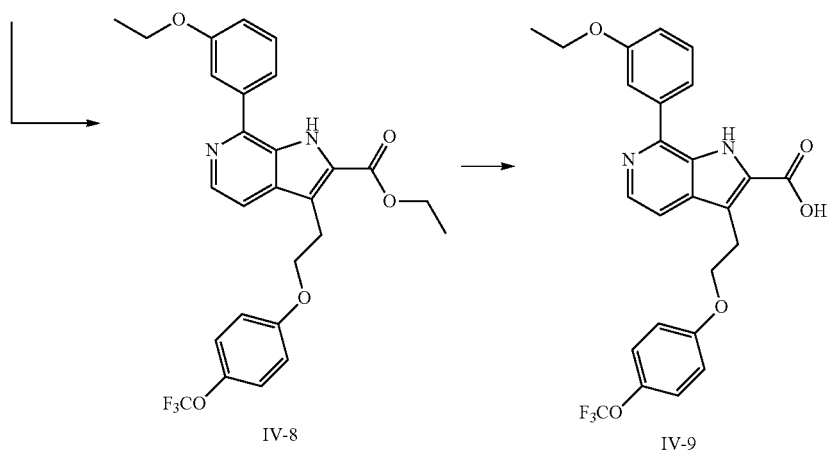

IV-8    IV-9

Reaction Scheme IV illustrates the preparation of the compounds of the invention, starting with a commercially available chloro-azaindole IV-1 which is readily iodinated to give IV-2. A cross-coupling and reduction sequence is then used to introduce the hydroxyethyl in IV-4. Introduction of the phenol portion is then accomplished using a Mitsunobu reaction and the carboxylate is introduced to form IV-6. Hydrolysis leads to acid IV-7. Alternatively, aryl and heteroaryl groups can be introduced to form IV-8, which also is readily converted to IV-9.

Reaction Scheme V

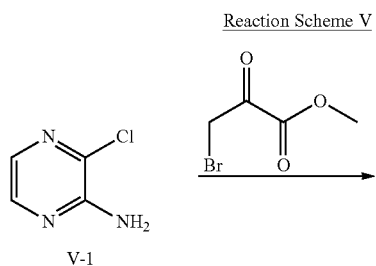

V-1

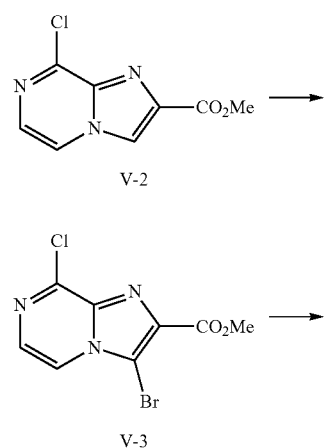

V-2

V-3

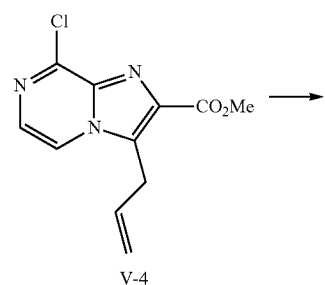

V-4

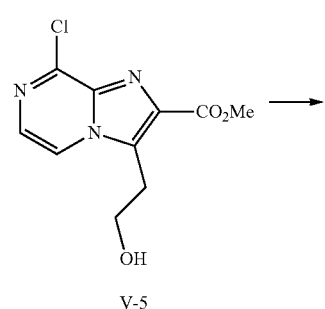

V-5

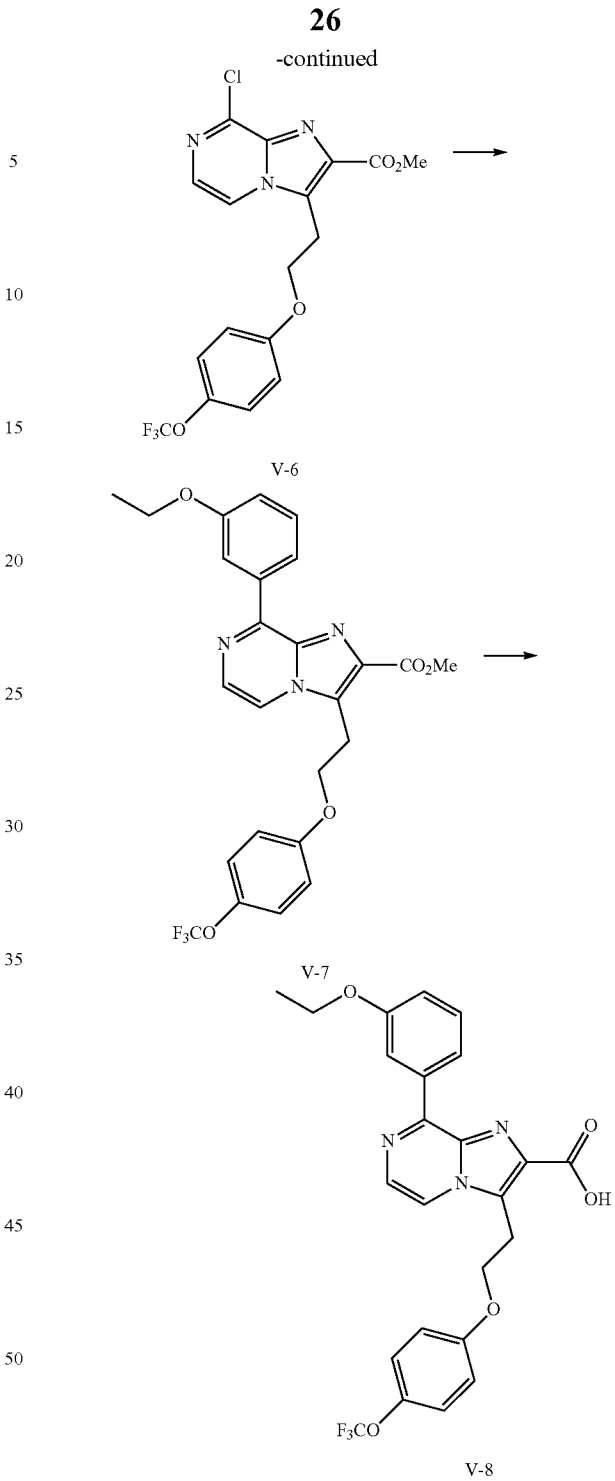

V-6

V-7

V-8

Reaction Scheme V illustrates the preparation of the compounds of the invention, starting with a commercially available aminopyrazine V-1 which is readily condensed to form imadazo-pyrazine V-2. Bromination and introduction of an ally group leads to V-4. A three step sequence yields hydroxyethyl analog V-5. Mitsunobu reaction with a phenol leads to V-6, which can be arylated to form V-8 after ester hydrolysis.

Specific embodiments of the compounds of the invention, and methods of making them, are described in the Examples herein. Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially or are readily prepared by one of ordinary skill in the art.

Synthesis of Intermediates A

Intermediate A1: Methyl 4-chloro-1H-pyrrolo[3,2-c]pyridine-2-carboxylate

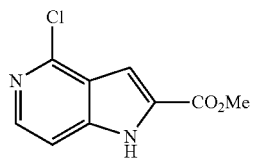

To a solution of (racemic)-benzyloxycarbonyl-α-phosphonoglycine trimethyl ester (12.08 g, 36.5 mmole) in 80 mL CH$_2$Cl$_2$ was added DBU (6.34 mL, 42.1 mmole) slowly at RT. After 30 minutes a solution of 2-chloro-3-formyl-4-iodopyridine (7.5 g, 28.0 mmole) in 20 mL CH$_2$Cl$_2$ was added slowly at RT. During the addition the reaction became slightly exothermic and was cooled via a cold water bath. After 4 hr the mixture was diluted with CH$_2$Cl$_2$ and washed with 1N aqueous HCl (2×) and H$_2$O (1×). The organic layer was dried (MgSO$_4$), filtered, and concentrated. Flash column (IS-CORedi-Sep 330 g SiO$_2$, 20% EtOAc/hexanes) gave methyl (2Z)-2-{[(benzyloxy)carbonyl]amino}-3-(2-chloro-4-iodopyridin-3-yl)prop-2-enoate (11.46 g, 86%) as a white solid. $^1$H NMR (399 MHz, CDCl$_3$): δ 7.89 (d, J=5.1 Hz, 1 H); 7.70 (d, J=5.1 Hz, 1 H); 7.33 (m, 3 H); 7.24 (m, 2 H); 7.06 (s, 1 H); 6.96 (s, 1 H); 4.97 (s, 2 H); 3.91 (s, 3 H).

Methyl (2Z)-2-{[(benzyloxy)carbonyl]amino}-3-(2-chloro-4-iodopyridin-3-yl)prop-2-enoate (11.46 g, 24.25 mmole), K$_2$CO$_3$ (10.05 g, 72.7 mmole), CuI (0.462 g, 2.425 mmole), and L-proline (0.558 g, 4.85 mmole) were combined in 1,4-dioxane (120 mL). The mixture was degassed (3× pump/N$_2$) then heated to reflux. After stirring at reflux overnight the mixture was cooled to RT, diluted with saturated aqueous NH$_4$Cl, and extracted with CH$_2$Cl$_2$ (3×). The combined organic layers were dried (MgSO$_4$), filtered through a pad of Celite, and concentrated. The resulting solid was triturated with Et$_2$O/hexanes to give the title compound (4.6 g, 90%) as an off-white solid. NMR (399 MHz, CDCl$_3$): δ 9.25 (s, 1 H); 8.18 (d, J=5.8 Hz, 1 H); 7.35 (d, J=2.1 Hz, 1 H); 7.29 (d, J=5.9 Hz, 1 H); 3.99 (s, 3 H).

Intermediate A2: Tert-butyl 2-methyl 4-chloro-1H-pyrrolo[3,2-c]pyridine-1,2-dicarboxylate

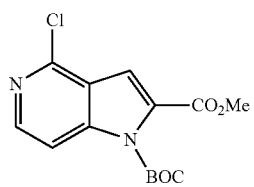 [SMILES: COC(=O)c1cc2c(Cl)nccc2n1C(=O)OC(C)(C)C]

To a solution of methyl 4-chloro-1H-pyrrolo[3,2-c]pyridine-2-carboxylate (500 mg, 2.374 mmole) in THF (10 mL) was added NaH (60% dispersion in mineral oil, 123 mg, 3.09 mmole) portionwise at RT. After gas evolution had ceased BOC$_2$O (674 mg, 3.09 mmole) was added. After 90 min the mixture was diluted with EtOAc, filtered through a pad of Celite washing with EtOAc, and concentrated. Flash column chromatography (Biotage-SNAP-50 g SiO$_2$, 0-20% EtOAc/hexanes) gave the title compound (620 mg, 84%) as an oil which solidified under vacuum $^1$H NMR (400 MHz, CDCl$_3$): δ 8.30 (d, J=5.8 Hz, 1 H); 7.89 (dd, J=5.8, 0.8 Hz, 1H); 7.20 (d, J=0.8 Hz, 1 H); 3.95 (s, 3 H); 1.64 (s, 9 H).

Synthesis of Intermediates B

Intermediate B 1:1-(2-Bromoethoxy)-4-(trifluoromethoxy)benzene

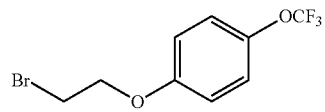 [SMILES: FC(F)(F)Oc1ccc(OCCBr)cc1]

To a solution of 4-(trifluoromethoxy)phenol (1 g, 5.61 mmole) in CH$_3$CN (20 mL) was added Cs$_2$CO$_3$ (3.66 g, 11.23 mmole) then 1,2-dibromoethane (2.42 mL, 28.1 mmole). The mixture was heated to reflux. After 3 days the mixture was cooled to RT, filtered through a pad of Celite washing with CH$_2$Cl$_2$, and concentrated. Flash column (Biotage-SNAP-50 g SiO$_2$, 0-10% EtOAc/hexanes) gave the title compound (833 mg, 52%) as a clear liquid. $^1$H NMR (400 MHz, CDCl$_3$): δ 7.15 (d, J=8.7 Hz, 2 H); 6.95-6.88 (m, 2 H); 4.29 (m, 2 H); 3.64 (t, J=6.29 Hz, 2H).

Intermediate B2: 2-(4-Tert-butoxyphenoxy)ethanol

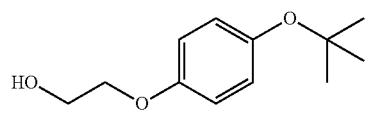

Step 1: [2-(4-Tert-butoxyphenoxy)ethoxy](tert-butyl) dimethylsilane

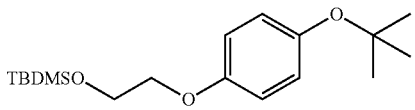 [SMILES: CC(C)(C)Oc1ccc(OCCO[Si](C)(C)C(C)(C)C)cc1]

4-Tert-butoxyphenol (1 g, 6.02 mmole), 2-(t-butyldimethylsiloxy)ethanol (1.38 g, 7.83 mmole), and PPh$_3$ (2.05 g, 7.82 mmole) were combined in toluene (30 mL) at RT. To this was added DIAD (1.52 mL, 7.82 mmole) slowly at RT. After stirring overnight the mixture was concentrated. Flash column chromatography (Biotage-SNAP-50 g SiO$_2$, 0-10% EtOAc/hexanes) gave the title compound (1.7 g, 87%) as a clear oil. $^1$H NMR (400 MHz, CDCl$_3$): δ 6.90 (d, J=8.8 Hz, 2 H); 6.80 (d, J=8.8 Hz, 2 H); 4.03-3.92 (m, 4 H); 1.30 (s, 9 H); 0.91 (s, 9 H); 0.10 (s, 6H).

Step 2: 2-(4-Tert-butoxyphenoxy)ethanol

[2-(4-Tert-butoxyphenoxy)ethoxy](tert-butyl)dimethylsilane (1.7 g, 5.24 mmole) was taken up in 2-MeTHF (10 mL). To this was added 1M TBAF (16 mL, 16.00 mmole) in THF then the mixture was heated to 60° C. After 4 hr the mixture was cooled to RT and concentrated. The residue was taken up in H$_2$O and extracted with CH$_2$Cl$_2$ (3×). The combined organic layers were dried (MgSO$_4$), filtered, and concentrated. Flash column chromatography (Biotage-SNAP-50 g SiO$_2$, 30% EtOAc/hexanes) gave the title compound (1.02 g, 93%) as a clear oil. $^1$H NMR (400 MHz, CDCl$_3$): δ 6.94-6.90 (m, 2 H); 6.83-6.79 (m, 2 H); 4.07-4.02 (m, 2 H); 3.97-3.91 (m, 2 H); 1.30 (s, 9 H).

Intermediate B3: (5-Phenyl-1-{[2-(trimethylsilyl)ethoxy]methyl}-1H-pyrazol-3-yl)methanol

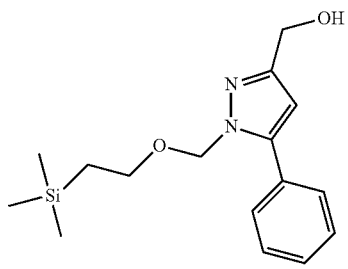 [SMILES: C[Si](C)(C)CCOCn1nc(CO)cc1-c1ccccc1]

To a solution of 5-phenyl-1H-pyrazole-3-carboxylic acid methyl ester (250 mg, 1.236 mmole) in THF (5 mL) was added NaH (60% dispersion in mineral oil, 60 mg, 1.500 mmole) portionwise at RT. After gas evolution had ceased SEMCl (0.263 mL, 1.484 mmol) was added. After stirring overnight the mixture was diluted with EtOAc, filtered through a pad of Celite washing with EtOAc, and concentrated. Flash column (Biotage-SNAP-25 g SiO$_2$, 0-20% EtOAc/hexanes) gave methyl 5-phenyl-1-{[2-(trimethylsilyl)ethoxy]methyl}-1H-pyrazole-3-carboxylate (380 mg, 92%) as a clear oil. $^1$H NMR (399 MHz, CDCl$_3$): δ 7.64 (dd, J=7.3, 1.9 Hz, 3 H); 7.46 (d, J=7.4 Hz, 3 H); 6.94 (s, 1 H); 5.49 (s, 2 H); 3.96 (s, 3 H); 3.80-3.71 (m, 3 H); 0.97-0.88 (m, 2 H); 0.02 (s, 9H).

To a solution of methyl 5-phenyl-1-{[2-(trimethylsilyl)ethoxy]methyl}-1H-pyrazole-3-carboxylate (380 mg, 1.143 mmole) in THF (5 mL) was added 2M LiBH$_4$ in THF (0.9 mL, 1.800 mmole) at RT. After 30 min the mixture was heated to reflux. After 45 min the mixture was cooled to RT and quenched by slow addition of 1M NaOH. The mixture was diluted with H$_2$O and extracted with CH$_2$Cl$_2$ (3×). The combined organic layers were dried (MgSO$_4$), filtered through a pad of Celite washing with CH$_2$Cl$_2$, and concentrated to give the title compound (327 mg, 94%) as a clear oil. $^1$H NMR (399 MHz, CDCl$_3$): δ 7.60 (dd, J=7.4, 1.5 Hz, 2 H); 7.48-7.40 (m, 3 H); 6.40 (s, 1 H); 5.38 (s, 2 H); 4.74 (d, J=5.8 Hz, 2 H); 3.76-3.67 (m, 2 H); 2.03-1.96 (m, 1 H); 0.98-0.89 (m, 2 H); 0.01 (s, 9 H).

Intermediate B4: {2-[4-(Trifluoromethoxy)phenyl]-1,3-thiazol-4-yl}methanol

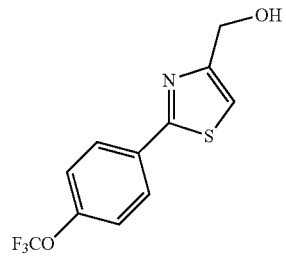 [SMILES: OCc1csc(-c2ccc(OC(F)(F)F)cc2)n1]

Ethyl 2-bromothiazole-4-carboxylate (100 mg, 0.424 mmole), 4-(trifluoromethoxy)phenylboronic acid (113 mg, 0.551 mmole), CsF (129 mg, 0.847 mmole), and bis(tri-t-butylphosphine)palladium(0) (22 mg, 0.043 mmole) were combined in a screw cap vial. To this was added 1,4-dioxane (2 mL). N$_2$ was bubbled through the mixture for 10 seconds. The vial was capped then heated to 100° C. After 6 hr the mixture was cooled to RT, diluted with EtOAc, filtered through a pad of Celite washing with EtOAc, and concentrated. Flash column chromatography (Biotage-SNAP-25 g SiO$_2$, 0-15% EtOAc/hexanes) gave ethyl 2-[4-(trifluoromethoxy)phenyl]-1,3-thiazole-4-carboxylate (71 mg, 53%) as a pale orange solid. $^1$H NMR (399 MHz, CDCl$_3$): δ 8.18 (s, 1 H); 8.07-8.03 (m, 2 H); 7.30 (d, J=8.4 Hz, 2 H); 4.46 (q, J=7.1 Hz, 2 H); 1.44 (t, J=7.1 Hz, 3 H).

To a solution of ethyl 2-[4-(trifluoromethoxy)phenyl]-1,3-thiazole-4-carboxylate (71 mg, 0.224 mmol) in 2-MeTHF (1 mL) was added 2M LiBH$_4$ (0.224 mL, 0.448 mmol) in THF slowly at RT. After 90 min the mixture was quenched by the addition of 2M NaOH (0.6 mL, 1.200 mmole). The mixture was stirred for 4 hr then diluted with EtOAc, filtered through a pad of Celite and concentrated to give the title compound (60 mg, 97%). $^1$H NMR (400 MHz, CDCl$_3$): δ 8.00-7.96 (m, 2 H); 7.31-7.25 (m, 2 H); 7.21 (s, 1 H); 4.84 (d, J=5.6 Hz, 2 H); 2.29-2.22 (m, 1 H).

Intermediate B5: {2-[4-(Trifluoromethoxy)phenyl]-1,3-oxazol-4-yl}methanol

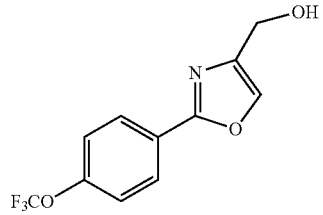 [SMILES: OCc1coc(-c2ccc(OC(F)(F)F)cc2)n1]

The title compound was made in a similar manner to {2-[4-(trifluoromethoxy)phenyl]-1,3-thiazol-4-yl}methanol.

Intermediate B6: 2-(Quinolin-5-yloxy)ethanol

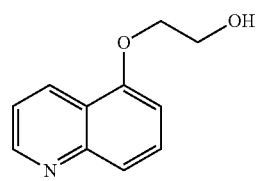 [SMILES: OCCOc1cccc2ncccc12]

Quinolin-5-ol (100 mg, 0.689 mmole) and PPh₃ (235 mg, 0.896 mmole) were taken up in toluene (3 mL). To this was added 2-tert-butoxyethanol (0.118 mL, 0.896 mmole) then DIAD (0.174 mL, 0.896 mmole) at RT. After stirring overnight the mixture was concentrated. Flash column chromatography (Biotage-SNAP-10 g SiO₂, 0-50% EtOAc/hexanes) gave a clear oil which was sufficiently pure for use in the next step.

The impure material from above was taken up in 3 mL TFA. After 4 hr the mixture was concentrated. The residue was taken up in MeOH then passed through Dowex 1×2-400 ion exchange resin (prewashed with 1M NaOH, H₂O, MeOH) washing with MeOH. The filtrate was concentrated. Flash column chromatography (Biotage-SNAP-10 g SiO₂, 0-100% EtOAc/hexanes) gave the title compound (108 mg, 83%) as a white solid. ¹H NMR (400 MHz, CDCl₃): δ 8.92 (dd, J=4.2, 1.7 Hz, 1 H); 8.60 (dd, J=8.5, 1.6 Hz, 1 H); 7.73 (d, J=8.6 Hz, 1H); 7.61 (t, J=8.1 Hz, 1 H); 7.39 (dd, J=8.5, 4.2 Hz, 1 H); 6.90 (d, J=7.7 Hz, 1 H); 4.30 (t, J=4.5 Hz, 2 H); 4.13 (bs, 2 H); 2.07 (s, 1 H).

Intermediate B7: 2-(Isoquinolin-5-yloxy)ethanol

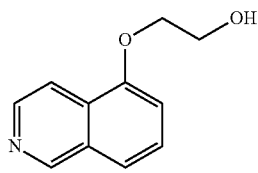 [SMILES: OCCOc1cccc2cnccc12]

The title compound was made in a similar manner to 2-(quinolin-5-yloxy)ethanol.

Intermediate B8: 2-(Isoquinolin-8-yloxy)ethanol

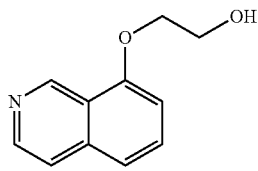 [SMILES: OCCOc1cccc2ccncc12]

The title compound was made in a similar manner to 2-(quinolin-5-yloxy)ethanol.

Intermediate B9: 4-(Tetrahydro-2H-pyran-4-yloxy)phenol

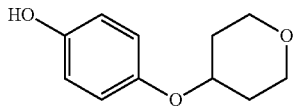

4-Tert-butoxyphenol (200 mg, 1.203 mmole) and PPh₃ (410 mg, 1.564 mmole) were combined in toluene (5 mL). To this was added tetrahydro-2H-pyran-4-ol (0.149 mL, 1.564 mmole). DIAD (0.304 mL, 1.564 mmole) was added dropwise at RT. After stirring overnight the mixture was concentrated. Flash column chromatography (Biotage-SNAP-25 g SiO₂, 10% EtOAc/hexanes) gave 4-(4-tert-butoxyphenoxy)tetrahydro-2H-pyran (257 mg, 85%) as a clear oil. ¹H NMR (400 MHz, CDCl₃): 06.90 (d, J=8.9 Hz, 2 H); 6.83-6.79 (m, 2 H); 4.39 (m, 1 H); 4.03-3.95 (m, 2 H); 3.56 (m, 2 H); 2.04-1.96 (m, 2 H); 1.83-1.72 (m, 2 H); 1.30 (s, 9 H).

4-(4-Tert-butoxyphenoxy)tetrahydro-2H-pyran (257 mg, 1.027 mmole) was taken up in TFA (5 mL) at RT. After 90 min the mixture was concentrated. The residue was taken up in saturated aqueous NaHCO₃ and extracted with CH₂Cl₂ (3×). The combined organic layers were dried (MgSO₄), filtered, and concentrated to give the title compound (188 mg, 94%) as an off-white solid. ¹H NMR (400 MHz, CDCl₃): δ 6.82 (m, 2 H); 6.77-6.73 (m, 2 H); 4.71 (s, 1 H); 4.37-4.29 (m, 1 H); 4.03-3.95 (m, 2 H); 3.55 (m, 2 H); 2.03-1.95 (m, 2 H); 1.81-1.70 (m, 2 H).

Intermediate B 10: 4-(Tetrahydrofuran-3-yloxy)phenol

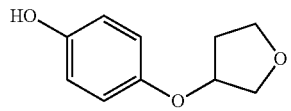

The title compound was made in a similar manner to 4-(tetrahydro-2H-pyran-4-yloxy)phenol.

Intermediate B 11: 2-[4-(trifluoromethoxy)phenoxy]ethanol

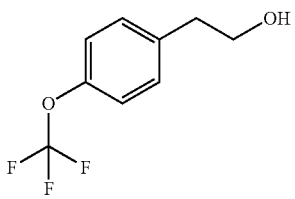 [SMILES: OCCc1ccc(OC(F)(F)F)cc1]

4-trifluoromethoxyphenol (8.9 g, 50.2 mmol) was dissolved in DMF and treated with (2-bromoethoxy)(tert-butyl)dimethylsilane (16.81 g, 70.3 mmol) followed by Cs₂CO₃ (17.99 g, 55.2 mmol). The reaction mixture was heated to 60° C. for 3 hrs. The reaction was quenched with water and hexane was added. The two layers were separated, and the aqueous phase was further extracted twice with hexane. The combined organic layers were washed with brine, dried (Na₂SO₄), filtered and concentrated in vacuo. The resulting residue was used without further purification. The residue was dissolved in acetonitrile (100 mL) and treated with triethylamine trihydrofluoride (20.23 g, 125 mmol) the mixture was left to stir at RT for 3 hrs. TLC (10% EtOAc in hexane) showed the reaction was complete. Quenched with water (150 mL) and added ether (1000 mL). The organic layer was washed with brine, dried (Na₂SO₄) filtered and concentrated in vacuo. The residue was purified by silica gel chromatography. The eluting solvent was 0-20% EtOAc in hexanes. 9.7 g of the title product was isolated.

Intermediate B 12: 4-(2-chloroethyl)phenyl trifluoromethyl ether

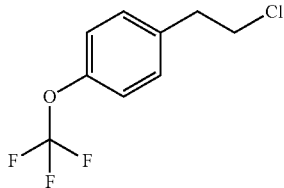 [SMILES: FC(F)(F)Oc1ccc(CCCl)cc1]

Synthesis of Intermediates C

Intermediate C1: N-Pronyl-4-(tributylstannanyl)pyridin-2-amine

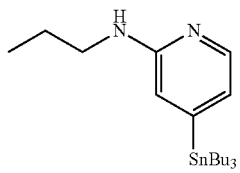

2-Fluoro-4-(tributylstannyl)pyridine (150 mg, 0.388 mmole) was taken up in MeOH (1 mL) in a microwave vessel. To this was added N-propylamine (0.162 mL, 1.942 mmole). The vessel was sealed then heated to 150° C. by microwave irradiation for 90 min. 0.45 mL N-propylamine was added. The mixture was heated to 150° C. for 3 hr then concentrated. Flash column chromatography (Biotage-SNAP-25 g SiO$_2$, 0-30% EtOAc/hexanes) gave the title compound (58 mg, 35%) as a clear oil. $^1$H NMR (400 MHz, CDCl$_3$): $\delta$57.97 (d, J=4.9 Hz, 1 H); 6.62 (d, J=4.8 Hz, 1 H); 6.47 (s, 1 H); 4.35 (s, 1 H); 3.23 (q, J=6.6 Hz, 2 H); 1.68-1.45 (m, 8 H); 1.38-1.28 (m, 6 H); 1.09-0.95 (m, 9 H); 0.89 (m, 9 H).

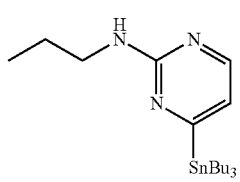

Intermediate C2: N-Propyl-4-(tributylstannanyl)pyrimidin-2-amine

To a solution of 2-(methylthio)-4-(tributylstannyl)pyrimidine (250 mg, 0.602 mmole) in CH$_2$Cl$_2$ (3 mL) was added m-CPBA (371 mg, 1.505 mmole) at RT. After 2 hr the mixture was concentrated. Flash column chromatography (Biotage-SNAP-25 g SiO$_2$, 0-25% EtOAc/hexanes) gave mixed fractions. Fractions containing the product were pooled and concentrated. The residue was taken up in MeOH. The mixture was passed through Dowex 1×2-400 ion exchange resin (prewashed with 1M NaOH, H$_2$O, MeOH) washing with MeOH. The filtrate was concentrated to give a 2:1 mixture of 2-methoxy:2-methylsulphone.

The above mixture was taken up in 2 mL 2-MeTHF. To this was added 0.15 mL N-propylamine. After stirring overnight the mixture was concentrated. Flash column chromatography (Biotage-SNAP-10 g SiO$_2$, 0-20% EtOAc/hexanes) gave the title compound (39 mg, 25%) as a clear oil. $^1$H NMR (400 MHz, CDCl$_3$): $\delta$8.02 (d, J=4.7 Hz, 1 H); 6.62 (d, J=4.7 Hz, 1 H); 4.97 (s, 1 H); 3.37 (q, J=6.8 Hz, 2 H); 1.66-1.49 (m, 8 H); 1.38-1.28 (m, 8 H); 1.12-1.03 (m, 6 H); 1.01-0.92 (m, 4 H); 0.93-0.84 (m, 12 H).

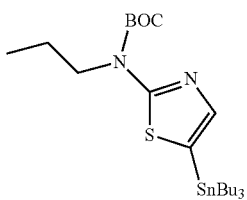

Intermediate C3: Tert-butyl propyl[5-(tributylstannanyl)-1,3-thiazol-2-yl]carbamate To a solution of 2-(N-BOC)-5-(tributylstannyl)thiazole (200 mg, 0.409 mmole) in DMF (2 mL) was added NaH (60% dispersion in mineral oil, 20 mg, 0.500 mmole) at RT. After gas evolution had ceased 1-iodopropane (0.048 mL, 0.490 mmole) was added and the mixture was heated to 60° C. After stirring overnight the mixture was cooled to RT, diluted with H$_2$O, and extracted with EtOAc (3×). The combined organic layers were washed with H$_2$O and brine, dried (MgSO$_4$), filtered, and concentrated. Flash column chromatography (Biotage-SNAP-25 g SiO$_2$, 0-10% EtOAc/hexanes) gave the title compound (155 mg, 71%) as a clear oil. $^1$H NMR (400 MHz, CDCl$_3$): $\delta$ 7.33 (s, 1 H); 4.11-4.03 (m, 2 H); 1.79-1.69 (m, 1 H); 1.62-1.52 (m, 18 H); 1.38-1.28 (m, 7 H); 1.13-1.05 (m, 7 H); 0.95 (m, 3 H); 0.93-0.84 (m, 9 H).

Synthesis of Intermediates D

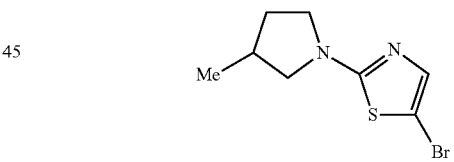

Intermediate D1: 5-Bromo-2-(3-methylpyrrolidin-1-yl)-1,3-thiazole 2,5-Dibromothiazole (250 mg, 1.029 mmole), 3-methylpyrrolidine hydrochloride (188 mg, 1.544 mmole), and K$_2$CO$_3$ (569 mg, 4.12 mmole) were combined in DMF (5 mL) then heated to 100° C. After stirring overnight the mixture was cooled to RT, diluted with H$_2$O and extracted with EtOAc (3×). The combined organic layers were washed with H$_2$O and brine, dried (MgSO$_4$), filtered, and concentrated. Flash column chromatography (Biotage-SNAP-10 g SiO$_2$, 0-50% EtOAc/hexanes) gave the title compound (234 mg, 92%) as a pale yellow oil. $^1$H NMR (399 MHz, CDCl$_3$): $\delta$ 7.06 (s, 1 H); 3.58-3.45 (m, 2 H); 3.45-3.35 (m, 1 H); 2.97 (dd, J=9.7, 7.7 Hz, 1 H); 2.47-2.36 (m, 1 H); 2.20-2.10 (m, 1 H); 1.73-1.63 (m, 1 H); 1.12 (d, J=6.7 Hz, 3H).

EXAMPLES

Example 1

4-(3-Methoxyphenyl)-1-(3-phenylpropyl)-1H-pyrrolo[3,2-c]pyridine-2-carboxylic acid

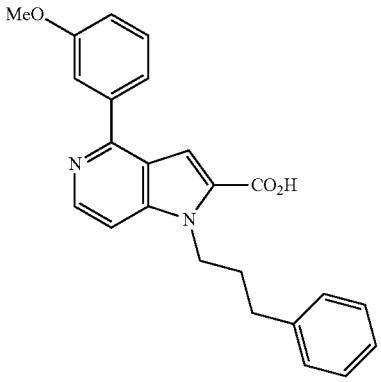 [SMILES: COc1cccc(-c2nccc3c2cc(C(=O)O)n3CCCc2ccccc2)c1]

Step 1: Methyl 4-(3-methoxyphenyl)-1H-pyrrolo[3,2-c]pyridine-2-carboxylate

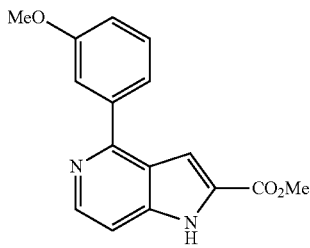 [SMILES: COC(=O)c1cc2c(-c3cccc(OC)c3)nccc2[nH]1]

Intermediate A1, Methyl 4-chloro-1H-pyrrolo[3,2-c]pyridine-2-carboxylate (500 mg, 2.374 mmole), 3-methoxyphenylboronic acid (469 mg, 3.09 mmole), Pd(OAc)$_2$ (32.0 mg, 0.142 mmole), X-Phos (113 mg, 0.237 mmole), and KF (414 mg, 7.12 mmole) were combined in 1,4-dioxane (10 mL). The mixture was degassed (3× pump/N$_2$) then heated to 100° C. After 2 hr the mixture was cooled to RT, diluted with EtOAc, filtered through a pad of Celite washing with EtOAc, and concentrated. Flash column (Biotage-SNAP-50 g SiO$_2$, 50% EtOAc/hexanes) gave the title compound (574 mg, 86%) as an off-white solid. $^1$H NMR (399 MHz, CDCl$_3$): δ 9.26 (bs, 1 H); 8.51 (d, J=5.8 Hz, 1 H); 7.58-7.51 (m, 3 H); 7.50-7.40 (m, 1 H); 7.30 (d, J=5.9 Hz, 1 H); 7.03 (dd, J=8.2, 2.6 Hz, 1 H); 3.97 (s, 3 H); 3.91 (s, 3 H).

Step 2: Methyl 4-(3-methoxyphenyl)-1-(3-phenylpropyl)-1H-pyrrolo[3,2-c]pyridine-2-carboxylate

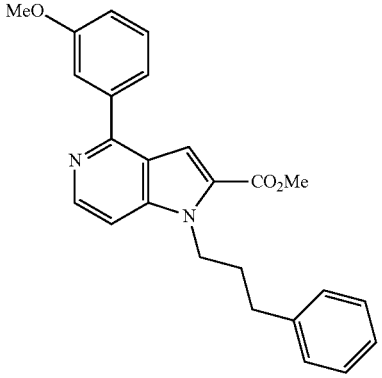 [SMILES: COC(=O)c1cc2c(-c3cccc(OC)c3)nccc2n1CCCc1ccccc1]

Methyl 4-(3-methoxyphenyl)-1H-pyrrolo[3,2-c]pyridine-2-carboxylate (50 mg, 0.177 mmole) and K$_2$CO$_3$ (49.0 mg, 0.354 mmole) were combined in a screw cap vial. To this was added 1,4-dioxane (0.75 mL) and 1-bromo-3-phenylpropane (0.035 mL, 0.230 mmole). The vial was capped then heated to 100° C. After stirring overnight the mixture was cooled to RT and diluted with EtOAc. The mixture was filtered through Celite washing with EtOAc. The filtrate was concentrated. Flash column (Biotage-SNAP-10 g SiO$_2$, 30% EtOAc/hexanes) gave the title compound (68 mg, 96%) as a pale yellow oil. $^1$H NMR (399 MHz, CDCl$_3$): δ 8.46 (d, J=6.0 Hz, 1 H); 7.58 (d, J=1.0 Hz, 1 H); 7.55-7.50 (m, 2 H); 7.48-7.39 (m, 1 H); 7.32-7.27 (m, 2H); 7.23-7.17 (m, 3 H); 7.09 (dd, J=6.0, 1.0 Hz, 1 H); 7.02 (ddd, J=8.2, 2.7, 1.1 Hz, 1 H); 4.65-4.57 (m, 2 H); 3.91 (m, 6 H); 2.76-2.68 (m, 2 H); 2.21-2.13 (m, 2 H).

Step 3: 4-(3-Methoxyphenyl)-1-(3-phenylpropyl)-1H-pyrrolo[3,2-c]pyridine-2-carboxylic acid Methyl 4-(3-methoxyphenyl)-1-(3-phenylpropyl)-1H-pyrrolo[3,2-c]pyridine-2-carboxylate (68 mg, 0.170 mmole) was taken up in MeOH (0.5 mL). To this was added 2M NaOH (0.255 mL, 0.509 mmole) at RT. The reaction mixture immediately became cloudy. 1,4-Dioxane (0.500 mL) was added to aid solubility. After 90 min 2M NaOH (0.255 mL, 0.509 mmole) was added and stirring was continued. After 90 min the mixture was concentrated. The crude material was taken up in DMSO and acidified with TFA. The resulting solution was purified directly by preparative reversed-phase HPLC (30×100 mm Phenomenex AXIA-Gemini-NX, 10%-35% CH$_3$CN/water containing 0.1% TFA over 18 min at 50 mL/min) to give the TFA salt of the title compound (67 mg, 79%) as a white foam. $^1$H NMR (399 MHz, CDCl$_3$): δ 8.27 (d, J=6.8 Hz, 1H); 7.49 (s, 1 H); 7.44-7.35 (m, 1 H); 7.35-7.15 (m, 5 H); 7.12-7.01 (m, 4 H); 4.31-4.24 (m, 2H); 3.92 (s, 3 H); 2.64-2.55 (m, 2 H); 1.98-1.89 (m, 2 H). HRMS (ESI) calc (M+H)$^+$=387.1703. found 387.1701.

Example 2

4-(3-Methoxyphenyl)-1-[0E)-3-phenylprop-2-en-1-yl]-1H-pyrrolo[3,2-c]pyridine-2-carboxylic acid

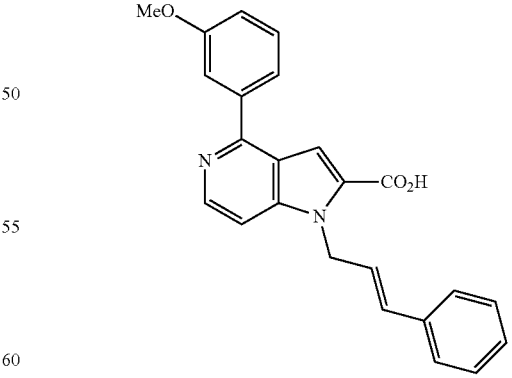

The TFA salt of the title compound (43 mg, 75%) was synthesized according to the procedures described in Example 1 to give a white foam. $^1$H NMR (399 MHz, CDCl$_3$); δ 8.44 (d, J=6.8 Hz, 1 H); 7.50 (m, 2 H); 7.44 (t, J=8.0 Hz, 1 H); 7.39-7.21 (m, 7 H); 7.19 (d, J=8.3 Hz, 1H); 6.44 (d, J=15.8

Hz, 1 H); 6.22-6.12 (m, 1 H); 5.18 (d, J=6.4 Hz, 2 H); 3.91 (s, 2 H). HRMS (ESI) calc (M+H)⁺=385.1547. found 385.1547.

Example 3

4-(3-Methoxyphenyl)-1-[2-oxo-2-(phenylamino) ethyl]-1H-pyrrolo[3,2-c]pyridine-2-carboxylic acid

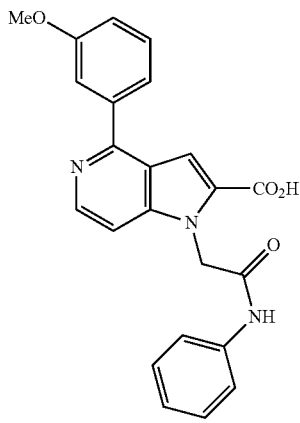 [SMILES: COc1cccc(-c2nccc3c2cc(C(=O)O)n3CC(=O)Nc2ccccc2)c1]

Step 1: Methyl 1-(2-tert-butoxy-2-oxoethyl)-4-(3-methoxyphenyl)-1H-pyrrolo[3,2-c]pyridine-2-carboxylate

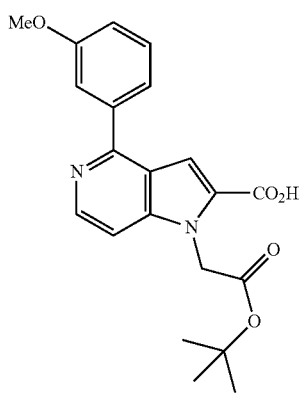 [SMILES: COc1cccc(-c2nccc3c2cc(C(=O)O)n3CC(=O)OC(C)(C)C)c1]

The title compound (45 mg, 32%) was synthesized according to the procedures described in Example 1 steps 1 and 2 to give an amber foam. ¹H NMR (399 MHz, CDCl₃): δ 8.52 (dd, J=6.0, 3.3 Hz, 1 H); 7.63 (s, 1 H); 7.59-7.48 (m, 2 H); 7.49-7.41 (m, 1 H); 7.17 (d, J=6.0 Hz, 1H); 7.03 (dd, J=8.2, 2.5 Hz, 1 H); 5.23 (s, 2 H); 3.91 (s, 6 H); 1.47 (s, 9 H).

Step 2: 4-(3-Methoxyphenyl)-1-[2-oxo-2-(phenylamino)ethyl]-1H-pyrrolo[3,2-c]pyridine-2-carboxylic acid To a solution of methyl 1-(2-tert-butoxy-2-oxoethyl)-4-(3-methoxyphenyl)-1H-pyrrolo[3,2-c]pyridine-2-carboxylate (45 mg, 0.114 mmole) in CH₂Cl₂ (0.5 mL) was added TFA (0.5 mL, 6.49 mmole) at RT. After 2 hr the mixture was concentrated. The residue was used directly in the next step without purification.

To a solution of the above material (25.9 mg, 0.057 mmole) in DMF (0.5 mL) was added TEA (24 μL, 0.172 mmole), aniline (8 μL, 0.088 mmole), then HATU (32.5 mg, 0.086 mmole) at RT. After stirring overnight the mixture was filtered using a 0.45 pin PTFE syringe filter then purified by preparative reversed-phase HPLC (21×100 mm Phenomenex AXIA-Gemini-NX, 10%-35% CH₃CN/water containing 0.1% TFA over 18 min at 20 mL/min) to give methyl 4-(3-methoxyphenyl)-1-[2-oxo-2-(phenylamino)ethyl]-1H-pyrrolo[3,2-c]pyridine-2-carboxylate a white solid (22 mg, 73%). ¹H NMR (399 MHz, DMSO): δ 10.55 (s, 1 H); 8.63 (d, J=6.7 Hz, 1H); 8.24 (d, J=6.6 Hz, 1 H); 7.71 (s, 1 H); 7.67-7.50 (m, 5 H); 7.36-7.27 (m, 3 H); 7.08 (t, J=7.4 Hz, 1 H); 5.64 (s, 2 H); 3.90 (s, 3 H); 3.88 (s, 3 H).

Methyl 4-(3-methoxyphenyl)-1-[2-oxo-2-(phenylamino)ethyl]-1H-pyrrolo[3,2-c]pyridine-2-carboxylate (22 mg, 0.042 mmole) was taken up in 1,4-dioxane (0.5 mL). To this was added 2M NaOH (0.104 mL, 0.208 mmole) at RT. After stirring overnight the mixture was concentrated. The crude material was taken up in DMSO and acidified with TFA. The resulting solution was purified by preparative reversed-phase HPLC (21×100 mm Phenomenex AXIA-Gemini-NX, 5%-30% CH₃CN/water containing 0.1% TFA over 18 min at 20 mL/min) to give the TFA salt of the title compound (10 mg, 47%) as a white solid. ¹H NMR (399 MHz, DMSO): δ 10.49 (s, 1 H); 8.59 (d, J=6.5 Hz, 1 H); 8.16 (bs, 1 H); 7.64-7.55 (m, 5 H); 7.53 (s, 1 H); 7.35-7.24 (m, 3 H); 7.10-7.04 (m, 1 H); 5.63 (s, 2 H); 3.90 (s, 3 H). HRMS (ESI) calc (M+H)⁺= 402.1448. found 402.1453.

Example 4

1-[2-(Benzylamino)-2-oxoethyl]-4-(3-methoxyphenyl)-1H-pyrrolo[3,2-c]pyridine-2-carboxylic acid

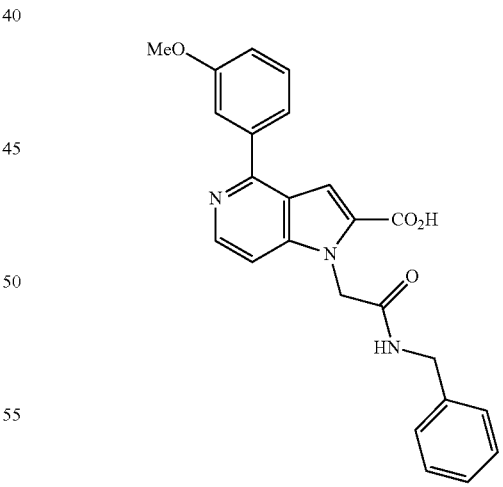

The TFA salt of the title compound (14 mg, 72%) was synthesized according to the procedures described in Example 3 to give a white solid. ¹H NMR (399 MHz, DMSO): δ 9.50-9.43 (m, 1H); 8.58 (d, J=6.7 Hz, 1 H); 8.21 (bs, 1 H); 7.86 (s, 1 H); 7.69-7.59 (m, 1 H); 7.58-7.52 (m, 2H); 7.34-7.31 (m, 3 H); 5.55 (s, 2 H); 4.49 (d, J=5.9 Hz, 2 H); 3.90 (s, 3 H). HRMS (ESI) calc (M+H)⁺=416.1605. found 416.1609.

Example 5

4-(3-Methoxyphenyl)-1-(3-phenylprop-2-yn-1-yl)-1H-pyrrolo[3,2-c]pyridine-2-carboxylic acid

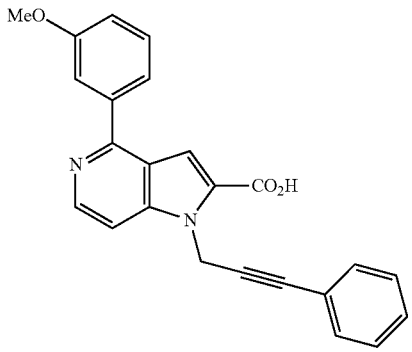 [SMILES: COc1cccc(-c2nccc3c2cc(C(=O)O)n3CC#Cc2ccccc2)c1]

Methyl 4-(3-methoxyphenyl)-1H-pyrrolo[3,2-c]pyridine-2-carboxylate (57 mg, 0.202 mmole), 3-phenyl-2-propyn-1-ol (38 µl, 0.305 mmole), and (triphenylphosphoranylidene)acetonitrile (91 mg, 0.303 mmole) were combined in toluene (1 mL) in a screw cap vial. The vial was capped then heated to 110° C. After stirring overnight the mixture was cooled to RT. 3-Phenyl-2-propyn-1-ol (38 µl, 0.305 mmole), and (triphenylphosphoranylidene)acetonitrile (91 mg, 0.303 mmole) were added then the mixture was heated to 110° C. After stirring overnight the mixture was cooled to RT and concentrated. The crude material was purified by preparative reversed-phase HPLC (30×100 mm Phenomenex AXIA-Gemini-NX, gradient 5%-55% CH$_3$CN/water containing 0.1% TFA over 18 min at 50 mL/min) to a mixture of product and PPh$_3$. This mixture was taken up in 1,4-dioxane (1 mL). To this was added 2M NaOH (0.505 mL, 1.010 mmole) at RT. After stirring overnight the mixture was concentrated. The crude material was taken up in DMSO and acidified with TFA (0.2 mL). The resulting solution was purified by preparative reversed-phase HPLC (30×100 mm Phenomenex AXIA-Gemini-NX, 10%-35% CH$_3$CN/water containing 0.1% TFA over 18 min at 50 mL/min) to give the TFA salt of the title compound (37 mg, 37%) as a pale yellow solid. $^1$H NMR (399 MHz, DMSO): δ 8.66 (d, J=6.6 Hz, 1 H); 8.26 (d, J=6.6 Hz, 1 H); 7.68-7.50 (m, 4 H); 7.42-7.32 (m, 5 H); 7.28 (d, J=8.2 Hz, 1 H); 5.92 (s, 2 H); 3.89 (s, 3 H). FIRMS (ESI) calc (M+H)$^+$=383.1390. found 383.1386.

Example 6

4-(3-Ethoxyphenyl)-1-(2-phenoxyethyl)-1H-pyrrolo[3,2-c]pyridine-2-carboxylic acid

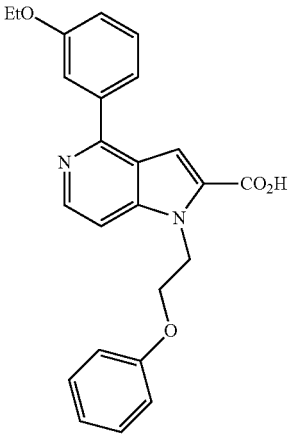 [SMILES: CCOc1cccc(-c2nccc3c2cc(C(=O)O)n3CCOc2ccccc2)c1]

Step 1: Methyl 4-(3-ethoxyphenyl)-1H-pyrrolo[3,2-c]pyridine-2-carboxylate

Methyl 4-chloro-1H-pyrrolo[3,2-c]pyridine-2-carboxylate (1 g, 4.75 mmole), 3-ethoxyphenylboronic acid (1.03 g, 6.21 mmole), Pd(OAc)$_2$ (0.064 g, 0.285 mmole), X-Phos (0.226 g, 0.475 mmole), and potassium fluoride (0.828 g, 14.24 mmole) were combined in 1,4-dioxane (20 mL). The mixture was degassed (3× pump/N$_2$) then heated to 100° C. After 4 hr the mixture was cooled to RT and diluted with EtOAc, filtered through a pad of Celite washing with EtOAc, and concentrated. Flash column (Biotage-SNAP-50 g SiO$_2$, 50% EtOAc/hexanes) gave the title compound (1.02 g, 72.5%) as a pale yellow solid. $^1$H NMR (400 MHz, CDCl$_3$): δ 9.20 (bs, 1 H); 8.51 (d, J=5.8 Hz, 1 H); 7.54-7.49 (m, 3 H); 7.47-7.38 (m, 1 H); 7.29 (d, J=5.9 Hz, 1 H); 7.04-7.00 (m, 1 H); 4.14 (q, J=6.83 Hz, 2 H); 3.97 (s, 3 H); 1.45 (t, J=7.12 Hz, 3 H).

Step 2: 4-(3-Ethoxyphenyl)-1-(2-phenoxyethyl)-1H-pyrrolo[3,2-c]pyridine-2-carboxylic acid To a solution of methyl 4-(3-ethoxyphenyl)-1H-pyrrolo[3,2-c]pyridine-2-carboxylate (30 mg, 0.101 mmole) in DMF (0.5 mL) was added NaH (60% dispersion in mineral oil, 5.5 mg, 0.138 mmole) at RT. After gas evolution had ceased 2-bromoethyl phenyl ether (27 mg, 0.134 mmole) was added all at once as a solid. After stirring overnight 2M NaOH (200 µL, 0.400 mmole) was added and stirring continued at RT. After 4 hr the mixture was concentrated. The crude material was taken up in DMSO and acidified with TFA. The resulting solution was purified by preparative reversed-phase HPLC (30×100 mm Phenomenex AXIA-Gemini-NX, 15%-40% CH$_3$CN/water containing 0.1% TFA over 18 min at 50 mL/min) to give the TFA salt of the title compound (39 mg, 75%) as a pale yellow solid. $^1$H NMR (499 MHz, DMSO): δ 8.59 (d, J=6.6 Hz, 1 H); 8.17 (s, 1 H); 7.60-7.56 (m, 2 H); 7.52 (m, 1 H); 7.48 (m, 1 H); 7.27-7.19 (m, 3 H); 6.92-6.87 (m, 1 H); 6.81 (d, J=8.1 Hz, 2 H); 5.16 (m, 2 H); 4.37 (m, 2 H); 4.16 (q, J=6.94 Hz, 2 H); 1.38 (t, J=6.62 Hz, 3 H). HRMS (ESI) calc (M+H)$^+$=403.1652. found 403.1656.

The following compounds were synthesized according to the procedures described in Example 6 using the appropriate boronic acid in step 1 and alkyl halide in step 2 and were isolated as their TFA salt.

| Ex | Structure | Name | Obs. HRMS (M + H)+ |
|---|---|---|---|
| 7 | 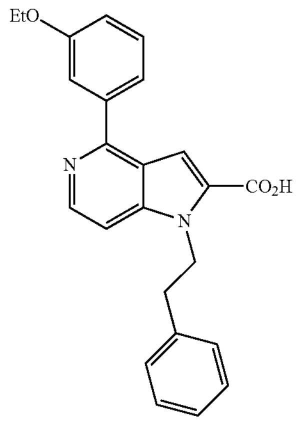 [SMILES: CCOc1cccc(-c2nccc3c2cc(C(=O)O)n3CCc2ccccc2)c1] | 4-(3-ethoxyphenyl)-1-(2-phenylethyl)-1H-pyrrolo[3,2-c]pyridine-2-carboxylic acid | 387.1699 |
| 8 | 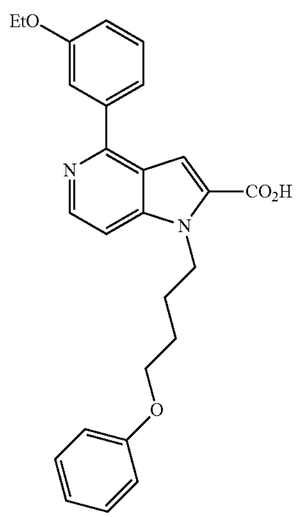 [SMILES: CCOc1cccc(-c2nccc3c2cc(C(=O)O)n3CCCCOc2ccccc2)c1] | 4-(3-ethoxyphenyl)-1-(3-phenoxypropyl)-1H-pyrrolo[3,2-c]pyridine-2-carboxylic acid | 417.1805 |
| 9 | 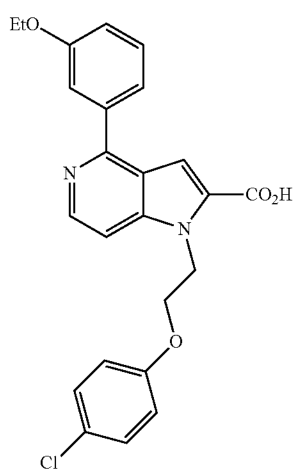 [SMILES: CCOc1cccc(-c2nccc3c2cc(C(=O)O)n3CCOc2ccc(Cl)cc2)c1] | 1-[2-(4-chlorophenoxy)ethyl]-4-(3-ethoxyphenyl)-1H-pyrrolo[3,2-c]pyridine-2-carboxylic acid | 437.1262 |

-continued

| Ex | Structure | Name | Obs. HRMS (M + H)+ |
|---|---|---|---|
| 10 | 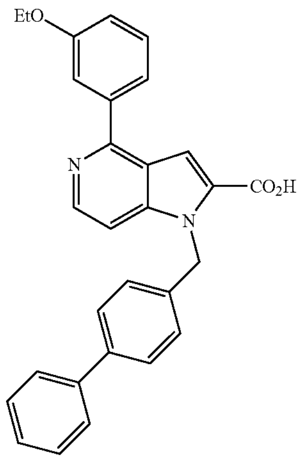 [SMILES: CCOc1cccc(-c2nccc3c2cc(C(=O)O)n3Cc2ccc(-c3ccccc3)cc2)c1] | 1-(biphenyl-4-ylmethyl)-4-(3-ethoxyphenyl)-1H-pyrrolo[3,2-c]pyridine-2-carboxylic acid | 449.1861 |
| 11 | 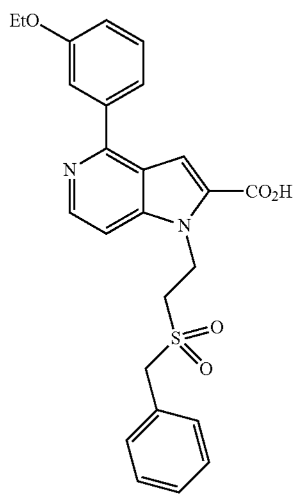 [SMILES: CCOc1cccc(-c2nccc3c2cc(C(=O)O)n3CCS(=O)(=O)Cc2ccccc2)c1] | 1-[2-(benzylsulfonyl)ethyl]-4-(3-ethoxyphenyl)-1H-pyrrolo[3,2-c]pyridine-2-carboxylic acid | 465.1475 |
| 12 | 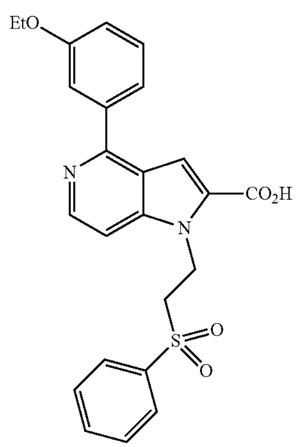 [SMILES: CCOc1cccc(-c2nccc3c2cc(C(=O)O)n3CCS(=O)(=O)c2ccccc2)c1] | 4-(3-ethoxyphenyl)-1-[2-(phenylsulfonyl)ethyl]-1H-pyrrolo[3,2-c]pyridine-2-carboxylic acid | 451.1317 |

-continued

| Ex | Structure | Name | Obs. HRMS (M + H)+ |
|---|---|---|---|
| 13 | 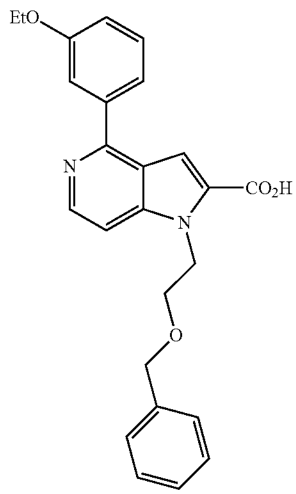 [SMILES: CCOc1cccc(-c2nccc3c2cc(C(=O)O)n3CCOCc2ccccc2)c1] | 1-[2-(benzyloxy)ethyl]-4-(3-ethoxyphenyl)-1H-pyrrolo[3,2-c]pyridine-2-carboxylic acid | 417.1808 |
| 14 | 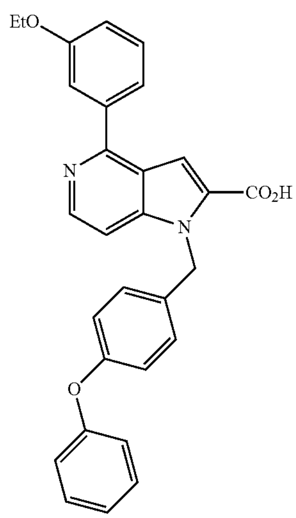 [SMILES: CCOc1cccc(-c2nccc3c2cc(C(=O)O)n3Cc2ccc(Oc3ccccc3)cc2)c1] | 4-(3-ethoxyphenyl)-1-(4-phenoxybenzyl)-1H-pyrrolo[3,2-c]pyridine-2-carboxylic acid | 465.1804 |
| 15 | 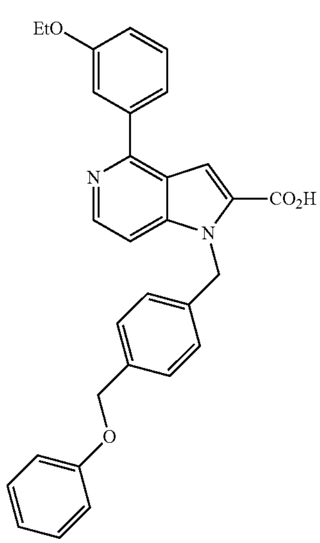 [SMILES: CCOc1cccc(-c2nccc3c2cc(C(=O)O)n3Cc2ccc(COc3ccccc3)cc2)c1] | 4-(3-ethoxyphenyl)-1-[4-(phenoxymethyl)benzyl]-1H-pyrrolo[3,2-c]pyridine-2-carboxylic acid | 479.1963 |

-continued

| Ex | Structure | Name | Obs. HRMS (M + H)+ |
|---|---|---|---|
| 16 | 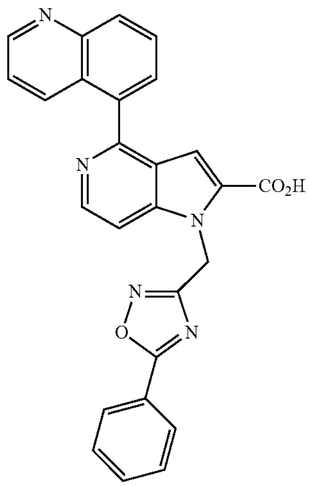 [SMILES: O=C(O)c1cc2c(-c3cccc4ncccc34)nccc2n1Cc1noc(-c2ccccc2)n1] | 1-[(5-phenyl-1,2,4-oxadiazol-3-yl)methyl]-4-(quinolin-5-yl)-1H-pyrrolo[3,2-c]pyridine-2-carboxylic acid | 448.1399 |
| 17 | 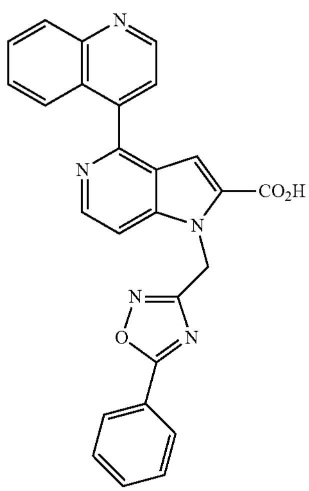 [SMILES: O=C(O)c1cc2c(-c3ccnc4ccccc34)nccc2n1Cc1noc(-c2ccccc2)n1] | 1-[(5-phenyl-1,2,4-oxadiazol-3-yl)methyl]-4-(quinolin-4-yl)-1H-pyrrolo[3,2-c]pyridine-2-carboxylic acid | 448.1391 |
| 18 | 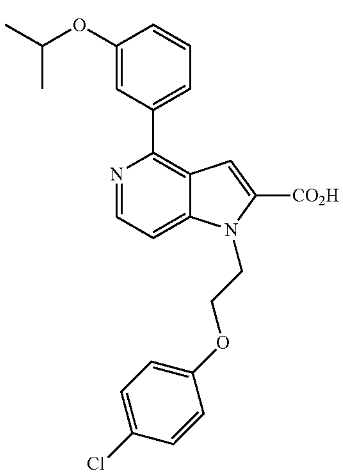 [SMILES: CC(C)Oc1cccc(-c2nccc3c2cc(C(=O)O)n3CCOc2ccc(Cl)cc2)c1] | 1-[2-(4-chlorophenoxy)ethyl]-4-[3-(propan-2-yloxy)phenyl]-1H-pyrrolo[3,2-c]pyridine-2-carboxylic acid | 451.1425 |

-continued

| Ex | Structure | Name | Obs. HRMS (M + H)+ |
|---|---|---|---|
| 19 | 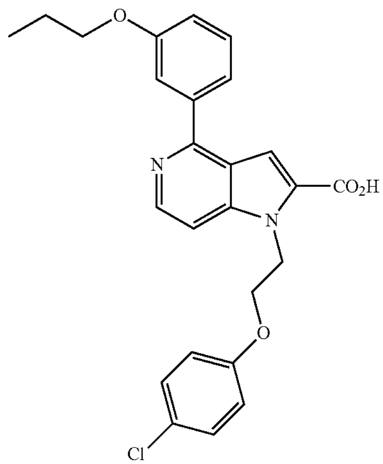 [SMILES: CCCOc1cccc(-c2nccc3c2cc(C(=O)O)n3CCOc2ccc(Cl)cc2)c1] | 1-[2-(4-chlorophenoxy)ethyl]-4-(3-propoxyphenyl)-1H-pyrrolo[3,2-c]pyridine-2-carboxylic acid | 451.1426 |
| 20 | 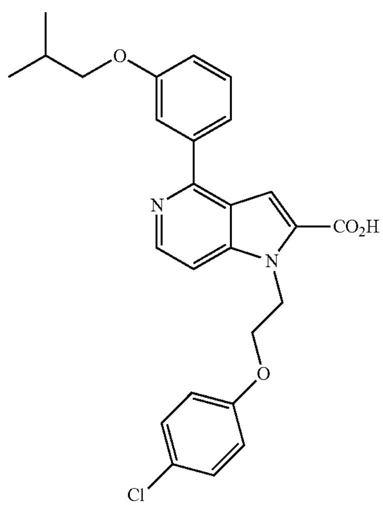 [SMILES: CC(C)COc1cccc(-c2nccc3c2cc(C(=O)O)n3CCOc2ccc(Cl)cc2)c1] | 1-[2-(4-chlorophenoxy)ethyl]-4-[3-(2-methylpropoxy)phenyl]-1H-pyrrolo [3,2-c]pyridine-2-carboxylic acid | 465.1582 |
| 21 | 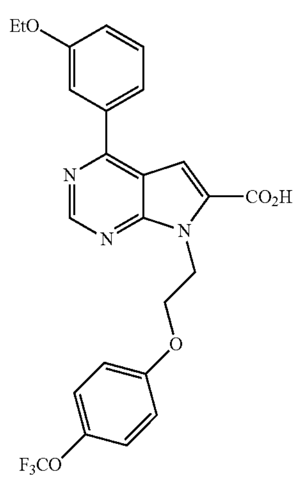 | 4-(3-ethoxyphenyl)-7-{2-[4-(trifluoromethoxy)phenoxy]ethyl}-7H-pyrrolo[2,3-d]pyrimidine-6-carboxylic acid | 488.1448 |

Example 22

4-(3-Ethoxyphenyl)-1-[(1-phenylpyrrolidin-3-yl)methyl]-1H-pyrrolo[3,2-c]pyridine-2-carboxylic acid

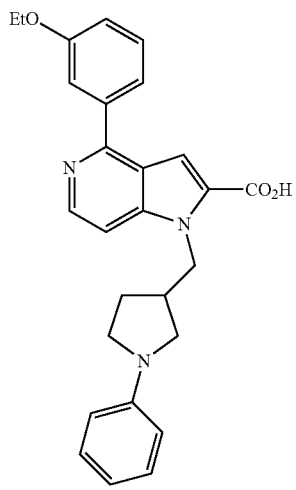 [SMILES: CCOc1cccc(-c2nccc3c2cc(C(=O)O)n3CC2CCN(c3ccccc3)C2)c1]

Methyl 4-(3-ethoxyphenyl)-1H-pyrrolo[3,2-c]pyridine-2-carboxylate (30 mg, 0.101 mmole), (1-phenylpyrrolidin-3-yl)methanol (24 mg, 0.135 mmole), and PPh$_3$ (35 mg, 0.133 mmole) were combined in THF (0.5 mL). To this was added DIAD (0.026 mL, 0.132 mmole) at RT. After stirring overnight 2M NaOH (0.304 mL, 0.607 mmole) was added. After 6 hr the mixture was heated to 70° C. After 90 min the mixture was cooled to RT and concentrated. The crude material was taken up in DMSO and acidified with TFA. The resulting solution was purified by preparative reversed-phase HPLC (30×100 mm Phenomenex AXIA-Gemini-NX, 15%-40% CH$_3$CN/water containing 0.1% TFA over 18 min at 50 mL/min) to give the TFA salt of the title compound (47 mg, 84%) as a light tan solid. $^1$H NMR (499 MHz, DMSO): δ 8.58 (d, J=6.7 Hz, 1 H); 8.28 (s, 1 H); 7.67-7.61 (m, 2 H); 7.54 (d, J=7.7 Hz, 1 H); 7.50 (s, 1 H); 7.30 (d, J=8.2 Hz, 1 H); 7.18-7.12 (m, 2 H); 6.61-6.57 (m, 1 H); 6.48 (d, J=8.1 Hz, 2 H); 4.91 (d, J=7.4 Hz, 2 H); 4.18 (q, J=7.11 Hz, 2 H); 3.40 (m, 1 H); 3.29-3.20 (m, 2 H); 3.08 (m, 1 H); 2.90 (m, 1 H); 1.96 (m, 1 H); 1.83-1.79 (m, 1 H); 1.40 (t, J=6.98 Hz, 3 H). HRMS (ESI) calc (M+H)$^+$=442.2125. found 442.2130.

Example 23

4-(3-Ethoxyphenyl)-1-[(5-phenyl-1H-pyrazol-3-yl)methyl]-1H-pyrrolo[3,2-c]pyridine-2-carboxylic acid

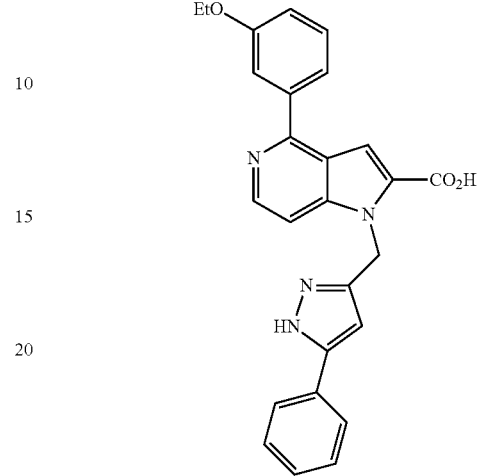

4-(3-Ethoxyphenyl)-1-[(5-phenyl-1-{[2-(trimethylsilyl)ethoxy]methyl}-1H-pyrazol-3-yl)methyl]-1H-pyrrolo[3,2-c]pyridine-2-carboxylic acid (prepared according to Example 22, 136 mg, 0.233 mmole) was taken up in 1M TBAF (5 mL, 5.00 mmole) in THF then heated to reflux. After stirring overnight the mixture was cooled to RT and concentrated. The residue was taken up in H$_2$O. The resulting solid was collected by filtration and washed with H$_2$O. The crude material was taken up in DMSO and acidified with TFA. The resulting solution was purified by preparative reversed-phase HPLC (30×100 mm Phenomenex AXIA-Gemini-NX, 10%-35% CH$_3$CN/water containing 0.1% TFA over 18 min at 50 mL/min) to give the TFA salt of the title compound (67 mg, 52%) as a white solid. $^1$H NMR (399 MHz, DMSO): δ 8.58 (d, J=6.7 Hz, 1H); 8.20 (s, 1 H); 7.69-7.57 (m, 4 H); 7.54 (d, J=7.7 Hz, 1 H); 7.48 (s, 1 H); 7.44-7.35 (m, 2H); 7.34-7.23 (m, 2 H); 6.51 (s, 1 H); 6.05 (s, 2 H); 4.16 (q, J=7.3 Hz, 2 H); 1.39 (t, J=6.9 Hz, 3 H). HRMS (ESI) calc (M+H)$^+$=439.1765. found 439.1770.

The following compounds were synthesized according to the procedures described in Example 22 using the appropriate alcohol in step 1 and were isolated as their TFA salt.

| Example | Structure | Name | Obs. HRMS (M + H)$^+$ |
| --- | --- | --- | --- |
| 24 | ![structure] | 4-(3-ethoxyphenyl)-1-[(5-oxo-1-phenylpyrrolidin-3-yl)methyl]-1H-pyrrolo[3,2-c]pyridine-2-carboxylic acid | 456.1923 |

-continued

| Example | Structure | Name | Obs. HRMS (M + H)+ |
|---|---|---|---|
| 25 | 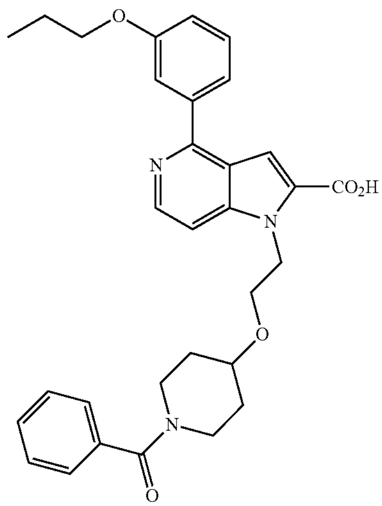 [SMILES: CCCOc1cccc(-c2nccc3c2cc(C(=O)O)n3CCOC2CCN(C(=O)c3ccccc3)CC2)c1] | 1-(2-{[1-(phenylcarbonyl)piperidin-4-yl]oxy}ethyl)-4-(3-propoxyphenyl)-1H-pyrrolo[3,2-c]pyridine-2-carboxylic acid | 528.2496 |
| 26 | 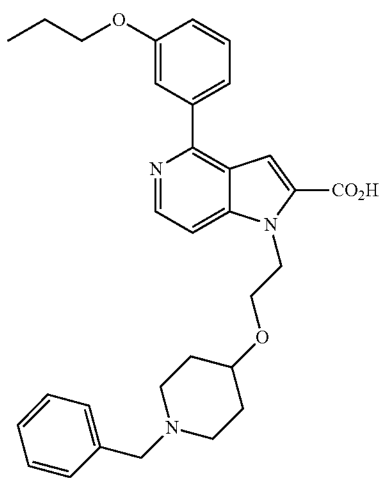 [SMILES: CCCOc1cccc(-c2nccc3c2cc(C(=O)O)n3CCOC2CCN(Cc3ccccc3)CC2)c1] | 1-{2-[(1-benzylpiperidin-4-yl)oxy]ethyl}-4-(3-propoxyphenyl)-1H-pyrrolo[3,2-c]pyridine-2-carboxylic acid | 514.2694 |
| 27 | 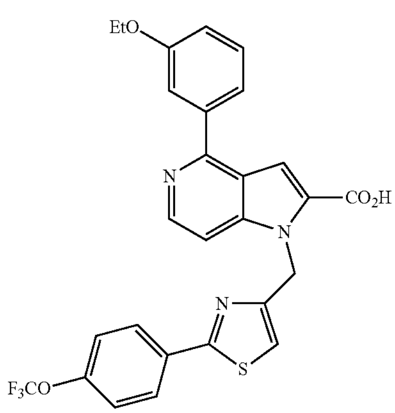 [SMILES: CCOc1cccc(-c2nccc3c2cc(C(=O)O)n3Cc2csc(-c3ccc(OC(F)(F)F)cc3)n2)c1] | 4-(3-ethoxyphenyl)-1-({2-(trifluoromethoxy)phenyl]-1,3-thiazol-4-yl}methyl)-1H-pyrrolo[3,2-c]pyridine-2-carboxylic acid | 540.1209 |

| Example | Structure | Name | Obs. HRMS (M + H)+ |
|---|---|---|---|
| 28 | 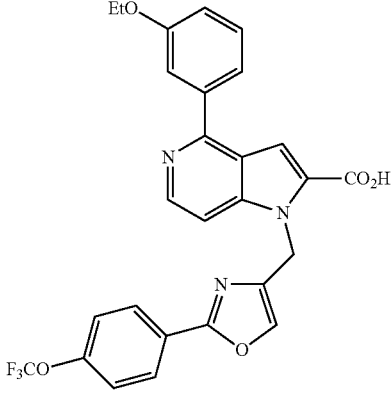 [SMILES: CCOc1cccc(-c2nccc3c2cc(C(=O)O)n3Cc2coc(-c3ccc(OC(F)(F)F)cc3)n2)c1] | 4-(3-ethoxyphenyl)-1-({2-[4-(trifluoromethoxy)phenyl]-1,3-oxazol-4-yl}methyl)-1H-pyrrolo[3,2-c]pyridine-2-carboxylic acid | 524.1437 |
| 29 | 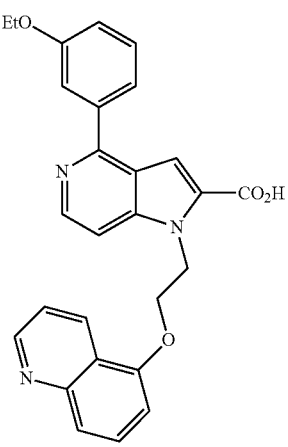 [SMILES: CCOc1cccc(-c2nccc3c2cc(C(=O)O)n3CCOc2cccc3ncccc23)c1] | 4-(3-ethoxyphenyl)-1-[2-(quinolin-5-yloxy)ethyl]-1H-pyrrolo[3,2-c]pyridine-2-carboxylic acid | 454.1771 |
| 30 | 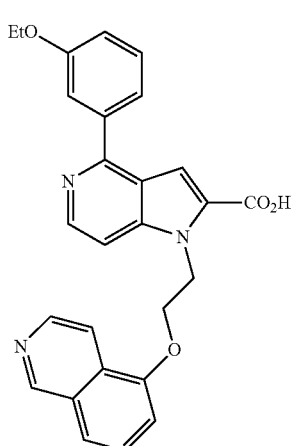 | 4-(3-ethoxyphenyl)-1-[2-(isoquinolin-5-yloxy)ethyl]-1H-pyrrolo[3,2-c]pyridine-2-carboxylic acid | 454.1772 |

| Example | Structure | Name | Obs. HRMS (M + H)+ |
|---|---|---|---|
| 31 | 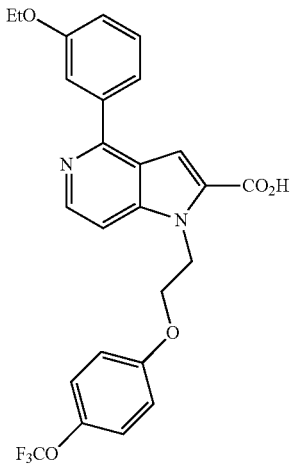 [SMILES: CCOc1cccc(-c2nccc3c2cc(C(=O)O)n3CCOc2ccc(OC(F)(F)F)cc2)c1] | 4-(3-ethoxyphenyl)-1-[2-(isoquinolin-8-yloxy)ethyl]-1H-pyrrolo[3,2-c]pyridine-2-carboxylic acid | 454.1772 |

Example 32

4-(3-Ethoxyphenyl)-1-{2-[4-(trifluoromethoxy)phenoxy]ethyl}-1H-pyrrolo[3,2-a]pyridine-2-carboxylic acid

Step 1: Methyl 1-(2-bromoethyl)-4-(3-ethoxyphenyl)-1H-pyrrolo[3,2-c]pyridine-2-carboxylate

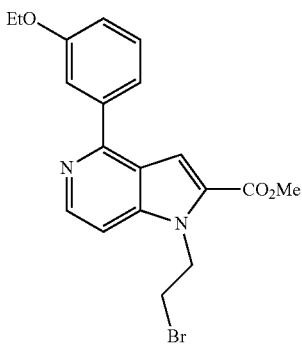 [SMILES: CCOc1cccc(-c2nccc3c2cc(C(=O)OC)n3CCBr)c1]

To a solution of methyl 4-(3-ethoxyphenyl)-1H-pyrrolo[3,2-c]pyridine-2-carboxylate (230 mg, 0.776 mmole) in DMF (7 mL) was added NaH (60% dispersion in mineral oil, 40 mg, 1.000 mmole) at RT. After gas evolution had ceased 1,2-dibromoethane (1 mL, 11.60 mmole) was added rapidly. After stirring overnight the mixture was diluted with $H_2O$ and extracted with EtOAc (3×). The combined organic layers were washed with $H_2O$ and brine then dried ($MgSO_4$), filtered, and concentrated. Flash column (Biotage-SNAP-25 g $SiO_2$, 0-50% EtOAc/hexanes) gave the title compound (135 mg, 43%) as a clear gum. $^1$H NMR (400 MHz, $CDCl_3$): δ 8.51 (d, J=6.0 Hz, 1 H); 7.60 (d, J=1.0 Hz, 1 H); 7.49-7.45 (m, 2 H); 7.40 (m, J=7.9 Hz, 1 H); 7.31 (dd, J=6.0, 1.0 Hz, 1 H); 6.99 (ddd, J=8.2, 2.6, 1.1 Hz, 1 H); 4.92 (t, J=6.83 Hz, 2 H); 4.12 (q, J=7.0 Hz, 2 H); 3.91 (s, 3 H); 3.71 (t, J=7.12 Hz, 2 H); 1.43 (t, J=7.12 Hz, 2 H).

Step 2: 4-(3-Ethoxyphenyl)-1-{2-[4-(trifluoromethoxy)phenoxy]ethyl}-1H-pyrrolo[3,2-c]pyridine-2-carboxylic acid 4-(Trifluoromethoxy)phenol (15.4 mg, 0.086 mmole) and $K_2CO_3$ (24 mg, 0.174 mmole) were combined in a screw cap vial. To this was added a solution of methyl 1-(2-bromoethyl)-4-(3-ethoxyphenyl)-1H-pyrrolo[3,2-c]pyridine-2-carboxylate (22.5 mg, 0.056 mmole) in DMF (0.5 mL). The vial was capped then heated to 60° C. After stirring overnight the mixture was cooled to RT. 2M NaOH (100 uL, 0.200 mmole) was added. After 4 hr at RT the mixture was concentrated. The crude material was taken up in DMSO and acidified with TFA. The resulting solution was purified by preparative reversed-phase HPLC (21×100 mm Phenomenex AXIA-Gemini-NX, 20-45% $CH_3CN$/water containing 0.1% TFA over 18 min at 20 mL/min) to give the TFA salt of the title compound (5 mg, 15%) as a gum. $^1$H NMR (499 MHz, DMSO): δ 8.58 (d, J=6.6 Hz, 1 H); 8.16 (bs, 1 H); 7.58 (m, 2 H); 7.52 (d, J=7.7 Hz, 1 H); 7.47 (m, 1 H); 7.23 (m, 3 H); 6.91 (d, J=8.8 Hz, 2 H); 5.16 (m, 2 H); 4.40 (m, 2 H); 4.15 (q, J=6.73 Hz, 2 H); 1.38 (t, J=6.95 Hz, 3 H). HRMS (ESI) calc (M+H)+=487.1475. found 487.1482.

The following compounds were synthesized according to the procedures described in Example 32 using the appropriate phenol in step 2 and were isolated as their TFA salt.

| Example | Structure | Name | Obs. HRMS (M + H)+ |
|---|---|---|---|
| 33 | 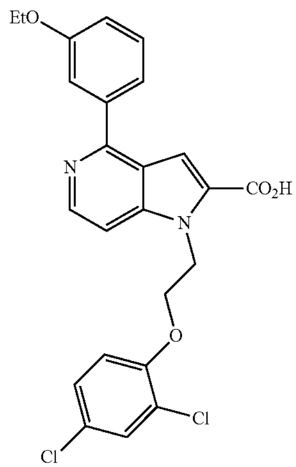 [SMILES: CCOc1cccc(-c2nccc3c2cc(C(=O)O)n3CCOc2ccc(Cl)cc2Cl)c1] | 1-[2-(2,4-dichlorophenoxy)ethyl]-4-(3-ethoxyphenyl)-1H-pyrrolo[3,2-c]pyridine-2-carboxylic acid | 471.0881 |
| 34 | 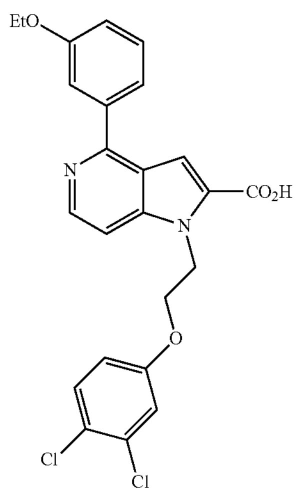 [SMILES: CCOc1cccc(-c2nccc3c2cc(C(=O)O)n3CCOc2ccc(Cl)c(Cl)c2)c1] | 1-[2-(3,4-dichlorophenoxy)ethyl]-4-(3-ethoxyphenyl)-1H-pyrrolo[3,2-c]pyridine-2-carboxylic acid | 471.0881 |
| 35 | 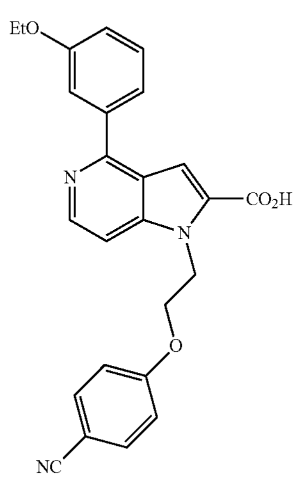 [SMILES: CCOc1cccc(-c2nccc3c2cc(C(=O)O)n3CCOc2ccc(C#N)cc2)c1] | 1-[2-(4-cyanophenoxy)ethyl]-4-(3-ethoxyphenyl)-1H-pyrrolo[3,2-c]pyridine-2-carboxylic acid | 428.1609 |

-continued

| Example | Structure | Name | Obs. HRMS (M + H)+ |
|---------|-----------|------|--------------------|
| 36 | 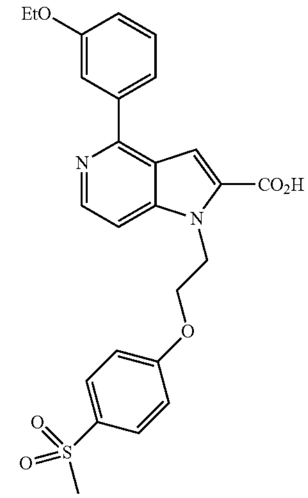 [SMILES: CCOc1cccc(-c2nccc3c2cc(C(=O)O)n3CCOc2ccc(S(C)(=O)=O)cc2)c1] | 4-(3-ethoxyphenyl)-1-{2-[4-(methylsulfonyl)phenoxy]ethyl}-1H-pyrrolo[3,2-c]pyridine-2-carboxylic acid | 481.1437 |
| 37 | 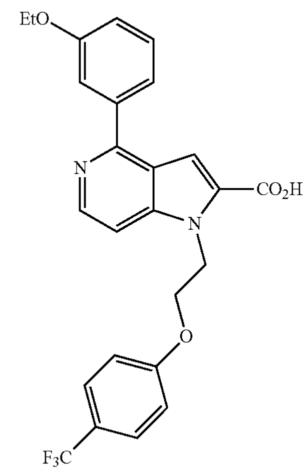 [SMILES: CCOc1cccc(-c2nccc3c2cc(C(=O)O)n3CCOc2ccc(C(F)(F)F)nc2)c1] | 4-(3-ethoxyphenyl)-1-{2-[4-(trifluoromethyl)phenoxy]ethyl}-1H-pyrrolo[3,2-c]pyridine-2-carboxylic acid | 471.1531 |

Example 38

4-(3-Ethoxyphenyl)-1-(2-{[6-(trifluoromethyl)Pyridin-3-yl]oxy}ethyl)-1H-pyrrolo[3,2-c]pyridine-2-carboxylic acid

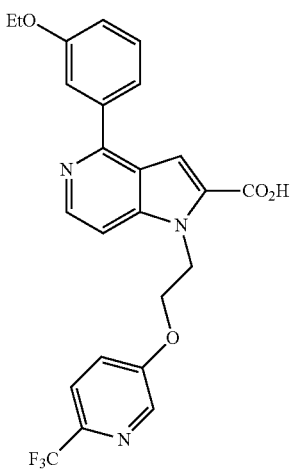

Step 1: Methyl 4-(3-ethoxyphenyl)-1-(2-hydroxyethyl)-1H-pyrrolo[3,2-c]pyridine-2-carboxylate

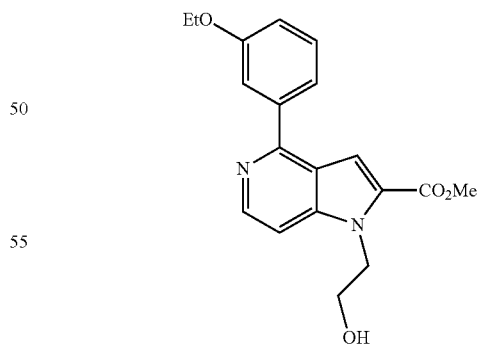

To a solution of methyl 4-(3-ethoxyphenyl)-1H-pyrrolo[3,2-c]pyridine-2-carboxylate (1.02 g, 3.44 mmole) in DMF (15 mL) was added NaH (60% dispersion in mineral oil, 0.179 g, 4.47 mmole) at RT. After gas evolution had ceased (2-bromoethoxy)-tert-butyldimethylsilane (0.960 mL, 4.47 mmole) was added and the mixture heated to 60° C. After 2 hr the mixture was cooled to RT. The mixture was diluted with $H_2O$ and extracted with EtOAc (3×). The combined organic layers were washed with brine, dried (MgSO$_4$), filtered, and concentrated. The crude material was used in the next step without purification.

The crude material above was taken up in THF (20 mL). To this was added triethylamine trihydrofluoride (2.80 mL, 17.20 mmole) at RT. After stirring overnight the mixture was quenched slowly with saturated NaHCO$_3$ then extracted with EtOAc (3×). The combined organic layers were dried (MgSO$_4$), filtered, and concentrated. Flash column chromatography (Biotage-SNAP-25 g SiO$_2$, 70% EtOAc/hexanes) gave the title compound (797 mg, 68%) as a white foam. $^1$H NMR (400 MHz, CDCl$_3$): δ 8.47 (d, J=6.0 Hz, 1 H); 7.60 (m, 1 H); 7.52-7.40 (m, 3 H); 7.32 (dd, J=6.0, 1.0 Hz, 1 H); 7.01 (ddd, J=8.1, 2.6, 1.2 Hz, 1 H); 4.73 (t, J=4.93 Hz, 2 H); 4.15 (q, J=6.9 Hz, 2 H); 4.02 (t, J=5.59 Hz, 2 H); 3.93 (s, 3 H); 1.46 (t, J=6.9 Hz, 3 H).

Step 2: 4-(3-Ethoxyphenyl)-1-(2-{[6-(trifluoromethyl)pyridin-3-yl]oxy}ethyl)-1H-pyrrolo[3,2-c]pyridine-2-carboxylic acid Methyl 4-(3-ethoxyphenyl)-1-(2-hydroxyethyl)-1H-pyrrolo[3,2-c]pyridine-2-carboxylate (30 mg, 0.088 mmole), 6-(trifluoromethyl)pyridine-3-ol (19 mg, 0.116 mmole), and PS-triphenylphosphine resin (116 mg, 0.264 mmole) were combined in a screw cap vial. To this was added THF (1 mL) and DIAD (0.022 mL, 0.115 mmole) at RT. After stirring overnight the mixture was filtered washing with CH$_2$Cl$_2$ and concentrated. The residue was taken up in THF (1 mL). To this was added 2M NaOH (0.132 mL, 0.264 mmole) then the mixture was heated to 60° C. After 3 hr the mixture was cooled to RT and concentrated. The crude material was taken up in DMSO and acidified with TFA. The resulting solution was purified by preparative reversed-phase HPLC (21×100 mm Phenomenex AXIA-Gemini-NX, 15%-40% CH$_3$CN/water containing 0.1% TFA over 18 min at 20 mL/min) to give the title compound (39 mg, 76%) as a white solid. $^1$H NMR (499 MHz, DMSO): δ 8.57 (d, J=6.7 Hz, 1 H); 8.46 (s, 1 H); 8.19 (s, 1H); 7.99 (d, J=8.8 Hz, 1 H); 7.63-7.55 (m, 2 H); 7.48-7.44 (m, 2 H); 7.27 (d, J=8.2 Hz, 1 H); 6.79 (d, J=8.7 Hz, 1 H); 5.18 (m, 2 H); 4.80 (m, 2 H); 4.16 (q, J=7.0 Hz, 2 H); 1.38 (t, J=6.9 Hz, 3 H). HRMS (ESI) calc (M+H)$^+$=472.1479. found 472.1459.

The following compounds were synthesized according to the procedures described in Example 38 using the appropriate phenols in step 2 and were isolated as their TFA salt.

| Example | Structure | Name | Obs. HRMS (M + H)$^+$ |
|---|---|---|---|
| 39 | 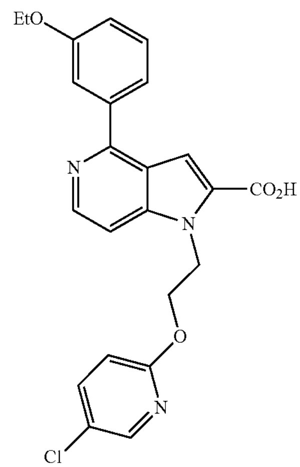 [SMILES: CCOc1cccc(-c2nccc3c2cc(C(=O)O)n3CCOc2ccc(Cl)cn2)c1] | 1-(2-[[(5-chloropyridin-2-yl)oxy]ethyl}-4-(3-ethoxyphenyl)-1H-pyrrolo[3,2-c]pyridine-2-carboxylic acid | 438.1220 |
| 40 | 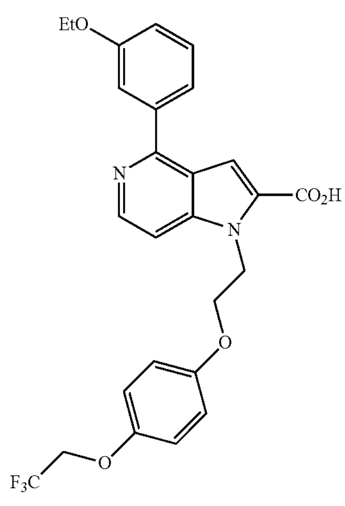 [SMILES: CCOc1cccc(-c2nccc3c2cc(C(=O)O)n3CCOc2ccc(OCC(F)(F)F)cc2)c1] | 4-(3-ethoxyphenyl)-1-{2-[4-(2,2,2-trifluoroethoxy)phenoxy]ethyl}-1H-pyrrolo[3,2-c]pyridine-2-carboxylic acid | 501.1635 |

| Example | Structure | Name | Obs. HRMS (M + H)+ |
|---|---|---|---|
| 41 | 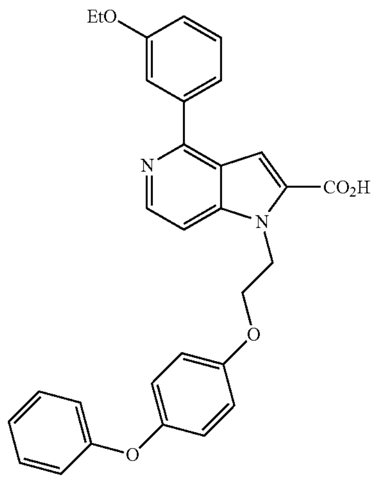 [SMILES: CCOc1cccc(-c2nccc3c2cc(C(=O)O)n3CCOc2ccc(Oc3ccccc3)cc2)c1] | 4-(3-ethoxyphenyl)-1-[2-(4-phenoxyphenoxy)ethyl]-1H-pyrrolo[3,2-c]pyridine-2-carboxylic acid | 495.1918 |
| 42 | 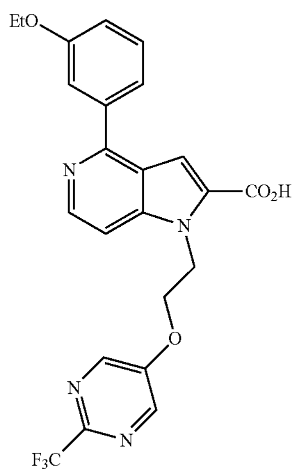 | 4-(3-ethoxyphenyl)-1-(2-{[2-(trifluoromethyl)pyrimidin-5-yl]oxy}ethyl)-1H-pyrrolo[3,2-c]pyridine-2-carboxylic acid | 473.1432 |
| 43 | 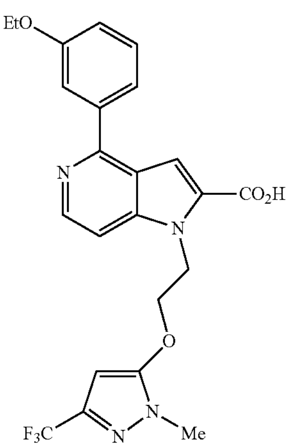 [SMILES: CCOc1cccc(-c2nccc3c2cc(C(=O)O)n3CCOc2cc(C(F)(F)F)nn2C)c1] | 4-(3-ethoxyphenyl)-1-(2-{[1-methyl-3-(trifluoromethyl)-1H-pyrazol-5-yl]oxy}ethyl)-1H-pyrrolo[3,2-c]pyridine-2-carboxylic acid | 475.1593 |

-continued

| Example | Structure | Name | Obs. HRMS (M + H)+ |
|---|---|---|---|
| 44 | 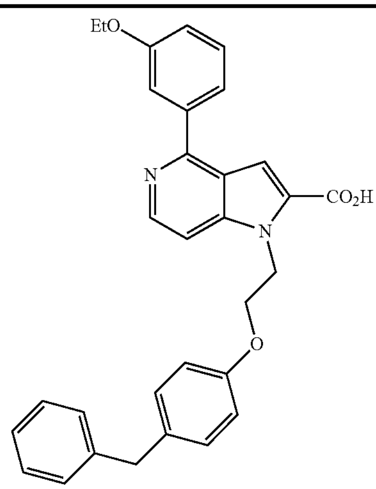 | 1-[2-(4-benzylphenoxy)ethyl]-4-(3-ethoxyphenyl)-1H-pyrrolo[3,2-c]pyridine-2-carboxylic acid | 493.2112 |
| 45 | 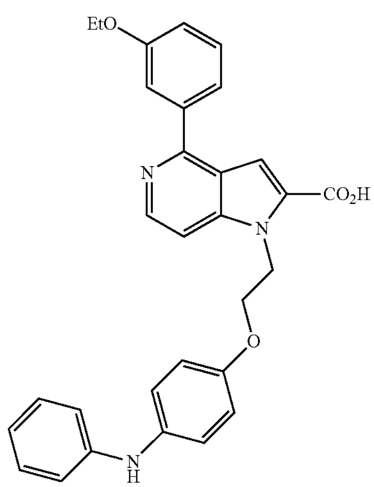 [SMILES: CCOc1cccc(-c2nccc3c2cc(C(=O)O)n3CCOc2ccc(Nc3ccccc3)cc2)c1] | 4-(3-ethoxyphenyl)-1-{2-[4-(phenylamino)phenoxy]ethyl}-1H-pyrrolo[3,2-c]pyridine-2-carboxylic acid | 494.2066 |
| 46 | 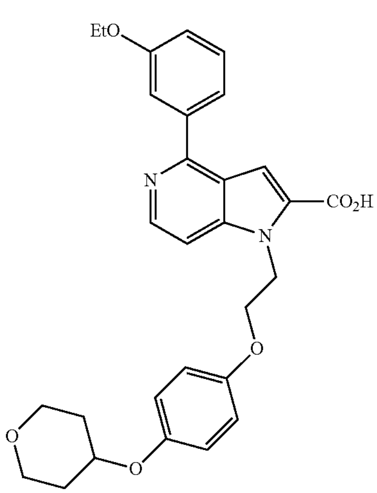 [SMILES: CCOc1cccc(-c2nccc3c2cc(C(=O)O)n3CCOc2ccc(OC3CCOCC3)cc2)c1] | 4-(3-ethoxyphenyl)-1-{2-[4-(tetrahydro-2h-pyran-4-yloxy)phenoxy]ethyl}-1H-pyrrolo[3,2-c]pyridine-2-carboxylic acid | 503.2200 |

| Example | Structure | Name | Obs. HRMS (M + H)+ |
|---|---|---|---|
| 47 | 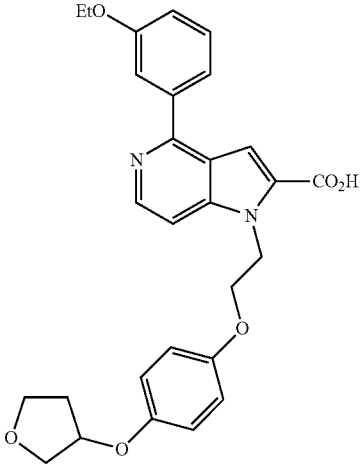 [SMILES: CCOc1cccc(-c2nccc3c2cc(C(=O)O)n3CCOc2ccc(OC3CCOC3)cc2)c1] | 4-(3-ethoxyphenyl)-1-{2-[4-(tetrahydrofuran-3-yloxy)phenoxy]ethyl}-1H-pyrrolo[3,2-c]pyridine-2-carboxylic acid | 489.2041 |
| 48 | 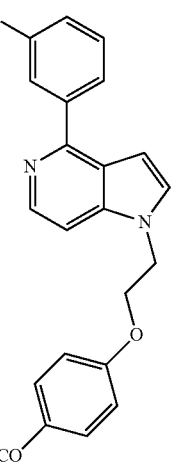 | 4-(3-ethoxyphenyl)-1-{2-[4-(trifluoromethoxy)phenoxy]ethyl}-1H-pyrrolo[3,2-c]pyridine | 443.1579 |

Example 49

4-[(3-Methoxyphenyl)amino]-1-[(5-phenyl-1,2,4-oxadiazol-3-yl)methyl]-1H-pyrrolo[3,2-c]pyridine-2-carboxylic acid

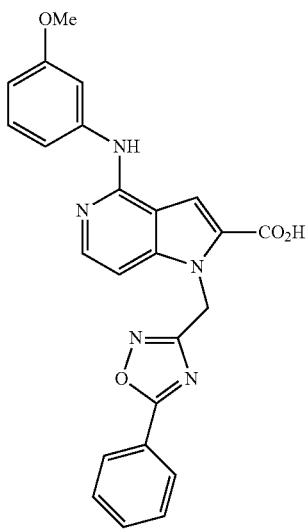 [SMILES: COc1cccc(Nc2nccc3c2cc(C(=O)O)n3Cc2noc(-c3ccccc3)n2)c1]

Step 1: Methyl 4-chloro-1-[(5-phenyl-1,2,4-oxadiazol-3-yl)methyl]-1H-pyrrolo[3,2-c]pyridine-2-carboxylate

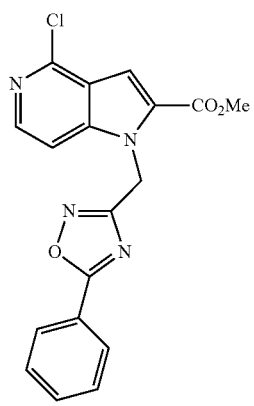 [SMILES: COC(=O)c1cc2c(Cl)nccc2n1Cc1noc(-c2ccccc2)n1]

To a solution of methyl 4-chloro-1H-pyrrolo[3,2-c]pyridine-2-carboxylate (500 mg, 2.374 mmole) in DMF (10 mL) was added NaH (60% dispersion in mineral oil, 123 mg, 3.09 mmole) portionwise at RT. After 30 min 3-(chloromethyl)-5-phenyl-1,2,4-oxadiazole (601 mg, 3.09 mmole) was added all at once as a solid. After 6 hr the mixture was diluted with saturated aqueous $NH_4Cl$ and extracted with EtOAc (3×). The combined organic layers were dried ($MgSO_4$), filtered, and concentrated. Flash column chromatography (Biotage-SNAP-25 g $SiO_2$, 0-20% EtOAc/hexanes) gave the title compound (553 mg, 63%) as a white solid. $^1$H NMR (400 MHz, $CDCl_3$): δ 8.21 (d, J=6.0 Hz, 1 H); 8.05 (dd, J=7.8, 1.5 Hz, 2 H); 7.59-7.54 (m, 1 H); 7.54-7.44 (m, 3 H); 7.39-7.35 (m, 1 H); 6.03 (s, 2 H); 3.97 (s, 3 H).

Step 2: 4-[(3-Methoxyphenyl)amino]-1-[(5-phenyl-1,2,4-oxadiazol-3-yl)methyl]-1H-pyrrolo[3,2-c]pyridine-2-carboxylic acid Methyl 4-chloro-1-[(5-phenyl-1,2,4-oxadiazol-3-yl)methyl]-1H-pyrrolo[3,2-c]pyridine-2-carboxylate (30 mg, 0.081 mmole), $Cs_2CO_3$ (40 mg, 0.123 mmole), $Pd_2(dba)_3$ (4 mg, 4.37 μmol), and 1,1'-bis-(di-t-butylphosphino)ferrocene (4 mg, 8.43 μmol) were combined in a screw cap vial. To this was added 1,4-dioxane (0.5 mL) and meta-anisidine (0.012 mL, 0.106 mmole). $N_2$ was bubbled through the mixture for 10 seconds. The vial was capped then heated to 100° C. After stirring overnight the mixture was cooled to RT. 2M NaOH (0.122 mL, 0.244 mmole) was added and the mixture heated to 60° C. After 3 hr the mixture was cooled to RT. TFA (100 μL) was added and the mixture was concentrated. The residue was taken up in DMSO, filtered using a 0.45 μm PTFE syringe filter, then purified by preparative reversed-phase HPLC (21×100 mm Phenomenex AXIA-Gemini-NX, 10%-35% $CH_3CN$/water containing 0.1% TFA over 18 min at 20 mL/min) to give the TFA salt of the title compound (11 mg, 24%) as a tan solid. $^1$H NMR (499 MHz, DMSO): δ 8.06 (d, J=7.7 Hz, 2 H); 7.95 (m, 1 H); 7.77-7.69 (m, 2 H); 7.66-7.59 (m, 2 H); 7.45 (m, 2 H); 7.31-7.08 (m, 2 H); 6.95 (m, 1 H); 6.17 (s, 2 H); 3.81 (s, 3 H). HRMS (ESI) calc (M+H)$^+$= 442.1510. found 442.1509.

Example 50

1-[(5-Phenyl-1,2,4-oxadiazol-3-yl)methyl]-4-(quinolin-8-yl)-1H-pyrrolo[3,2-c]pyridine-2-carboxylic acid

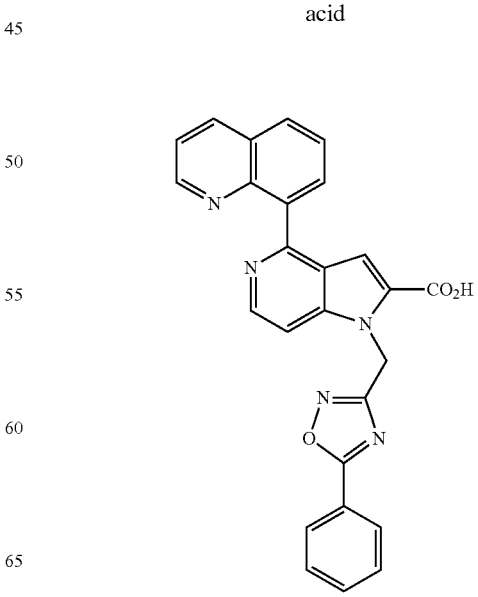

Methyl 4-chloro-1-[(5-phenyl-1,2,4-oxadiazol-3-yl)methyl]-1H-pyrrolo[3,2-c]pyridine-2-carboxylate (30 mg, 0.081 mmole), Pd(OAc)$_2$ (2 mg, 8.91 µmol), 1,1'-bis-(di-t-butylphosphino)ferrocene (4 mg, 8.43 µmol), K$_3$PO$_4$ (52 mg, 0.245 mmole) and quinolin-8-ylboronic acid (19 mg, 0.105 mmole) were combined in a screw cap vial. To this was added 1,4-dioxane (0.5 mL). N$_2$ was bubbled through the mixture for 10 seconds. The vial was capped then heated to 100° C. After stirring overnight the mixture was cooled to RT. 2M NaOH (0.122 mL, 0.244 mmole) was added and the mixture heated to 60° C. After 2 hr 250 µL 2M NaOH was added and heating continued. After 3 hr the mixture was cooled to RT, filtered using a 0.45 µm PTFE syringe filter, then concentrated. The crude material was taken up in DMSO and acidified with TFA. The resulting solution was purified by preparative reversed-phase HPLC (21×100 mm Phenomenex AXIA-Gemini-NX, CH$_3$CN/water containing 0.1% TFA over 18 min at 20 mL/min) to the TFA salt of the title compound (13 mg, 29%) as a tan solid. $^1$H NMR (499 MHz, DMSO): δ 8.96 (dd, J=4.2, 1.7 Hz, 1 H); 8.81 (d, J=6.8 Hz, 1 H); 8.66 (dd, J=8.3, 1.7 Hz, 1 H); 8.50 (d, J=6.9 Hz, 1 H); 8.41 (d, J=8.2 Hz, 1 H); 8.31 (d, J=7.1 Hz, 1 H); 8.08 (d, J=7.7 Hz, 2 H); 7.96-7.91 (m, 1 H); 7.77-7.70 (m, 2 H); 7.67-7.61 (m, 2 H); 7.42 (s, 1 H); 6.36 (s, 2 H). HRMS (ESI) calc (M+H)$^+$= 448.1404. found 448.1404.

The following compounds were synthesized according to the procedures described in Example 50 using the appropriate boronic acid in step 1 and were isolated as their TFA salt.

| Example | Structure | Name | Obs. HRMS (M + H)$^+$ |
|---|---|---|---|
| 51 | 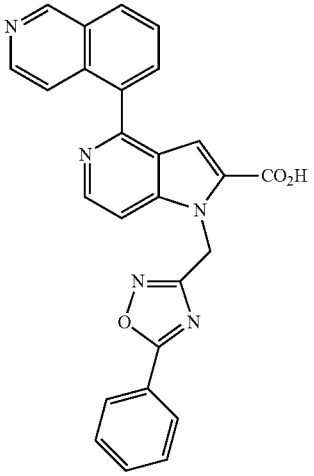 [SMILES: O=C(O)c1cc2c(-c3cccc4cnccc34)nccc2n1Cc1noc(-c2ccccc2)n1] | 4-(isoquinolin-5-yl)-1-[(5-phenyl-1,2,4-oxadiazol-3-yl)methyl]-1H-pyrrolo[3,2-c]pyridine-2-carboxylic acid | 448.1404 |
| 52 | 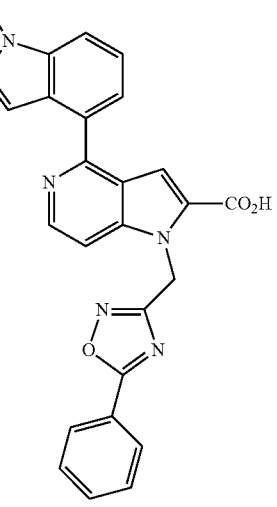 | 4-(1-methyl-1H-indol-4-yl)-1-[(5-phenyl-1,2,4-oxadiazol-3-yl)methyl]-1H-pyrrolo[3,2-c]pyridine-2-carboxylic acid | 450.1563 |

Example 53

4-(Isoquinolin-4-yl)-1-[(5-phenyl-1,2,4-oxadiazol-3-yl)-methyl]-1H-pyrrolo[3,2-c]pyridine-2-carboxylic acid

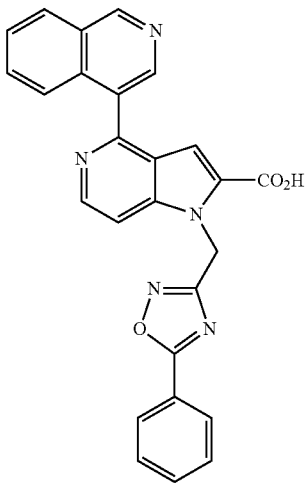 [SMILES: O=C(O)c1cc2c(-c3cncc4ccccc34)nccc2n1Cc1noc(-c2ccccc2)n1]

Intermediate A2,1-Tert-butyl 2-methyl 4-chloro-1H-pyrrolo[3,2-c]pyridine-1,2-dicarboxylate (50 mg, 0.161 mmole), 4-(4,4,5,5-tetramethyl-1,3,2-dioxaborolan-2-yl)isoquinoline (54 mg, 0.212 mmole), Pd(OAc)$_2$ (2 mg, 8.91 µmol), and X-Phos (8 mg, 0.017 mmole) were combined in a screw cap vial. To this was added toluene (0.75 mL) and 4M K$_3$PO$_4$ (0.121 mL, 0.483 mmole). N$_2$ was bubbled through the mixture for 10 seconds. The vial was capped then heated to 80° C. After stirring overnight the mixture was cooled to RT, diluted with EtOAc, then filtered through a pad of Celite washing with EtOAc. The filtrate was concentrated. Flash column chromatography (Biotage-SNAP-10 g SiO$_2$, 0-75% EtOAc/hexanes) gave a clear oil which was sufficiently pure for use in the next step.

The above oil was taken up in 4N HCl in dioxane (1 mL) at RT. Immediately a precipitate formed. After 45 min 0.5 mL DMF was added and the suspension became a solution. After 30 min 1 mL TFA was added. After stirring overnight the mixture was concentrated. The residue was taken up in saturated NaHCO$_3$ and extracted with EtOAc (3×). The combined organic layers were washed with H$_2$O and brine then dried (MgSO$_4$), filtered, and concentrated to a white solid. The material was used in the next step without purification.

To a solution of the above solid in DMF (0.5 mL) was added NaH (60% dispersion in mineral oil, 2.60 mg, 0.065 mmole). After gas evolution had ceased 3-(chloromethyl)-5-phenyl-1,2,4-oxadiazole (12.65 mg, 0.065 mmole) was added all at once as a solid. After stirring overnight 2M NaOH (0.125 mL, 0.250 mmole) was added. After 2 hr the mixture was concentrated. The crude material was taken up in DMSO and acidified with TFA. The resulting solution was purified by preparative reversed-phase HPLC (21×100 mm Phenomenex AXIA-Gemini-NX, 5%-30% CH$_3$CN/water containing 0.1% TFA over 18 min at 20 mL/min) to give the TFA salt of the title compound (7.5 mg, 27%) as an off-white solid. $^1$H NMR (499 MHz, DMSO): δ 9.66 (s, 1H); 8.85 (s, 1 H); 8.76 (d, J=6.4 Hz, 1 H); 8.40 (d, J=8.0 Hz, 1 H); 8.29 (bs, 1 H); 8.08 (d, J=7.7 Hz, 2 H); 7.88 (m, 4 H); 7.73 (m, 1 H); 7.64 (m, 2 H); 7.28 (s, 1 H); 6.31 (s, 2 H). HRMS (ESI) calc (M+H)$^+$=448.1404. found 448.1409.

Example 54

1-[2-(4-Chlorophenoxy)ethyl]-4-(2-ethoxypyridin-4-yl)-1H-pyrrolo[3,2-c]pyridine-2-carboxylic acid

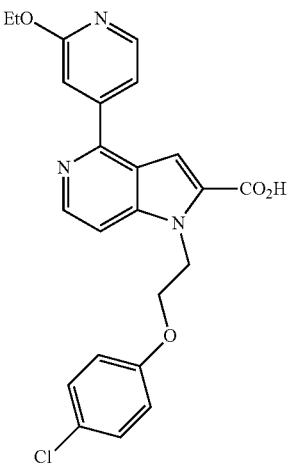 [SMILES: CCOc1cc(-c2nccc3c2cc(C(=O)O)n3CCOc2ccc(Cl)cc2)ccn1]

Step 1: Methyl 4-(2-fluoropyridin-4-yl)-1H-pyrrolo[3,2-c]pyridine-2-carboxylate

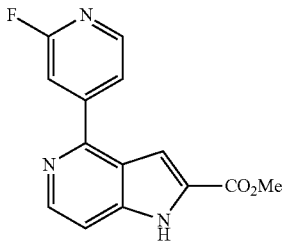 [SMILES: COC(=O)c1cc2c(-c3ccnc(F)c3)nccc2[nH]1]

1-Tert-butyl 2-methyl 4-chloro-1H-pyrrolo[3,2-c]pyridine-1,2-dicarboxylate (100 mg, 0.322 mmole), 2-fluoro-4-(tributylstannyl)pyridine (162 mg, 0.418 mmole), CsF (108 mg, 0.708 mmole), and bis(tri-t-butylphosphine)palladium (0) (16 mg, 0.031 mmole) were combined in a screw cap vial. To this was added 1,4-dioxane (1 mL). N$_2$ was bubbled through the mixture for 10 seconds. The vial was capped then heated to 100° C. After 6 hr was cooled to RT, diluted with EtOAc, filtered through a pad of Celite washing with EtOAc, and concentrated. The residue was taken up in 2 mL CH$_2$Cl$_2$. To this was added 2 mL TFA. After 2 hr the mixture was concentrated. The residue was taken up in saturated NaHCO$_3$ and extracted with CH$_2$Cl$_2$ (3×). The combined organic layers were dried (MgSO$_4$), filtered, and concentrated. Flash column chromatography (Biotage-SNAP-10 g SiO$_2$, 70% EtOAc/hexanes) gave the title compound (67 mg, 77%) as an off-white solid. $^1$H NMR (400 MHz, CDCl$_3$): δ 9.23 (bs, 1 H); 8.56 (d, J=5.8 Hz, 1 H); 8.40 (d, J=5.2 Hz, 1 H); 7.82-7.79 (m, 1 H); 7.56 (s, 1 H); 7.50 (dd, J=2.0, 1.1 Hz, 1 H); 7.43 (dd, J=5.8, 1.1 Hz, 1 H); 4.00 (s, 3 H).

Step 2: Methyl 1-[2-(4-chlorophenoxy)ethyl]-4-(2-fluoropyridin-4-yl)-1H-pyrrolo[3,2-c]pyridine-2-carboxylate

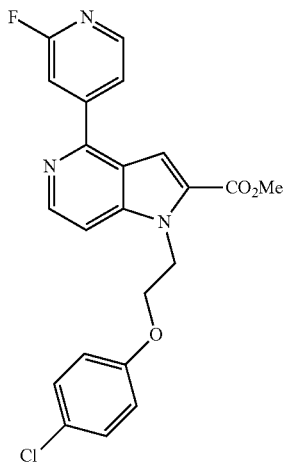 [SMILES: COC(=O)c1cc2c(-c3ccnc(F)c3)nccc2n1CCOc1ccc(Cl)cc1]

To a solution of methyl 4-(2-fluoropyridin-4-yl)-1H-pyrrolo[3,2-c]pyridine-2-carboxylate (67 mg, 0.247 mmole) in DMF (1.2 mL) was added NaH (60% dispersion in mineral oil, 13 mg, 0.325 mmole) at RT. After gas evolution had ceased 1-(2-bromoethoxy)-4-chlorobenzene (76 mg, 0.321 mmole) was added and the mixture was heated to 60° C. After 3 hr the mixture was diluted with $H_2O$ and extracted with EtOAc (3×). The combined organic layers were washed with $H_2O$ and brine, dried ($MgSO_4$), filtered, and concentrated. Flash column chromatography (Biotage-SNAP-10 g $SiO_2$, 35% EtOAc/hexanes) gave the title compound (86 mg, 82%) as a white foam. $^1$H NMR (400 MHz, $CDCl_3$): δ 8.58 (d, J=5.9 Hz, 1 H); 8.39 (d, J=5.2 Hz, 1 H); 7.79 (d, J=5.4 Hz, 1 H); 7.60-7.51 (m, 3 H); 7.18-7.15 (m, 2 H); 6.72-6.67 (m, 2 H); 5.02-4.96 (m, 2 H); 4.39-4.33 (m, 2 H); 3.97 (s, 3 H).

Step 3: 1-[2-(4-Chlorophenoxy)ethyl]-4-(2-ethoxy-pyridin-4-yl)-1H-pyrrolo[3,2-c]pyridine-2-carboxylic acid Methyl 1-[2-(4-chlorophenoxy)ethyl]-4-(2-fluoropyridin-4-yl)-1H-pyrrolo[3,2-c]pyridine-2-carboxylate (61 mg, 0.143 mmole) was taken up in EtOH (1 mL). To this was added sodium ethoxide (0.27 mL, 0.723 mmole, 21% by wt in EtOH) then the mixture was heated to reflux.

After stirring overnight the mixture was cooled to RT and concentrated. The crude material was taken up in DMSO and acidified with TFA. The resulting solution was purified by preparative reversed-phase HPLC (30×100 mm Phenomenex AXIA-Gemini-NX, 15%-40% $CH_3CN$/water containing 0.1% TFA over 18 min at 50 mL/min) to give the TFA salt of the title compound (63 mg, 80%) as a pale yellow solid. $^1$H NMR (400 MHz, DMSO): δ 8.59 (d, J=6.3 Hz, 1 H); 8.40 (d, J=5.3 Hz, 1 H); 8.06 (s, 1 H); 7.57 (s, 1 H); 7.52-7.49 (m, 1 H); 7.31-7.24 (m, 3 H); 6.86-6.81 (m, 2 H); 5.14-5.08 (m, 2 H); 4.44-4.33 (m, 4 H); 1.37 (t, J=7.52 Hz, 3 H). HRMS (ESI) calc (M+H)$^+$=438.1215. found 438.1219.

Example 55

4-(2-Ethoxy-1,3-thiazol-4-yl)-1-{2-[4-(trifluoromethoxy)phenoxy]ethyl}-1H-pyrrolo[3,2-c]pyridine-2-carboxylic acid

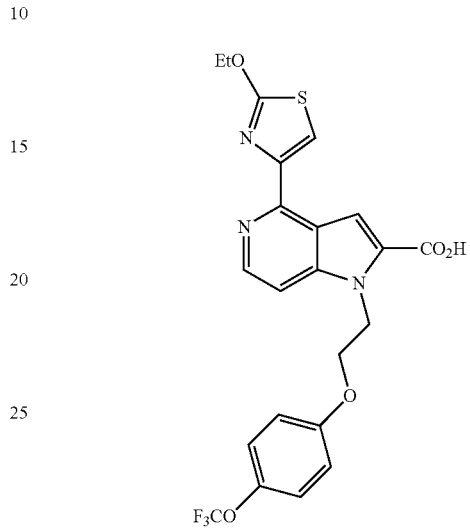

Step 1: Methyl 4-chloro-1-{2-[4-(trifluoromethoxy)phenoxy]ethyl}-1H-pyrrolo[3,2-c]pyridine-2-carboxylate

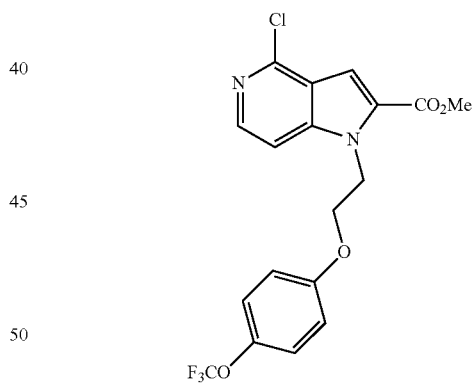

To a solution of Methyl 4-chloro-1H-pyrrolo[3,2-c]pyridine-2-carboxylate (350 mg, 1.662 mmole) in DMF (6 mL) was added NaH (60% dispersion in mineral oil, 86 mg, 2.160 mmole) portionwise at RT. After gas evolution had ceased a solution of 1-(2-bromoethoxy)-4-(trifluoromethoxy)benzene (616 mg, 2.160 mmole) in DMF (1 mL) was added. After the addition was complete the mixture was heated to 60° C. After 4 hr the mixture was cooled to RT. The mixture was diluted with water and extracted with EtOAc (3×). The combined organic layers were washed with $H_2O$ and brine, dried ($MgSO_4$), filtered, and concentrated. Flash column (Biotage-SNAP-25 g $SiO_2$, 30% EtOAc/hexanes) gave the title compound (492 mg, 71%) as a white solid. $^1$H NMR (400 MHz, $CDCl_3$): δ 8.21 (d, J=6.0 Hz, 1 H); 7.45 (s, 1 H); 7.42 (d, J=6.0

Hz, 1 H); 7.07 (d, J=8.6 Hz, 2 H); 6.76-6.70 (m, 2 H); 4.93 (t, J=5.13 Hz, 2 H); 4.34 (t, J=5.0 Hz, 3 H); 3.95 (s, 3 H).

Step 2: 4-(2-Ethoxy-1,3-thiazol-4-yl)-1-{2-[4-(trifluoromethoxy)phenoxy]ethyl}-1H-pyrrolo[3,2-c]pyridine-2-carboxylic acid Methyl 4-chloro-1-{2-[4-(trifluoromethoxy)phenoxy]ethyl}-1H-pyrrolo[3,2-c]pyridine-2-carboxylate (30 mg, 0.072 mmole), bis(tri-t-butylphosphine)palladium(0) (3.70 mg, 7.23 µmol), CsF (25 mg, 0.165 mmole), and 2-ethoxy-4-(tributylstannyl)thiazole (40 mg, 0.096 mmole) were combined in a screw cap vial. To this was added 1,4-dioxane (0.5 mL). N$_2$ was bubbled through the mixture for 10 seconds. The vial was capped then heated to 100° C. After stirring overnight the mixture was cooled to RT, diluted with EtOAc, filtered through a pad of Celite washing with EtOAc, and concentrated. The residue was taken up in THF (1 mL). To this was added 2M NaOH (0.108 mL, 0.217 mmole) then the mixture was heated to 60° C. After 5 hr the mixture was concentrated. The crude material was taken up in DMSO and acidified with TFA. The resulting solution was purified by preparative reversed-phase HPLC (21×100 mm Phenomenex AXIA-Gemini-NX, 20%-45% CH$_3$CN/water containing 0.1% TFA over 18 min at 20 mL/min) to give the TFA salt of the title compound (6 mg, 14%) as a pale yellow solid. $^1$H NMR (499 MHz, DMSO): δ 8.37 (d, J=5.8 Hz, 1 H); 8.05 (s, 1 H); 7.87 (bs, 1 H); 7.68 (bs, 1 H); 7.22 (d, J=8.6 Hz, 2 H); 6.90 (d, J=8.7 Hz, 2 H); 5.01 (m, 2 H); 4.58 (q, J=7.06 Hz, 2 H); 4.33 (m, 2 H); 1.47 (t, J=7.0 Hz, 3 H). HRMS (ESI) calc (M+H)$^+$=494.0992. found 494.0992.

The following compounds were synthesized according to the procedures described in Examples 54 using the appropriate amines in step 3 and were isolated as their TFA salt.

| Example | Structure | Name | Obs. HRMS (M + H)$^+$ |
|---|---|---|---|
| 56 | 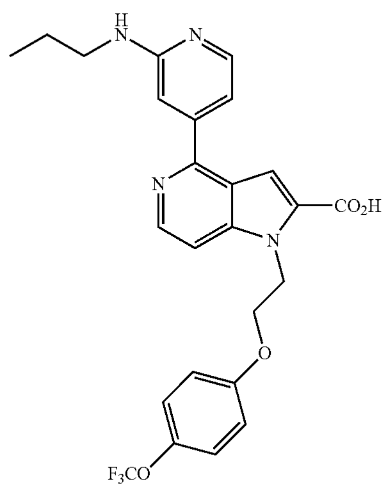 [SMILES: CCCNc1cc(-c2nccc3c2cc(C(=O)O)n3CCOc2ccc(OC(F)(F)F)cc2)ccn1] | 4-[2-(propylamino)pyridin-4-yl]-1-{2-[4-(trifluoromethoxy)phenoxy]ethyl}-1H-pyrrolo[3,2-c]pyridine-2-carboxylic acid | 501.1751 |
| 57 | 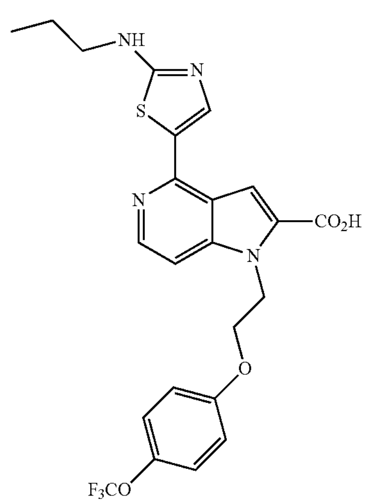 [SMILES: CCCNc1ncc(-c2nccc3c2cc(C(=O)O)n3CCOc2ccc(OC(F)(F)F)cc2)s1] | 4-[2-(propylamino)-1,3-thiazol-5-yl]-1-{2-[4-(trifluoromethoxy)phenoxy]ethyl}-1H-pyrrolo[3,2-c]pyridine-2-carboxylic acid | 507.1313 |

| Example | Structure | Name | Obs. HRMS (M + H)+ |
|---|---|---|---|
| 58 | 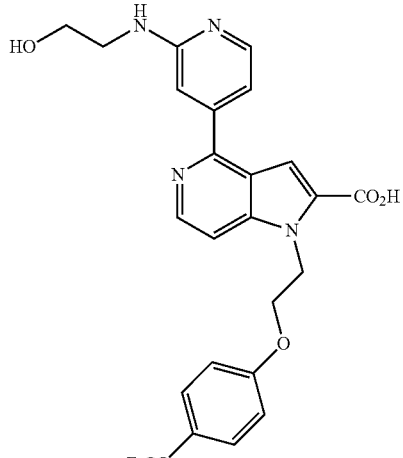 | 4-[2-(propylamino)pyrimidin-4-yl]-1-{2-[4-(trifluoromethoxy)phenoxy]ethyl}-1H-pyrrolo[3,2-c]pyridine-2-carboxylic acid | 502.1680 |

Example 59
4-{2-[(2-Hydroxyethyl)amino]pyridin-4-yl}-1-{2-[4-(trifluoromethoxy)phenoxy]ethyl}-1H-pyrrolo[3,2-c]pyridine-2-carboxylic acid

Step 1: 4-(2-Fluoropyridin-4-yl)-1-{2-[4-(trifluoromethoxy)phenoxy]ethyl}-1H-pyrrolo[3,2-c]pyridine-2-carboxylic acid potassium salt

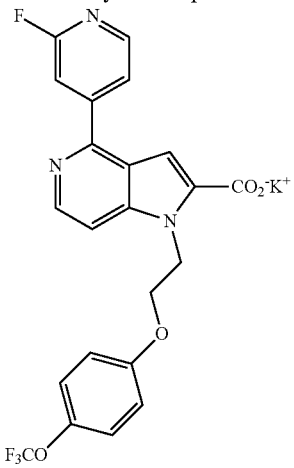

Methyl 4-chloro-1-{2-[4-(trifluoromethoxy)phenoxy]ethyl}-1H-pyrrolo[3,2-c]pyridine-2-carboxylate (50 mg, 0.121 mmole), 2-fluoro-4-(tributylstannyl)pyridine (61 mg, 0.158 mmole), and bis(tri-t-butylphosphine)palladium(0) (6 mg, 0.012 mmole) were combined in a screw cap vial. To this was added 1,4-dioxane (0.5 mL). $N_2$ was bubbled through the mixture for 10 seconds. The vial was capped then heated to 100° C. After stirring overnight the mixture was cooled to RT. Excess QuadraPure was added and stirring continued at RT. After stirring 6 hr the mixture was filtered washing with EtOAc and concentrated. The residue was taken up in 1 mL THF. To this was added KOTMS (47 mg, 0.366 mmole) at RT. After 3 hr the mixture was concentrated. The residue was taken up in $Et_2O$. The resulting off-white solid (53 mg, 88%) was collected by filtration washing with $Et_2O$ and dried in vacuo. $^1H$ NMR (400 MHz, DMSO): δ 8.39 (d, J=5.1 Hz, 1 H); 8.35 (d, J=5.9 Hz, 1 H); 7.95 (d, J=5.1 Hz, 1 H); 7.63 (d, J=6.3 Hz, 2 H); 7.21 (d, J=8.4 Hz, 2 H); 7.04 (s, 1 H); 6.95 (d, J=8.8 Hz, 2 H); 5.12-5.05 (m, 2 H); 4.39-4.33 (m, 2 H).

Step 2: 4-{2-[(2-Hydroxyethyl)amino]pyridin-4-yl}-1-{2-[4-(trifluoromethoxy)phenoxy]ethyl}-1H-pyrrolo[3,2-c]pyridine-2-carboxylic acid 4-(2-Fluoropyridin-4-yl)-1-{2-[4-(trifluoromethoxy)phenoxy]ethyl}-1H-pyrrolo[3,2-c]pyridine-2-carboxylic acid potassium salt (25 mg, 0.050 mmole) was taken up in pyridine (0.3 mL) in a screw cap vial. To this was added ethanolamine (0.015 mL, 0.250 mmole). The vial was capped then heated to 120° C. After stirring overnight ethanolamine (0.015 mL, 0.250 mmole) was added and heating continued. After stirring overnight the mixture was cooled to RT and concentrated. The crude material was taken up in DMSO and acidified with TFA. The resulting solution was purified by preparative reversed-phase HPLC (30×100 mm Phenomenex AXIA-Gemini-NX, 5%-95% $CH_3CN$/water containing 0.1% TFA over 18 min at 50 mL/min) to give the title compound (16 mg, 52%) as a yellow solid. $^1H$ NMR (499 MHz, DMSO): δ 8.58 (d, J=5.9 Hz, 1 H); 8.04 (d, J=6.7 Hz, 1 H); 7.95 (d, J=6.0 Hz, 1 H); 7.73 (s, 1 H); 7.66 (s, 1 H); 7.43 (d, J=6.6 Hz, 1 H); 7.23 (d, J=8.6 Hz, 2 H); 6.90 (d, J=8.8 Hz, 2 H); 5.13-5.04 (m, 2H); 4.39-4.35 (m, 2 H); 3.68 (m, 2 H); 3.49 (bs, 2 H). HRMS (ESI) calc (M+H)+=503.1537. found 503.1529.

Example 60

4-(3-Ethoxyphenyl)-1-(2-{[4-(2,2,2-trifluoroethoxy)phenyl]amino}ethyl)-1H-pyrrolo[3,2-c]pyridine-2-carboxylic acid

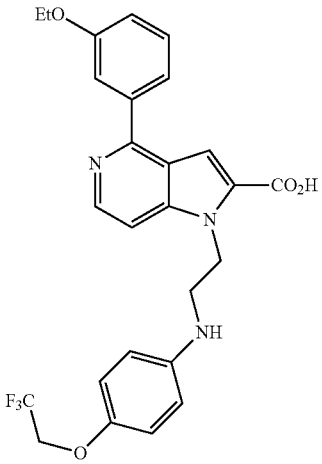 [SMILES: CCOc1cccc(-c2nccc3c2cc(C(=O)O)n3CCNc2ccc(OCC(F)(F)F)cc2)c1]

Methyl 4-(3-ethoxyphenyl)-1-(2-hydroxyethyl)-1H-pyrrolo[3,2-c]pyridine-2-carboxylate (50 mg, 0.147 mmole) and NMO (26 mg, 0.222 mmole) were taken up in $CH_2Cl_2$ (1 mL). To this was added powdered 5A sieves (75 mg) and TPAP (3 mg, 8.54 mmol) at RT. After 5 hr the mixture was filtered through a plug of silica gel washing with EtOAc then concentrated. The crude material was used immediately in the next step as is.

The crude material from above, 4-(2,2,2-trifluoroethoxy)aniline (36.5 mg, 0.191 mmole), and AcOH (0.042 mL, 0.735 mmole) were combined in $CH_2Cl_2$ (1 mL). After 5 min $NaBH(OAc)_3$ (46.7 mg, 0.221 mmole) was added all at once as a solid. After stirring overnight the mixture was concentrated. The residue was taken up in 1 mL MeOH. To this was added 5M KOH (0.294 mL, 1.470 mmole) then the mixture was heated to 60° C. After stirring overnight the mixture was cooled to RT and concentrated. The crude material was taken up in DMSO and acidified with TFA. The resulting solution was purified by preparative reversed-phase HPLC (30×100 mm Phenomenex ARIA-Gemini-NX, 15%-40% $CH_3CN$/water containing 0.1% TFA over 18 min at 20 mL/min) to give the TFA salt of the title compound (17 mg, 19%) as a light tan solid. $^1$H NMR (499 MHz, DMSO): δ 8.52 (d, J=6.8 Hz, 1 H); 7.97 (d, J=6.4 Hz, 1 H); 7.62 (m, 2 H); 7.48 (d, J=7.7 Hz, 1 H); 7.43 (s, 1 H); 7.30 (d, J=8.2 Hz, 1 H); 6.77 (d, J=8.4 Hz, 2 H); 6.46 (d, J=8.4 Hz, 2 H); 4.86 (m, 2 H); 4.52 (q, J=8.9 Hz, 2 H); 4.17 (q, J=6.9 Hz, 2H); 1.39 (t, J=6.9 Hz, 3 H). HRMS (ESI) calc $(M+H)^+$=500.1792. found 500.1779.

Example 61

4-[2-(3-Methylpyrrolidin-1-yl)-1,3-thiazol-5-yl]-1-{2-[4-(trifluoromethoxy)phenoxy]ethyl}-1H-pyrrolo[3,2-c]pyridine-2-carboxylic acid

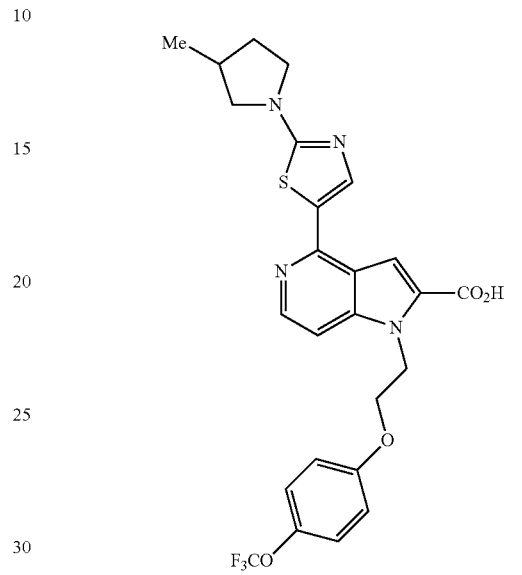

To a solution of 5-bromo-2-(3-methylpyrrolidin-1-yl)-1,3-thiazole (36 mg, 0.146 mmole) in 2-MeTHF (0.25 mL) was added n-BuLi (0.090 mL, 0.144 mmole) at −78° C. After 20 min 0.5 M $ZnCl_2$ in THF (0.29 mL, 0.145 mmole) was added. The cooling bath was removed and the mixture was allowed to warm to RT. After 30 min the mixture was transferred via syringe to a vial containing methyl 4-chloro-1-{2-[4-(trifluoromethoxy)phenoxy]ethyl}-1H-pyrrolo[3,2-c]pyridine-2-carboxylate (30 mg, 0.072 mmole) and bis(tri-t-butylphosphine)palladium(0) (4 mg, 7.83 μmol). $N_2$ was bubbled through the mixture for 10 seconds. The vial was capped then heated to 80° C. After stirring overnight the mixture was cooled to RT. 2M NaOH (0.108 mL, 0.217 mmole) was added and the mixture heated to 60° C. After stirring overnight the mixture was cooled to RT and concentrated. The crude material was taken up in DMSO and acidified with TFA. The resulting solution was purified by preparative reversed-phase HPLC (21×100 mm Phenomenex AXIA-Gemini-NX, 20%-45% $CH_3CN$/water containing 0.1% TFA over 18 min at 20 mL/min) to give the TFA salt of the title compound (9.7 mg, 21%) as a bright yellow solid. $^1$H NMR (499 MHz, DMSO): δ 8.33 (s, 1 H); 8.28 (d, J=6.5 Hz, 1 H); 7.77 (s, 1 H); 7.74 (s, 1H); 7.23 (d, J=8.6 Hz, 2 H); 6.90 (d, J=8.8 Hz, 2 H); 5.07 (s, 2 H); 4.37-4.32 (m, 2 H); 3.53 (m, 1 H); 3.14-3.08 (m, 1 H); 2.48 (m, 3 H); 2.18 (m, 1 H); 1.70 (m, 1 H); 1.11 (d, J=6.6 Hz, 3 H). HRMS (ESI) calc $(M+H)^+$=533.1465. found 533.1464.

Example 62

1-[2-(4-Tert-butoxyphenoxy)ethyl]-4-(3-ethoxyphenyl)-1H-pyrrolo[3,2-c]pyridine-2-carboxylic acid

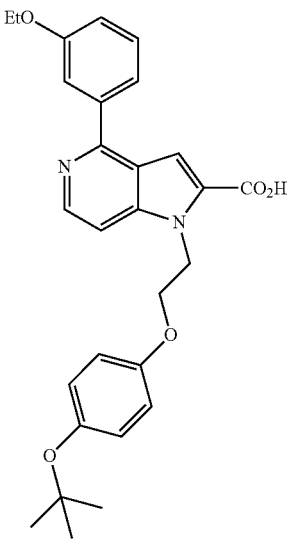 [SMILES: CCOc1cccc(-c2nccc3c2cc(C(=O)O)n3CCOc2ccc(OC(C)(C)C)cc2)c1]

Step 1: Methyl 1-[2-(4-tert-butoxyphenoxy)ethyl]-4-chloro-1H-pyrrolo[3,2-c]pyridine-2-carboxylate

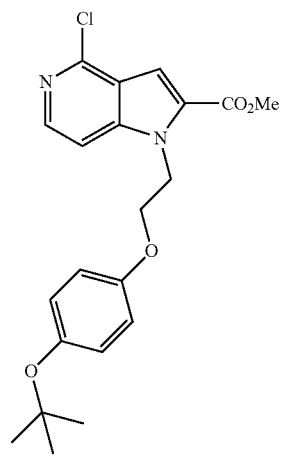 [SMILES: COC(=O)c1cc2c(Cl)nccc2n1CCOc1ccc(OC(C)(C)C)cc1]

Methyl 4-chloro-1H-pyrrolo[3,2-c]pyridine-2-carboxylate (500 mg, 2.374 mmole), 2-(4-tert-butoxyphenoxy)ethanol (624 mg, 2.97 mmole), and PPh$_3$ (778 mg, 2.97 mmole) were combined in toluene (10 mL) at RT. To this was added DIAD (0.58 mL, 2.98 mmole) slowly at RT. After 3 hr the mixture was concentrated. Flash column chromatography (Biotage-SNAP-50 g SiO$_2$, 0-25% EtOAc/hexanes) gave the title compound (1.0 g, 105%) as a white solid. $^1$H NMR (400 MHz, CDCl$_3$): δ 8.18 (d, J=6.0 Hz, 1 H); 7.44 (d, J=1.0 Hz, 1 H); 7.43-7.38 (m, 1 H); 6.85-6.81 (m, 2 H); 6.64-6.60 (m, 2 H); 4.92 (t, J=5.0 Hz, 2 H); 4.31 (t, J=5.0 Hz, 2 H); 3.95 (s, 3H); 1.26 (s, 9 H).

Step 2: Methyl 1-[2-(4-tert-butoxyphenoxy)ethyl]-4-(3-ethoxyphenyl)-1H-pyrrolo[3,2-c]pyridine-2-carboxylate

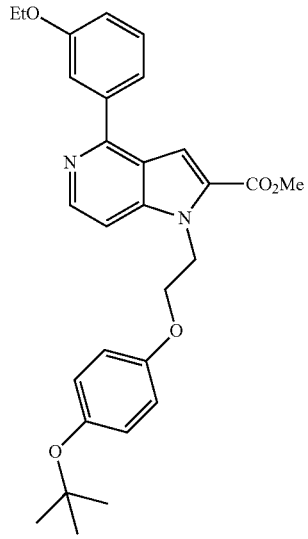 [SMILES: CCOc1cccc(-c2nccc3c2cc(C(=O)OC)n3CCOc2ccc(OC(C)(C)C)cc2)c1]

Methyl 1-[2-(4-tert-butoxyphenoxy)ethyl]-4-chloro-1H-pyrrolo[3,2-c]pyridine-2-carboxylate (1 g, 2.482 mmole), 3-ethoxyphenylboronic acid (0.618 g, 3.72 mmole), KF (0.433 g, 7.45 mmole), and bis(tri-t-butylphosphine)palladium(0) (0.127 g, 0.248 mmole) were combined in 1,4-dioxane (10 mL). The mixture was degassed (3× pump/N$_2$) then heated to reflux. After 5 hr the mixture was cooled to RT, diluted with EtOAc, filtered through a pad of Celite washing with EtOAc, and concentrated. Flash column chromatography (Biotage-SNAP-50 g SiO$_2$, 0-30% EtOAc/hexanes) gave the title compound (939 mg, 77%) as an off-white foam. $^1$H NMR (400 MHz, CDCl$_3$): 8.52 (d, J=6.0 Hz, 1 H); 7.61 (d, J=0.9 Hz, 1 H); 7.52-7.47 (m, 2 H); 7.43 (d, J=7.2 Hz, 2 H); 7.01 (ddd, J=8.2, 2.6, 1.0 Hz, 1 H); 6.87-6.83 (m, 2 H); 6.70-6.66 (m, 2 H); 4.98-4.92 (m, 2 H); 4.37-4.31 (m, 2 H); 4.14 (dd, J=14.0, 7.0 Hz, 2 H); 3.93 (s, 3 H); 1.45 (t, J=7.0 Hz, 3H); 1.26 (s, 9 H).

Step 3: 1-[2-(4-Tert-butoxyphenoxy)ethyl]-4-(3-ethoxyphenyl)-1H-pyrrolo[3,2-c]pyridine-2-carboxylic acid Methyl 1-[2-(4-tert-butoxyphenoxy)ethyl]-4-(3-ethoxyphenyl)-1H-pyrrolo[3,2-c]pyridine-2-carboxylate (25 mg, 0.051 mmole) was taken up in MeOH (0.5 mL) in a screw cap vial. To this was added 2M NaOH (0.077 mL, 0.154 mmole). The vial was capped then heated to 60° C. After 4 hr the mixture was cooled to RT and concentrated. The crude material was taken up in DMSO and acidified with TFA. The resulting solution was filtered using a 0.45 µm PTFE syringe filter then purified by preparative reversed-phase HPLC (21× 100 mm Phenomenex AXIA-Gemini-NX, 20%-45% CH$_3$CN/water containing 0.1% TFA over 18 min at 20 mL/min) to give the TFA salt of the title compound (30 mg, 100%) as a white foam. $^1$H NMR (499 MHz, DMSO): δ 8.61 (d, J=6.8 Hz, 1 H); 8.29 (d, J=7.0 Hz, 1 H); 7.65-7.60 (m, 2 H); 7.55-7.46 (m, 2 H); 7.30 (d, J=8.3 Hz, 1 H); 6.81 (d, J=8.4 Hz, 2 H); 6.69 (d, J=8.5 Hz, 2 H); 5.17 (s, 2 H); 4.34 (s, 2 H); 4.17 (q, J=6.9 Hz, 2 H); 1.39 (t, J=6.9 Hz, 3 H); 1.18 (s, 9 H). HRMS (ESI) calc (M+H)$^+$=475.2227. found 475.2213.

The following compounds were synthesized according to the procedures described in Example 62 using the appropriate phenol in step 1 and boronic acid in step 2 and were isolated as their TFA salt.

| Example | Structure | Name | Obs. HRMS (M + H)+ |
|---|---|---|---|
| 63 | 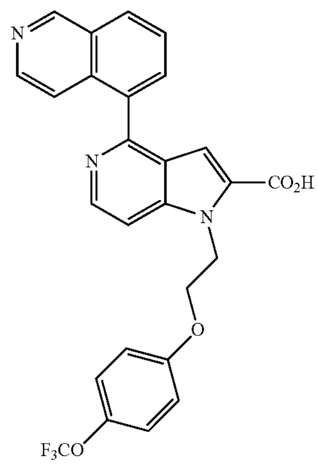 [SMILES: O=C(O)c1cc2c(-c3cccc4cnccc34)nccc2n1CCOc1ccc(OC(F)(F)F)cc1] | 4-(isoquinolin-5-yl)-1-{2-[4-(trifluoromethoxy)phenoxy]ethyl}-1H-pyrrolo[3,2-c]pyridine-2-carboxylic acid | 494.1317 |
| 64 | 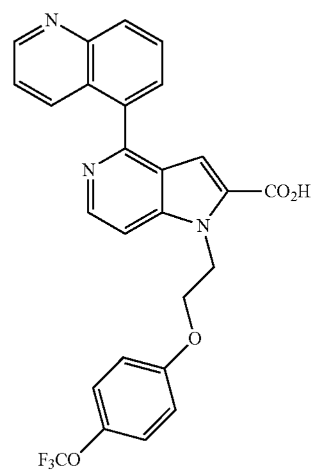 [SMILES: O=C(O)c1cc2c(-c3cccc4ncccc34)nccc2n1CCOc1ccc(OC(F)(F)F)cc1] | 4-(quinolin-5-yl)-1-{2-[4-(trifluoromethoxy)phenoxy]ethyl}-1H-pyrrolo[3,2-c]pyridine-2-carboxylic acid | 494.1313 |
| 65 | 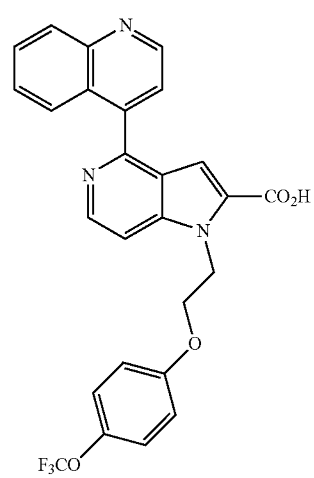 [SMILES: O=C(O)c1cc2c(-c3ccnc4ccccc34)nccc2n1CCOc1ccc(OC(F)(F)F)cc1] | 4-(quinolin-4-yl)-1-{2-[4-(trifluoromethoxy)phenoxy]ethyl}-1H-pyrrolo[3,2-c]pyridine-2-carboxylic acid | 494.1314 |

| Example | Structure | Name | Obs. HRMS (M + H)+ |
|---|---|---|---|
| 66 | 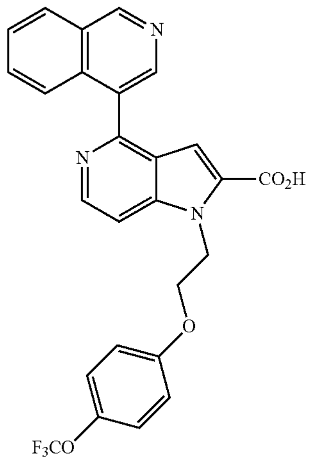 [SMILES: O=C(O)c1cc2c(-c3cncc4ccccc34)nccc2n1CCOc1ccc(OC(F)(F)F)cc1] | 4-(isoquinolin-4-yl)-1-{2-[4-(trifluoromethoxy)phenoxy]ethyl}-1H-pyrrolo[3,2-c]pyridine-2-carboxylic acid | 494.1317 |

Example 67

4-(3-Ethoxyphenyl)-1-{2-[4-(pyridin-3-yloxy)phenoxy]ethyl}-1H-pyrrolo[3,2-c]pyridine-2-carboxylic acid

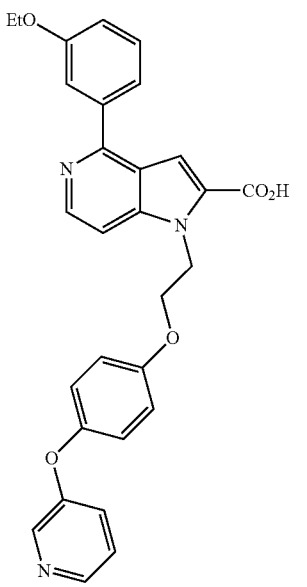

Step 1: Methyl 4-(3-ethoxyphenyl)-1-[2-(4-hydroxyphenoxy)ethyl]-1H-pyrrolo[3,2-c]pyridine-2-carboxylate

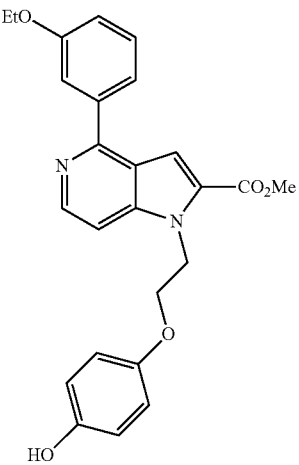 [SMILES: CCOc1cccc(-c2nccc3c2cc(C(=O)OC)n3CCOc2ccc(O)cc2)c1]

Methyl 1-[2-(4-tert-butoxyphenoxy)ethyl]-4-(3-ethoxyphenyl)-1H-pyrrolo[3,2-c]pyridine-2-carboxylate (900 mg, 1.842 mmole) was taken up in TFA (10 mL) at RT. After 3 hr the mixture was concentrated. The residue was taken up in saturated NaHCO$_3$ and extracted with EtOAc (3 x). The combined organic layers were dried (MgSO$_4$), filtered, and concentrated. Flash column chromatography (Biotage-SNAP-25 g SiO$_2$, 50% EtOAc/hexanes) gave the title compound (637 mg, 80%) as an off-white solid. $^1$H NMR (400 MHz, CDCl$_3$): δ 8.49 (d, J=6.0 Hz, 1 H); 7.60 (s, 1 H); 7.52-7.38 (m, 4 H); 7.01 (dd, J=8.2, 2.5 Hz, 1 H); 6.68-6.60 (m, 3 H); 5.72 (s, 1 H); 4.97-4.91 (m, 2 H); 4.33-4.27 (m, 2 H); 4.12 (dd, J=13.9, 7.0 Hz, 2 H); 3.93 (s, 3 H); 1.43 (t, J=7.0 Hz, 3 H).

Step 2:: 4-(3-Ethoxyphenyl)-1-{2-[4-(pyridin-3-yloxy)phenoxy]ethyl}-1H-pyrrolo[3,2-c]pyridine-2-carboxylic acid Methyl 4-(3-ethoxyphenyl)-1-[2-(4-hydroxyphenoxy)ethyl]-1H-pyrrolo[3,2-c]pyridine-2-carboxylate (30 mg, 0.069 mmole), Cs$_2$CO$_3$ (46 mg, 0.141 mmole), and CuCl (1 mg, 10.10 mol) were combined in a screw cap vial. To this was added NMP (0.4 mL) then 3-bromopyridine (10 μl, 0.104 mmole) and 2,2,6,6-tetramethyl-3,5-heptanedione (6 μl, 0.029 mmole). N$_2$ was bubbled through the mixture for 10 seconds. The vial was capped then heated to 120° C. After stirring overnight the mixture was cooled to RT then acidified with TFA. The mixture was filtered using a 0.45 μm PTFE syringe filter then purified by preparative reversed-phase HPLC (21×100 mm Phenomenex AXIA-Gemini-NX, 5%-30% CH$_3$CN/water containing 0.1% TFA over 18 min at 20 mL/min) to give the TFA salt of the title compound (20 mg, 47%) as an off-white foam. $^1$H NMR (499 MHz, DMSO): δ 8.62 (d, J=6.6 Hz, 1 H); 8.30 (m, 2 H); 7.64-7.61 (m, 2 H); 7.53-7.49 (m, 2 H); 7.38 (m, 1 H); 7.00 (d, J=8.96 Hz, 2 H); 6.86 (d, J=8.96 Hz, 2 H); 5.20 (m, 2 H); 4.40 (m, 2 H); 4.17 (q, J=7.04 Hz, 2 H); 1.39 (t, J=7.04 Hz, 3H). HRMS (ESI) calc (M+H)$^+$=496.1867. found 496.1869.

The following compounds were synthesized according to the procedures described in Example 67 using the appropriate heterocyclic halides in step 2 and were isolated as their TFA salt.

| Example | Structure | Name | Obs. HRMS (M + H)$^+$ |
|---|---|---|---|
| 68 | 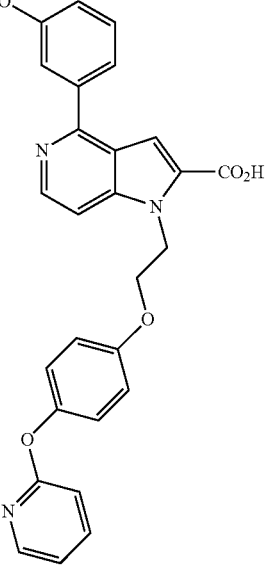 | 4-(3-ethoxyphenyl)-1-{2-[4-(pyridin-2-yloxy)phenoxy]ethyl}-1H-pyrrolo[3,2-c]pyridine-2-carboxylic acid | 496.1879 |
| 69 | 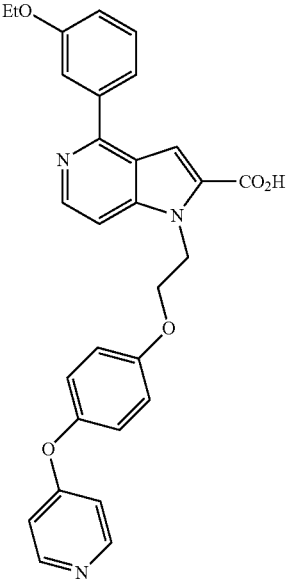 [SMILES: CCOc1cccc(-c2nccc3c2cc(C(=O)O)n3CCOc2ccc(Oc3ccncc3)cc2)c1] | 4-(3-ethoxyphenyl)-1-{2-[4-(pyridin-4-yloxy)phenoxy]ethyl}-1H-pyrrolo[3,2-c]pyridine-2-carboxylic acid | 496.1878 |

-continued
| Example | Structure | Name | Obs. HRMS (M + H)+ |
|---|---|---|---|
| 70 | 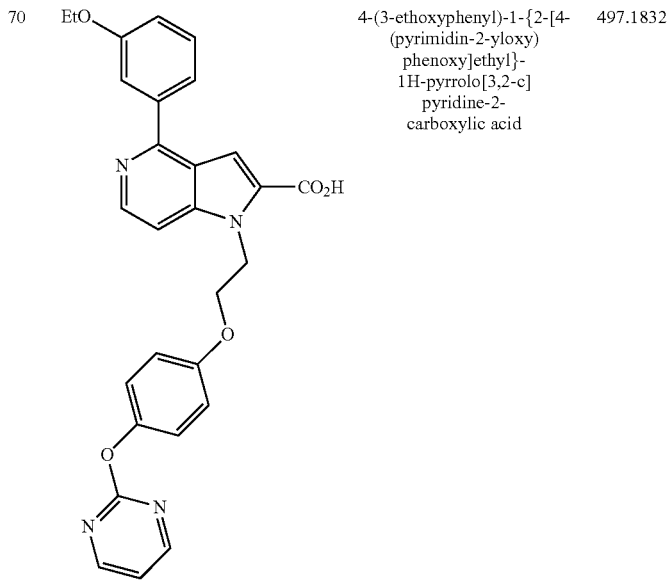 | 4-(3-ethoxyphenyl)-1-{2-[4-(pyrimidin-2-yloxy)phenoxy]ethyl}-1H-pyrrolo[3,2-c]pyridine-2-carboxylic acid | 497.1832 |
| 71 | 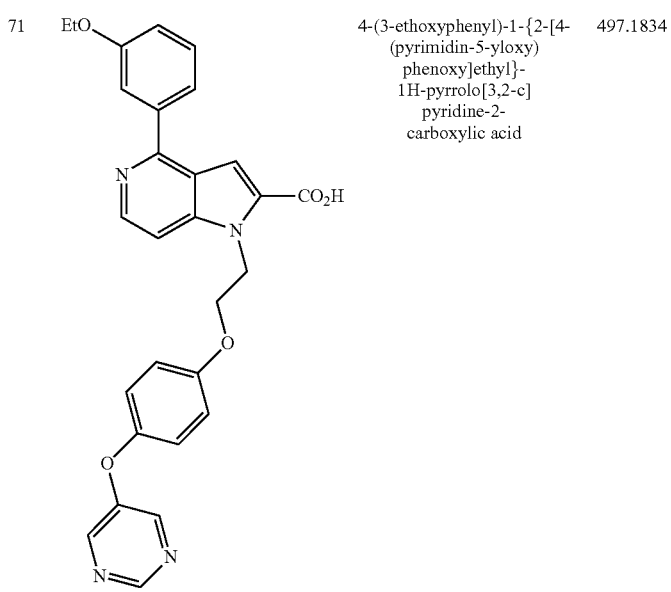 | 4-(3-ethoxyphenyl)-1-{2-[4-(pyrimidin-5-yloxy)phenoxy]ethyl}-1H-pyrrolo[3,2-c]pyridine-2-carboxylic acid | 497.1834 |

| Example | Structure | Name | Obs. HRMS (M + H)+ |
|---|---|---|---|
| 72 | 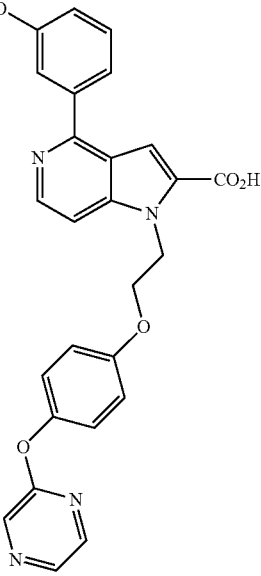 | 4-(3-ethoxyphenyl)-1-{2-[4-(pyrazin-2-yloxy)phenoxy]ethyl}-1H-pyrrolo[3,2-c]pyridine-2-carboxylic acid | 497.1832 |
| 73 | 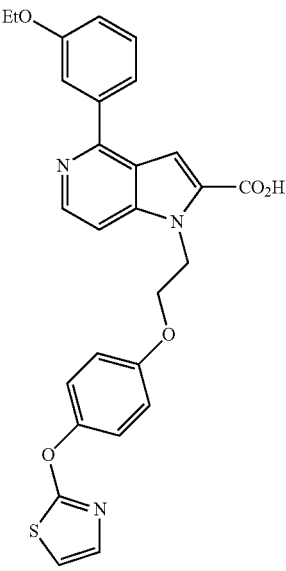 [SMILES: CCOc1cccc(-c2nccc3c2cc(C(=O)O)n3CCOc2ccc(Oc3nccs3)cc2)c1] | 4-(3-ethoxyphenyl)-1-{2-[4-(1,3-thiazol-2-yloxy)phenoxy]ethyl}-1H-pyrrolo[3,2-c]pyridine-2-carboxylic acid | 502.1440 |

Example 74

1-{2-[4-(Trifluoromethoxy)phenoxy]ethyl}-1H-pyrrolo[3,2-c]pyridine-2-carboxylic acid

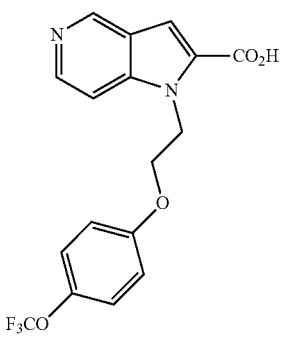 [SMILES: O=C(O)c1cc2cnccc2n1CCOc1ccc(OC(F)(F)F)cc1]

Methyl 4-chloro-1-{2-[4-(trifluoromethoxy)phenoxy]ethyl}-1H-pyrrolo[3,2-c]pyridine-2-carboxylate (25 mg, 0.060 mmole) was hydrogenated (balloon) with 10% Pd/C (10 mg, 9.40 μmol) in MeOH (3 mL) at RT. After 4 hr the mixture was filtered using a 0.45 μm PTFE syringe filter then concentrated. The residue was taken up in 0.5 mL MeOH. To this was added 2M NaOH (0.15 mL, 0.300 mmole) then the mixture was heated to 60° C. After stirring overnight the mixture was cooled to RT and concentrated. The crude material was taken up in DMSO and acidified with TFA. The resulting solution was filtered using a 0.45 μm PTFE syringe filter then purified by preparative reversed-phase HPLC (21× 100 mm Phenomenex AXIA-Gemini-NX, 20%-45% CH$_3$CN/water containing 0.1% TFA over 18 min at 20 mL/min) to give the TFA salt of the title compound (22 mg, 75%) as an off-white solid. $^1$H NMR (499 MHz, DMSO): δ 9.36 (s, 1 H); 8.58 (d, J=6.7 Hz, 1 H); 8.26 (d, J=6.8 Hz, 1 H); 7.70 (s, 1 H); 7.22 (d, J=8.5 Hz, 2H); 6.87 (d, J=8.6 Hz, 2 H); 5.14 (m, 2 H); 4.38 (m, 2 H). HRMS (ESI) calc (M+H)$^+$= 367.0900. found 367.0907.

Example 75

5-cyano-1-{2-[4-(trifluoromethoxy)phenoxy]ethyl}-1H-indole-2-carboxylic acid

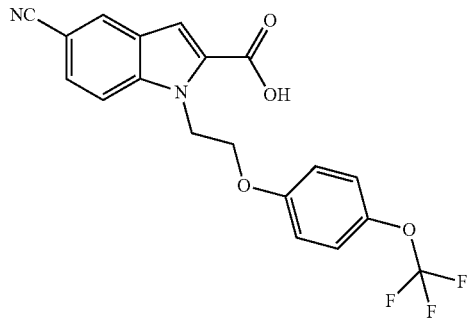 [SMILES: N#Cc1ccc2c(c1)cc(C(=O)O)n2CCOc1ccc(OC(F)(F)F)cc1]

To a solution Ethyl 5-cyano-1H-indole-2-carboxylate (37 mg, 0.173 mmol), 2-[4-(trifluoromethoxy) phenoxy]ethanol (42 mg, 0.19 mmol) and Triphenylphosphine (227 mg, 0.518 mmol) in toluene (1 mL) was add DIAD (0.044 ml, 0.225 mmol) dropwise at RT. The reaction was let to stir overnight. The mixture was diluted with EtOAc and quenched with water. The two layers were separated, and the aqueous phase was further extracted twice with EtOAc. The combined organic layers were washed with brine, dried (Na$_2$SO$_4$), filtered and concentrated in vacuo. The residue was purified by normal phase silica chromatography. The eluting solvent was 0-30% EtOAc in Hexanes. The isolated ethyl 5-cyano-1-{2-[4-(trifluoromethoxy)phenoxy]ethyl}-1H-indole-2-carboxylate (15 mg, 0.04 mmol) was dissolved in THF (1 mL), MeOH (300 uL) and 1M NaOH (200 uL). The reaction went to completion in 5 hr. Water was added, the pH was adjusted to 3 with 1N HCl, and the solvent was removed in vacuo. EtOAc was added to the resulting aqueous solution. The two layers were separated, and the aqueous phase was further extracted twice with EtOAc. The combined organic layers were washed with brine, dried (Na$_2$SO$_4$), filtered and concentrated in vacuo to yield 13.4 mg of the title product. HRMS: Calc for C$_{19}$H$_{13}$F$_3$N$_2$O$_4$ 413.0720. Found 413.0718

Example 76

Preparation of 5-(1H-pyrazol-4-yl)-1-{2-[4-(trifluoromethoxy)phenoxy]ethyl}-1H-indole-2-carboxylic acid

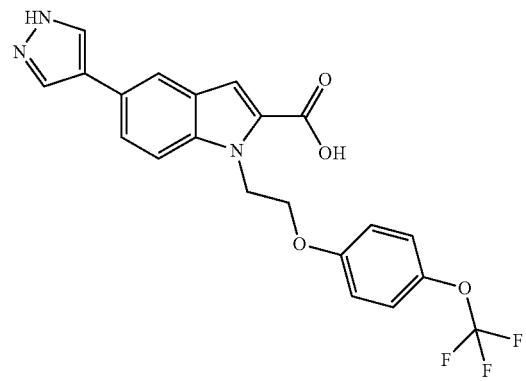 [SMILES: O=C(O)c1cc2cc(-c3cn[nH]c3)ccc2n1CCOc1ccc(OC(F)(F)F)cc1]

Step 1: Ethyl 5-[1-(tert-butoxycarbonyl)-1H-pyrazol-4-yl]-1H-indole-2-carboxylate

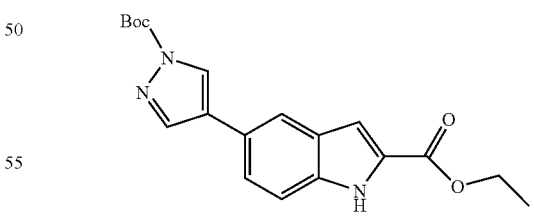

To a degassed solution of tert-butyl 4-(4,4,5,5-tetramethyl-1,3,2-dioxaborolan-2-yl)-1H-pyrazole-1-carboxylate (138 mg, 0.47 mmol), 5-bromo-indole (63 mg, 0.24 mmol), CsF (107 mg, 0.71 mmol), and X-Phos (11.2 mg, 0.023 mmol) in dioxane (2 mL) was added palladium acetate (2.6 mg, 0.012 mmol) under nitrogen. The mixture was then heated to 90 C overnight, cooled to r.t., and diluted with EtOAc. Following filtration and concentration in vacuo, the residue was purified on silica (0-30% EtOAc/hexanes) to yield the title product.

Step 2: Preparation of 5-(1H-pyrazol-4-yl)-1-{2-[4-(trifluoromethoxy)phenoxy]ethyl}-1H-indole-2-carboxylic acid Ethyl 5-[1-(tert-butoxycarbonyl)-1H-pyrazol-4-yl]-1H-indole-2-carboxylate (140 mg, 0.394 mmol) was dissolved in DMF and treated with NaH (added all at once, 18.9 mg, 0.47 mmol) at RT. The mixture stirred for 15 min and 4-(2-chloroethyl)phenyl trifluoromethyl ether (100 mg, 0.45 mmol) was added as a solution in 3 mL of DMF. The mixture was heated to 6° C. overnight. The reaction was cooled and diluted with EtOAc and quenched with sat'd NH₄Cl. The two layers were separated. The organic layer was washed with brine, dried (Na₂SO₄), filtered and concentration in vacuo. The crude residue was purified on silica gel (0-90% EtOAc/hexanes) to yield the desired ethyl ester (50 mg) which was subsequently treated with 3M NaOH (0.5 mL) MeOH (0.5 mL) and THF (2 mL) and heated in an oil bath to 60 C for 1 h. Water was added, the pH was adjusted to 3 with 1N HCl, and the solvent was removed in vacuo. EtOAc was added to the resulting aqueous solution. The two layers were separated, and the aqueous phase was further extracted twice with EtOAc. The combined organic layers were washed with brine, dried (Na₂SO₄), filtered and concentrated in vacuo to yield 30 mg of the title product. HRMS: Calc for C21H16F3N3O4 432.1166. Found 432.1169

Example 77

Preparation 5-(pyrazin-2-yl)-1-{2-[4-(trifluoromethoxy)phenoxy]ethyl}-1H-indole-2-carboxylic acid

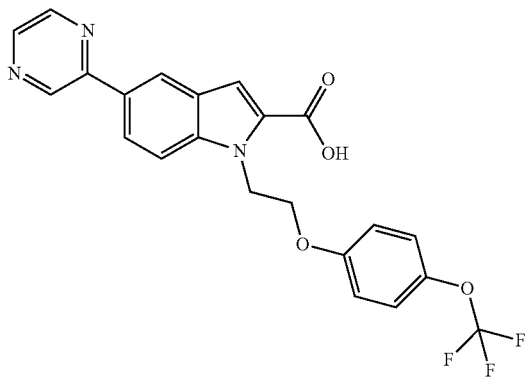 [SMILES: O=C(O)c1cc2cc(-c3cnccn3)ccc2n1CCOc1ccc(OC(F)(F)F)cc1]

Step 1: Ethyl 5-bromo-1-{2-[4-(trifluoromethoxy)phenoxy]ethyl}-1H-indole-2-carboxylate

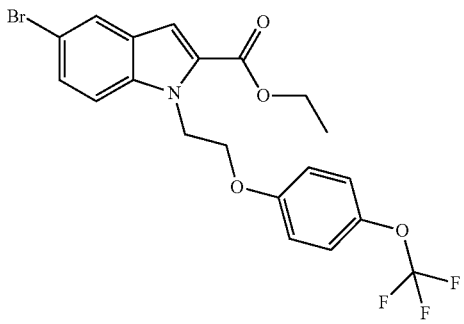 [SMILES: CCOC(=O)c1cc2cc(Br)ccc2n1CCOc1ccc(OC(F)(F)F)cc1]

To a solution of ethyl 5-bromo-1H-indole-2-carboxylate (1.7 g, 6.3 mmol), 2-[4-(trifluoromethoxy)phenoxy]ethanol (1.7 g, 7.6 mmol) and triphenylphosphine (3.3 g, 12.7 mmol) in toluene (20 ml) was added DIAD (1.85 ml, 9.5 mmol) dropwise at 0° C. The mixture was left to warm up to RT and stirred overnight. The mixture was then concentrated in vacuo. The residue was purified on silica gel (0-20% EtOAc in hexanes) to yield the title product (1.6 g).

Step 2: Ethyl 5-(4,4,5,5-tetramethyl-1,3,2-dioxaborolan-2-yl)-1-{2-[4-(trifluoromethoxy)phenoxy]ethyl}-1H-indole-2-carboxylate

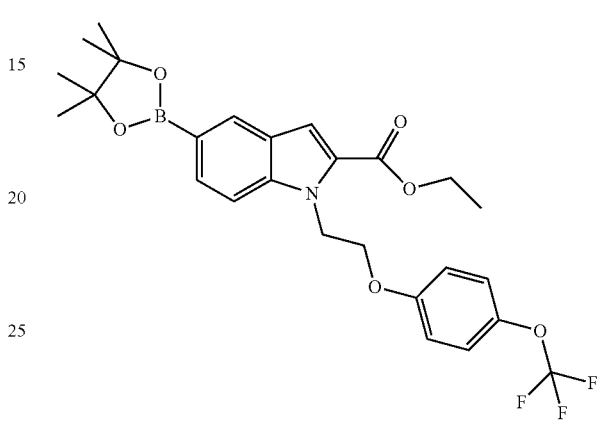

The ethyl 5-bromo-1-{2-[4-(trifluoromethoxy)phenoxy]ethyl}-1H-indole-2-carboxylate (812 mg, 1.7 mmol), pinacol borane (873 mg, 3.4 mmol), X Phos (98 mg, 0.21 mmol) and KOAc (540 mg, 5.5 mmol) were combined in 8 mL of Dioxane. The mixture was degassed under vacuum and backfilled with N2. Palladium acetate (23 mg, 0.1 mmol) was added, and the mixture was degassed and back filled again. The mixture was left to stir overnight at 85° C. EtOAc was added and the mixture was filtered through a pad of celite, concentrated in vacuo, and purified on silica (0-30% EtOAc in hexanes) to give the title product (675 mg).

Step 3: Preparation 5-(pyrazin-2-yl)-1-{2-[4-(trifluoromethoxy)phenoxy]ethyl}-1H-indole-2-carboxylic acid Ethyl 5-(4,4,5,5-tetramethyl-1,3,2-dioxaborolan-2-yl)-1-{2-[4-(trifluoromethoxy)phenoxy]ethyl}-1H-indole-2-carboxylate (34 mg, 0.065 mmol), 2-bromoprazine (21 mg, 0.13 mmol), K₂CO₃ (27 mg, 0.2 mmol) and S Phos (2.7 mg, 0.006 mmol) were combined in 1.0 mL of dioxane in a flask. The reaction was degassed and filled with nitrogen. Water (0.2 mL) was added and purged again with nitrogen. Palladium acetate (0.7 mg, 0.003 mmol) was added, and the reaction was heated to 90° C. overnight. EtOAc was added and the crude mixture was filtered through a pad of Celite. The volatiles were concentrated in vacuo, and the reaction was purified on reverse phase HPLC (25-55% ACN in H2O (w/0.1% TFA)) to yield the title product. HRMS: Calc for C₂₂H₁₇F₃N₃O₄ 444.1171. Found 444.1167

The following compounds were prepared according to the procedure for Example 77 using the appropriate boronic acids/esters in steps 3

| Example | Structure | Name | Obs. HRMS/LRMS |
|---|---|---|---|
| 78 | 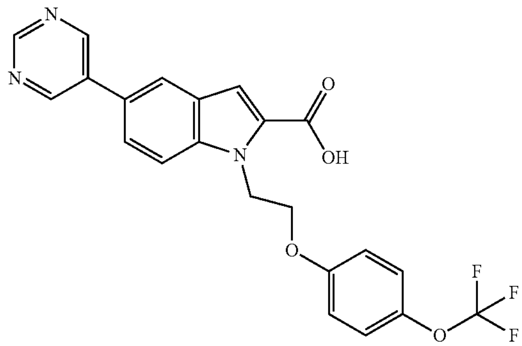 [SMILES: O=C(O)c1cc2cc(-c3cncnc3)ccc2n1CCOc1ccc(OC(F)(F)F)cc1] | 5-pyrimidin-5-yl-1-{2-[4-(trifluoromethoxy)phenoxy]ethyl}-1H-indole-2-carboxylic acid | 444.1162 |
| 79 | 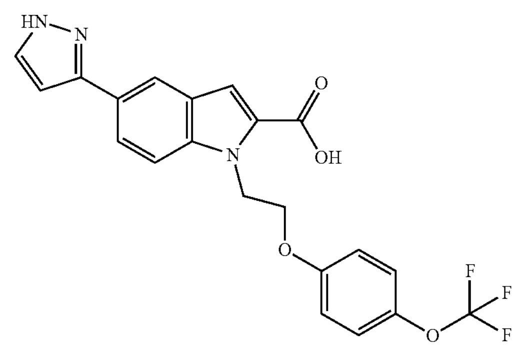 [SMILES: O=C(O)c1cc2cc(-c3cc[nH]n3)ccc2n1CCOc1ccc(OC(F)(F)F)cc1] | 5-(1H-pyrazol-3-yl)-1-{2-[4-(trifluoromethoxy)phenoxy]ethyl}-1H-indole-2-carboxylic acid | 432.1183 |
| 80 | 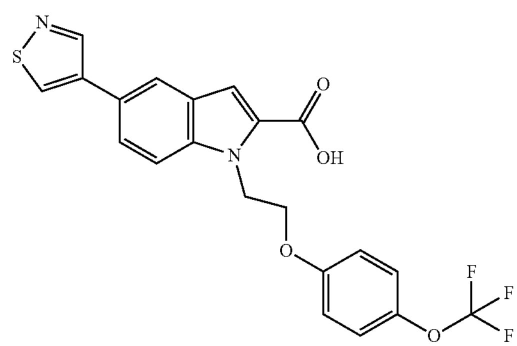 [SMILES: O=C(O)c1cc2cc(-c3cnsc3)ccc2n1CCOc1ccc(OC(F)(F)F)cc1] | 5-isothiazol-4-yl-1-{2-[4-(trifluoromethoxy)phenoxy]ethyl}-1H-indole-2-carboxylic acid | 449.0777 |
| 81 | 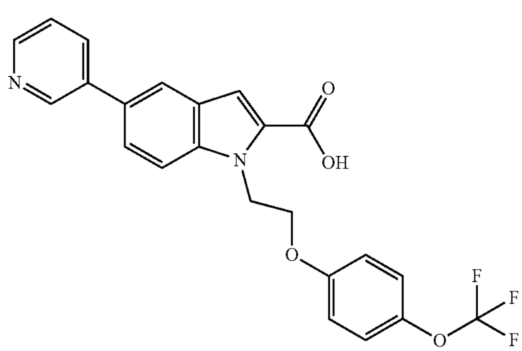 [SMILES: O=C(O)c1cc2cc(-c3cccnc3)ccc2n1CCOc1ccc(OC(F)(F)F)cc1] | 5-pyridin-3-yl-1-{2-[4-(trifluoromethoxy)phenoxy]ethyl}-1H-indole-2-carboxylic acid | 443.1235 |

| Example | Structure | Name | Obs. HRMS/LRMS |
|---------|-----------|------|----------------|
| 82 | 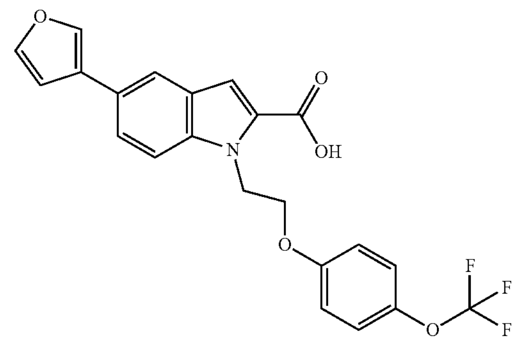 [SMILES: O=C(O)c1cc2cc(-c3ccoc3)ccc2n1CCOc1ccc(OC(F)(F)F)cc1] | 5-furan-3-yl-1-{2-[4-(trifluoromethoxy)phenoxy]ethyl}-1H-indole-2-carboxylic acid | 432.2 |
| 83 | 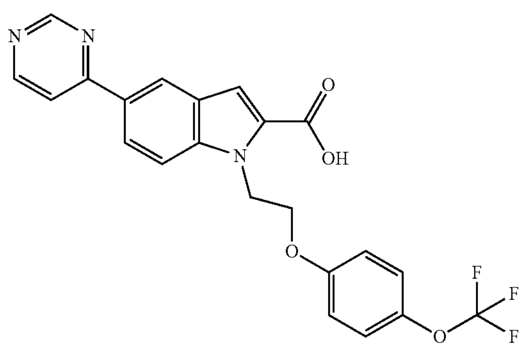 [SMILES: O=C(O)c1cc2cc(-c3ccncn3)ccc2n1CCOc1ccc(OC(F)(F)F)cc1] | 5-pyrimidin-4-yl-1-{2-[4-(trifluoromethoxy)phenoxy]ethyl}-1H-indole-2-carboxylic acid | 444.1163 |
| 84 | 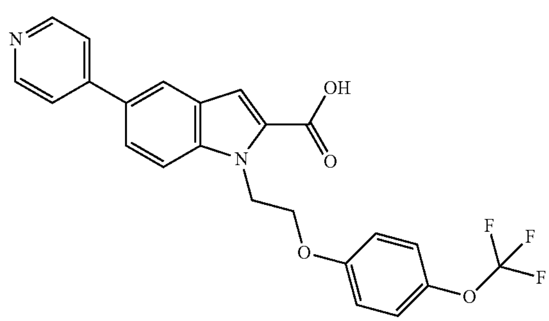 [SMILES: O=C(O)c1cc2cc(-c3ccncc3)ccc2n1CCOc1ccc(OC(F)(F)F)cc1] | 5-pyridin-4-yl-1-{2-[4-(trifluoromethoxy)phenoxy]ethyl}-1H-indole-2-carboxylic acid | 443.1209 |
| 85 | 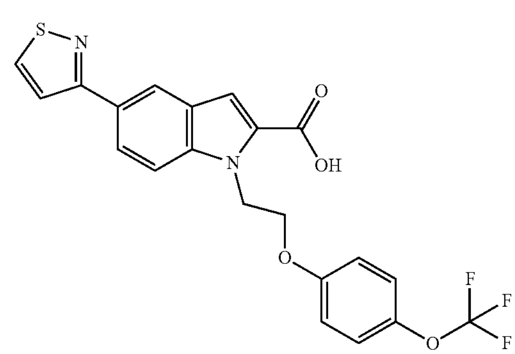 [SMILES: O=C(O)c1cc2cc(-c3ccsn3)ccc2n1CCOc1ccc(OC(F)(F)F)cc1] | 5-isothiazol-3-yl-1-{2-[4-(trifluoromethoxy)phenoxy]ethyl}-1H-indole-2-carboxylic acid | 449.0773 |

| Example | Name | Obs. HRMS/LRMS |
|---|---|---|
| 86 | 5-(1,3-thiazol-2-yl)-1-{2-[4-(trifluoromethoxy)phenoxy]ethyl}-1H-indole-2-carboxylic acid | 449.0786 |
| 87 | 5-(1,3-thiazol-4-yl)-1-{2-[4-(trifluoromethoxy)phenoxy]ethyl}-1H-indole-2-carboxylic acid | 449.0777 |
| 88 | 5-pyridin-2-yl-1-{2-[4-(trifluoromethoxy)phenoxy]ethyl}-1H-indole-2-carboxylic acid | 443.1208 |
| 89 | 5-furan-2-yl-1-{2-[4-(trifluoromethoxy)phenoxy]ethyl}-1H-indole-2-carboxylic acid | 432.1050 |

Example 90

7-chloro-3-{2-[4-(trifluoromethoxy)phenoxy]ethyl}-1H-pyrrolo[2,3-c]pyridine-2-carboxylic acid

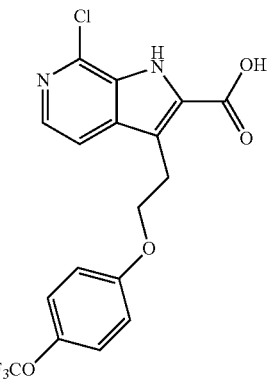

Step 1: 7-chloro-3-iodo-1H-pyrrolo[2,3-c]pyridine

To a mixture of 7-chloro-1H-pyrrolo[2,3-c]pyridine (0.75 g, 4.92 mmol) and N-iodo-succinimide (1.2 g, 5.41 mmol) was added acetonitrile (31 mL) and the solution was heated to 75 C. After 1 h, the mixture was cooled to r.t., the formed solid was filtered, washed with acetonitrile, and dried to yield the title product (1.2 g). HRMS (ESI) calc $(M+H)^+=278.9180$. found 278.9181.

Steps 2: tert-butyl 7-chloro-3-iodo-1H-pyrrolo[2,3-c]pyridine-1-carboxylate

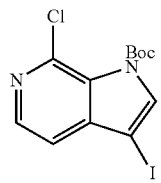

To a solution of 7-chloro-3-iodo-1H-pyrrolo[2,3-c]pyridine (1.2 g, 4.27 mmol) in THF (28.5 mL) cooled to 0 C was added NaH (0.26 g, 6.4 mmol, 60% dispersion). The mixture was then warmed to r.t., stirred 1 h, and then cooled back to 0 C. Boc$_2$O (1.1 mL, 4.7 mmol) was then added and the mixture was warmed back to r.t. After 2 h, EtOAc was added and the mixture was extracted with water 2×. The organic layer was dried over MgSO$_4$, filtered, and concentrated in vacuo. The crude material was purified on silica (gradient elution, 0-20% EtOAc/hexanes) to yield the title product (1.56 g). HRMS (ESI) calc $(M+H)^+=378.9705$. found 378.9692.

Step 3: tert-butyl 3-(2-tert-butoxy-2-oxoethyl)-7-chloro-1H-pyrrolo[2,3-c]pyridine-1-carboxylate

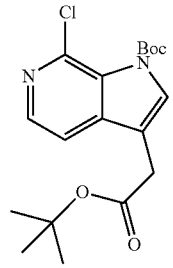 [SMILES: CC(C)(C)OC(=O)Cc1cn(C(=O)OC(C)(C)C)c2c(Cl)nccc12]

To a solution of tert-butyl 7-chloro-3-iodo-1H-pyrrolo[2,3-c]pyridine-1-carboxylate (500 mg, 1.3 mmol), bis-(tert-butyl-phosphine) palladium (67.5 mg, 0.13 mmol), and palladium acetate (7.4 mg, 0.003 mmol) in THF (10 mL) was added (2-tert-butoxy-2-oxoethyl)(chloro)zinc (6.6 mL, 3.3 mmol, 0.5 M in diethyl ether). The mixture was then heated to 50 C overnight, cooled to r.t. and quenched by addition of MeOH (1 mL). EtOAc was added and the solution was extracted with 5% KHSO$_4$. The organic layer was dried over MgSO$_4$, filtered, and concentrated in vacuo. The crude material was purified on silica (gradient elution, 0-25% EtOAc/hexanes) to yield the title product (382 mg). HRMS (ESI) calc $(M+H)^+=367.1419$. found 367.1422.

Step 4: tert-butyl 7-chloro-3-(2-hydroxyethyl)-1H-pyrrolo[2,3-e]pyridine-1-carboxylate

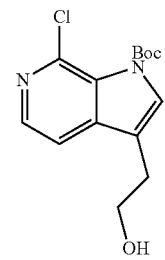

To a solution of tert-butyl 3-(2-tert-butoxy-2-oxoethyl)-7-chloro-1H-pyrrolo[2,3-c]pyridine-1-carboxylate (382 mg, 1.0 mmol) in THF (10 mL) was added DIBAL (3.12 mL, 3.12 mmol, 1 M in THF) at −78 C. The reaction was then warmed to r.t. and stirred for 15 min. Water (0.13 mL), 15 wt % NaOH (0.13 mL), and additional water (0.3 mL) was then added sequentially. After warming to r.t. and stirring 15 min, MgSO4 was added and stirring was continued for 15 min. The mixture was then filtered and concentrated in vacuo. The crude material was purified on silica (gradient elution, 0-100% EtOAc/hexanes) to yield the title product (233 mg). HRMS (ESI) calc $(M+H)^+=297.1000$. found 297.0994.

Step 5: tert-butyl 7-chloro-3-{2-[4-(trifluoromethoxy)phenoxy]ethyl}-1H-pyrrolo[2,3-c]pyridine-1-carboxylate

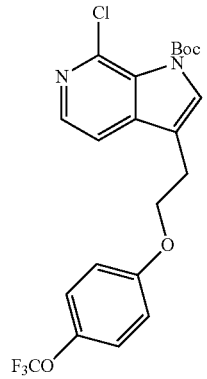 [SMILES: CC(C)(C)OC(=O)n1cc(CCOc2ccc(OC(F)(F)F)cc2)c2ccnc(Cl)c21]

To a solution of tert-butyl 7-chloro-3-(2-hydroxyethyl)-1H-pyrrolo[2,3-c]pyridine-1-carboxylate (233 mg, 0.79 mmol) in PhMe (15 mL) was added 4-trifluoromethoxyphenol (0.15 mL, 1.2 mmol), triphenylphosphine (309 mg, 1.2 mmol), and diisopropylazodicarboxylate (0.23 mL, 1.2 mmol) at r.t. After 20 min, the mixture was concentrated in vacuo, and the crude material was purified on silica (gradient elution, 0-30% EtOAc/hexanes) to yield the title product (349 mg). HRMS (ESI) calc (M+H)$^+$=457.1136. found 457.1133.

Step 6: 1-tert-butyl 2-ethyl 7-chloro-3-{2-[4-(trifluoromethoxy)phenoxy]ethyl}-1H-pyrrolo[2,3-c]pyridine-1,2-dicarboxylate

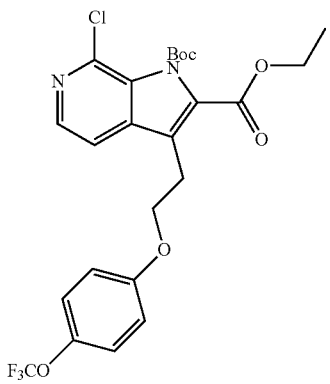 [SMILES: CCOC(=O)c1c(CCOc2ccc(OC(F)(F)F)cc2)c2ccnc(Cl)c2n1C(=O)OC(C)(C)C]

To solution of tert-butyl 7-chloro-3-{2-[4-(trifluoromethoxy)phenoxy]ethyl}-1H-pyrrolo[2,3-c]pyridine-1-carboxylate (349 mg, 0.76 mmol) in THF (15 mL) cooled to −78 C was added LDA (0.57 mL, 1.1 mmol, 2 M). After 30 min at this temperature, ethyl chloroformate (0.15 mL, 1.5 mmol) was added and the mixture was warmed to r.t. slowly. The reaction mixture was then quenched with 5% potassium bisulfate and extracted with EtOAc. The organic layer was dried over MgSO$_4$, filtered, and concentrated in vacuo. The crude material was purified on silica (gradient elution, 0-30% EtOAc/hexanes) to yield the title product (362 mg). HRMS (ESI) calc (M+H)$^+$=529.1348. found 529.1346.

Step 7: 1-(tert-butoxycarbonyl)-7-chloro-3-{2-[4-(trifluoromethoxy)phenoxy]ethyl}-1H-pyrrolo[2,3-c]pyridine-2-carboxylic acid

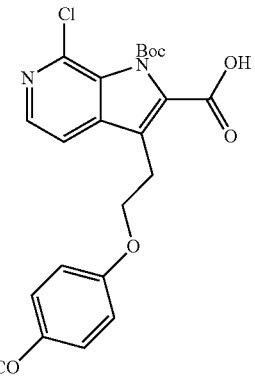

To a solution of 1-tert-butyl 2-ethyl 7-chloro-3-{2-[4-(trifluoromethoxy)phenoxy]ethyl}-1H-pyrrolo[2,3-c]pyridine-1,2-dicarboxylate (33 mg, 0.06 mmol) in THF (1 mL) was added EtOH (0.2 mL)$_m$ and water (0.2 mL). Solid LiOH (30 mg, 1.2 mmol) was then added in a single portion. After 2.5 h, quenched with 5% potassium bisulfate until acidic (~pH 3) and extracted with Et$_2$O and then EtOAc. The combined organic layer was dried over MgSO$_4$, filtered, and concentrated in vacuo to yield the title compound (30 mg). LRMS (ESI) calc (M+H)$^+$=501.1. found 501.2.

Step 8: 7-chloro-3-{2-[4-(trifluoromethoxy)phenoxy]ethyl}-1H-pyrrolo[2,3-c]pyridine-2-carboxylic acid To a solution of 1-(tert-butoxycarbonyl)-7-chloro-3-{2-[4-(trifluoromethoxy)phenoxy]ethyl}-1H-pyrrolo[2,3-c]pyridine-2-carboxylic acid (9.4 mg, 0.019 mmol) in DCM (0.5 mL) was added water (0.01 mL), dimethylsulfide (0.01 mL), and then TFA (0.5 mL, 6.5 mmol). Upon complete consumption of starting material, the mixture was concentrated in vacuo to yield the title compound as a TFA salt (7.8 mg). HRMS (ESI) calc (M+H)$^+$=401.0510. found 401.0509.

Example 91

7-(3-ethoxyphenyl)-3-{2-[4-(trifluoromethoxy)phenoxy]ethyl}-1H-pyrrolo[2,3-d]pyridine-2-carboxylic acid

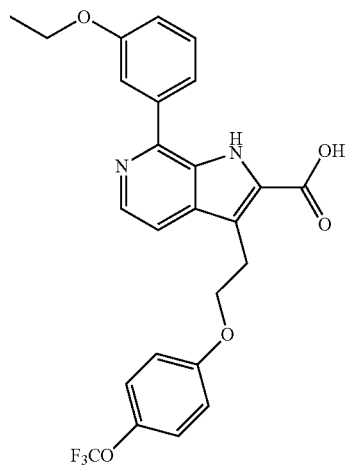 [SMILES: CCOc1cccc(-c2nccc3c(CCOc4ccc(OC(F)(F)F)cc4)c(C(=O)O)[nH]c23)c1]

Step 1: ethyl 7-(3-ethoxyphenyl)-3-{2-[4-(trifluoromethoxy)phenoxy]ethyl}-1H-pyrrolo[2,3-c]pyridine-2-carboxylate

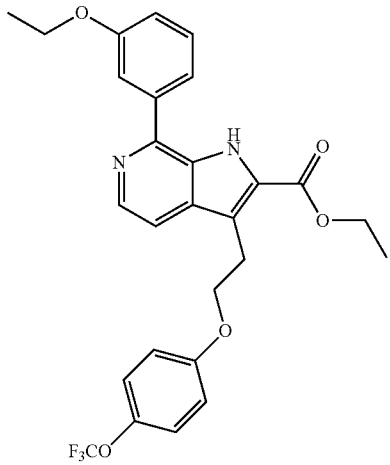 [SMILES: CCOC(=O)c1[nH]c2c(-c3cccc(OCC)c3)nccc2c1CCOc1ccc(OC(F)(F)F)cc1]

To a mixture of 1-tert-butyl 2-ethyl 7-chloro-3-{2-[4-(trifluoromethoxy)phenoxy]ethyl}-1H-pyrrolo[2,3-c]pyridine-1,2-dicarboxylate (88 mg, 0.17 mmol), 3-ethoxyphenylboronic acid (69 mg, 0.42 mmol), KF (38.7 mg, 0.67 mmol), and bis(tri-t-butylphosphine)palladium (0) (8.50 mg, 0.02 mmol) was added dioxane (3.5 mL) under a nitrogen atmosphere. The reaction was then heated to 100 C overnight. Another charge of 3-ethoxyphenylboronic acid (69 mg, 0.42 mmol), KF (38.7 mg, 0.67 mmol), and bis(tri-t-butylphosphine)palladium (0) (8.50 mg, 0.02 mmol) was then added and stirring was continued for 4 h. The crude reaction mixture was then concentrated in vacuo, and the crude material was purified on silica (gradient elution, 0-50% EtOAc/hexanes) to yield the title product (80 mg) as a mixture with Boc'd material 1-tert-butyl 2-ethyl 7-(3-ethoxyphenyl)-3-{2-[4-(trifluoromethoxy)phenoxy]ethyl}-1H-pyrrolo[2,3-c]pyridine-1,2-dicarboxylate. HRMS (ESI) calc (M+H)$^+$=515.1788. found 515.1772.

Step 2: 7-(3-ethoxyphenyl)-3-{2-[4-(trifluoromethoxy)phenoxy]ethyl}-1H-pyrrolo[2,3-c]pyridine-2-carboxylic acid To a solution of ethyl 7-(3-ethoxyphenyl)-3-{2-[4-(trifluoromethoxy)phenoxy]ethyl}-1H-pyrrolo[2,3-c]pyridine-2-carboxylate (80 mg, 0.15 mmol) in THF (2 mL) was added EtOH (0.4 mL)m and water (0.4 mL). Solid LiOH (75 mg, 3.1 mmol) was then added in a single portion. After 2 h at r.t. and 2 h at 50 C, the reaction was quenched with 5% potassium bisulfate until acidic (~pH 3) which caused a white precipitate to form. This was filtered and washed with water to yield the title compound (65 mg). HRMS (ESI) calc (M+H)$^+$=487.1475. found 487.1478.

Example 92

8-(3-ethoxyphenyl)-3-{2-[4-(trifluoromethoxy)phenoxy]ethyl}imidazo[1,2-a]pyrazine-2-carboxylic acid

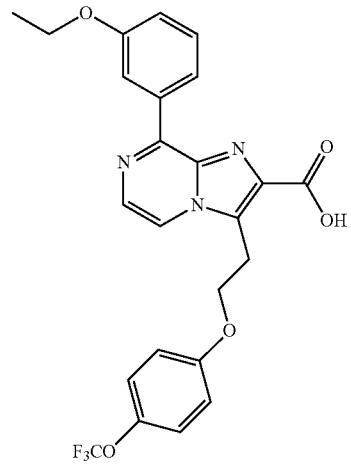 [SMILES: CCOc1cccc(-c2nccn3c(CCOc4ccc(OC(F)(F)F)cc4)c(C(=O)O)nc23)c1]

Step 1: methyl 8-chloroimidazo[1,2-a]pyrazine-2-carboxylate

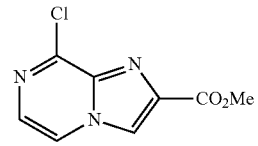

To a solution of 3-chloropyrazin-2-amine (52 g, 401 mmol) in acetonitrile (750 mL) under $N_2$ was added sodium bicarbonate (67.4 g, 803 mmol), and then methyl bromopyruvate (97 mL, 803 mmol). The mixture was then heated to 80° C. for 4 hours and then cooled to r.t. The reaction was then diluted water (2200 mL) and stirred for 30 minutes. The resulting solids were filtered, azeotroped with EtOAc (2 L), and dried overnight at 40° C. under vacuum and nitrogen sweep to give the title compound (60 g). LRMS (ESI) calc (M+H)$^+$=212.0. found 212.0

Step 2: methyl 3-bromo-8-chloroimidazo[1,2-a]pyrazine-2-carboxylate

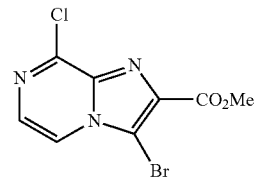 [SMILES: COC(=O)c1nc2c(Cl)nccn2c1Br]

To a solution of methyl 8-chloroimidazo[1,2-a]pyrazine-2-carboxylate (9.9 g, 46.8 mmol) in acetonitrile (600 mL) was added NBS (8.9 g, 50.1 mmol), and benzoyl peroxide (90 mg, 0.37 mmol). The mixture was then heated to reflux for 1 h, cooled to r.t., and water (1800 mL) was added. The resulting solids were filtered, washed with water, and air dried to give the title compound (11 g). LRMS (ESI) calc (M+H)$^+$=289.9/291.9. found 290.0/292.0

Step 3: methyl 8-chloro-3-(prop-2-en-1-yl)imidazo[1,2-a]pyrazine-2-carboxylate

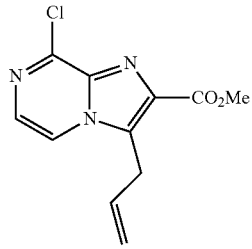 [SMILES: C=CCc1c(C(=O)OC)nc2c(Cl)nccn12]

To a suspension of methyl 3-bromo-8-chloroimidazo[1,2-a]pyrazine-2-carboxylate (250 mg, 0.861 mmol) in THF (8.6 mL) cooled to −40 C was added isopropylmagnesium chloride (0.99 mL, 1.29 mmol) dropwise. After 1 h stirring, copper cyanide (7.7 mg, 0.09 mmol) and allyl bromide (0.15 mL, 1.7 mmol) were added and the mixture was warmed to r.t. After 1 h, the reaction was poured into brine. The organic layer was separated, dried over MgSO$_4$, filtered, and concentrated in vacuo. The crude material was purified on silica (gradient elution, 0-80% EtOAc/hexanes) to yield the title product (48 mg). HRMS (ESI) calc (M+H)$^+$=252.0534. found 252.0539.

Step 4: methyl 8-chloro-3-(2-hydroxyethyl)imidazo[1,2-a]pyrazine-2-carboxylate

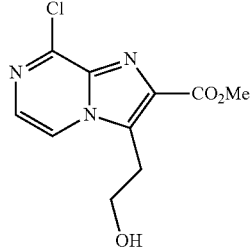 [SMILES: COC(=O)c1nc2c(Cl)nccn2c1CCO]

To a solution of methyl 8-chloro-3-(prop-2-en-1-yl)imidazo[1,2-a]pyrazine-2-carboxylate (48 mg, 0.191 mmol) in THF (1.5 mL) and water (0.300 mL) cooled to 0 C was added NMO (49.2 mg, 0.420 mmol) and osmium tetroxide (0.120 mL, 9.54 μmol, 2.5 wt %). The mixture was then warmed to r.t. and stirred 4 h. The mixture was then extracted with EtOAc and sodium thiosulfate.

The organic layer was separated, dried over MgSO$_4$, filtered, and concentrated in vacuo. To the crude material was added MeOH (1.5 mL), water (0.15 mL), and sodium periodate (135 mg, 0.629 mmol). After 2 h, the reaction was poured into EtOAc/water, the organic layer was separated, dried over MgSO$_4$, filtered, and concentrated in vacuo. To the crude material was added MeOH (1.5 mL) and sodium borohydride (10.8 mg, 0.286 mmol). After 5 min, the mixture was concentrated in vacuo and the crude material was purified on silica (gradient elution, 0-100% EtOAc/hexanes) to yield the title product (18 mg). HRMS (ESI) calc (M+H)$^+$=256.0483. found 256.0485.

Step 5: methyl 8-chloro-3-{2-[4-(trifluoromethoxy)phenoxy]ethyl}imidazo[1,2-a]pyrazine-2-carboxylate

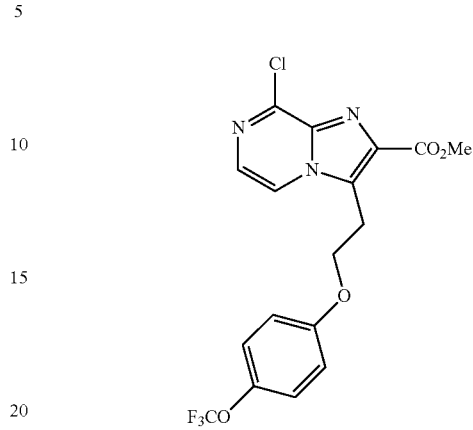

To a suspension of methyl 8-chloro-3-(2-hydroxyethyl)imidazo[1,2-a]pyrazine-2-carboxylate (18 mg, 0.070 mmol) in toluene (1 mL) was added 4-trifluoromethoxyphenol (0.014 mL, 0.106 mmol), Ph$_3$P (27.7 mg, 0.106 mmol), and DIAD (0.021 mL, 0.106 mmol). After 30 min, the reaction was concentrated in vacuo and then purified on silica (gradient elution, 0-100% EtOAc/hexanes) to yield the title product (10 mg). HRMS (ESI) calc (M+H)$^+$=416.0619. found 416.0616.

Step 6: methyl 8-(3-ethoxyphenyl)-3-{2-[4-(trifluoromethoxy)phenoxy]ethyl}imidazo[1,2a]-pyrazine-2-carboxylate

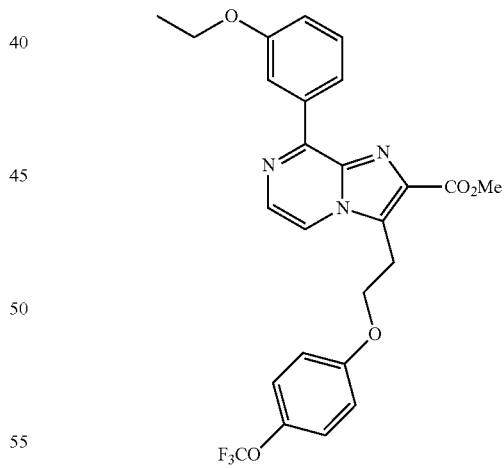

To a mixture of methyl 8-chloro-3-{2-[4-(trifluoromethoxy)phenoxy]ethyl}imidazo[1,2-a]pyrazine-2-carboxylate (10 mg, 0.024 mmol), 3-ethoxyphenylboronic acid (10 mg, 0.060 mmol), potassium fluoride (5.56 mg, 0.096 mmol), and bis(tri-t-butylphosphine)palladium (1.2 mg, 2.405 μmol) was added dioxane (1 mL). The reaction was then heated to 100 C overnight. The reaction was the concentrated in vacuo and then purified on silica (gradient elution, 0-80% EtOAc/hexanes) to yield the title product (5 mg). HRMS (ESI) calc (M-FH)$^+$=502.1584. found 502.1562.

Step 7: 8-(3-ethoxyphenyl)-3-{2-[4-(trifluoromethoxy)phenoxy]ethyl}imidazo[1,2-a]pyrazine-2-carboxylic acid To a solution of methyl 8-(3-ethoxyphenyl)-3-{2-[4-(trifluoromethoxy)phenoxy]ethyl}imidazo[1,2-c]pyrazine-2-carboxylate (5 mg, 0.01 mmol) in THF (1 mL), MeOH (0.2 mL), and water (0.2 mL) was added LiOH (4.78 mg, 0.199 mmol) at r.t. After 2 h, 5% KHSO$_4$ was added until acidic (pH~3), and then the mixture was extracted with Et$_2$O and then EtOAc. The organic layers were then dried over MgSO$_4$, filtered and concentrated in vacuo to yield the title product. HRMS (ESI) calc (M+H)$^+$=488.1428. found 488.1411.
Biological Utility TrkA kinase activity was measured as the ability of the enzyme to phosphorylate a fluorescently labeled peptide substrate. Buffer salts, reagents, and fluorescently labeled peptides were purchased from Carna Biosciences and were of the highest quality available (QSS Assist TRICA_MSA Kit). Enzyme was purchased from Cell Signaling, and was used without further purification. 384-well round bottom assay plates were prepared by the addition of 200 ml of a DMSO solution of compound at various concentrations to final inhibitor concentrations ranging from 100 μM to 0.2 μM. Next, assay buffer (10 μl) containing substrate and ATP were added, followed by addition of 10 μl of enzyme in assay buffer. Final assays concentrations were: [E]=0.37 nM, [S]=1 μM, [ATP]=2 mM. The reactions were incubated at room temperature for 3 hours resulting in approximately 15% substrate phosphorylation and were terminated by the addition of 5 μl of stop buffer. Substrates and products were separated on the Caliper EZReader II (Caliper LifeSciences, Inc.) using standard separation protocols. The percent inhibition was calculated for each compound concentration and the IC$_{50}$ was determined using equation 1.

$$\% \text{ Inhibition} = \left( \text{Max} + \frac{(\text{Max} - \text{Min})}{1 + \left(\frac{Conc}{IC_{50}}\right)^{Hill}} \right) \quad \text{Equation 1}$$

IC50 values from the aforementioned assay for the compounds of this invention range between 20 nM to 100 μM, preferably 20 nM to 10000 nM. IC50 values for particular compounds of this invention are provided below in Table 2 below:

TABLE 2

| Ex | Trk A EC50 (nM) |
|---|---|
| 58 | 30710 |
| 91 | 34.9 |
| 73 | 775.7 |
| 92 | 1214 |
| 57 | 162 |
| 38 | 3923 |
| 16 | 5358 |
| 78 | 38.7 |
| 76 | 28.5 |
| 81 | 469.5 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula I:

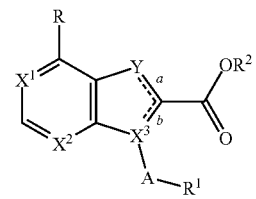

or a pharmaceutically acceptable salt thereof, wherein
——— is a bond that when present forms a double bond with bond a or bond b;
X$^1$ is —N or —N$^+$—O$^-$;
X$^2$ is —CH;
X$^3$ is —N;
Y is —CH;
——— is present at a;
R is a C$_{6-10}$ aryl, C$_{5-10}$ heteroaryl, said aryl and heteroaryl optionally substituted with 1 to 3 groups of R$^a$;
R$^1$ is a (CH$_2$)$_n$C$_{6-10}$ aryl, (CH$_2$)$_n$C$_{5-10}$ heteroaryl, and C$_{5-10}$ heterocyclyl, said heterocyclyl selected from pyrrolidinyl, oxopyrrolidinyl, piperidinyl, or hydrogen, said aryl, heteroaryl, pyrrolidinyl, oxopyrrolidinyl, and piperidinyl optionally substituted with 1 to 3 groups of R$^b$;
R$^2$ is hydrogen, or C$_{1-6}$ alkyl;
A is C$_{1-6}$ alkyl, C$_{2-6}$ alkenyl, C$_{2-6}$ alkynyl, —(CH$_2$)$_n$O—, —CH$_2$C(O)NH—, —O—, or —NR$^2$—;
R$^3$ is hydrogen, CN, or C$_{5-10}$ heterocyclyl, said heterocyclyl optionally substituted with 1 to 3 groups of R$^a$;
R$^a$ is —CN, —C$_{1-4}$haloalkyl, halo, —C$_{1-6}$alkyl, —OR, —NR$^2$R$^2$, or —NH(CH$_2$)$_n$OH;
R$^b$ is —CN, —C$_{1-4}$haloalkyl, —OC$_{1-4}$haloalkyl, —O(CH$_2$)$_n$haloalkyl, —C$_{1-6}$alkyl, —C$_{2-6}$alkenyl, —C$_{2-6}$alkynyl, —(CH$_2$)$_n$C$_{6-10}$ aryl, —(CH$_2$)$_n$C$_{5-10}$ heterocyclyl, —(CH$_2$)$_n$O—C$_{6-10}$ aryl, —(CH$_2$)$_n$O—C$_{5-10}$ heterocyclyl, —C(O)C$_{6-10}$aryl, —NHC$_{6-10}$aryl, halo, —OR, —NR$^2$R$^2$, or SO$_2$R$^2$, said aryl and heterocyclyl optionally substituted with 1 to 3 groups of R$^a$; and
n is 0, 1, 2, 3, or 4.
2. The compound according to claim 1 wherein R$^2$ is hydrogen.
3. The compound according to claim 2 wherein A is selected from the group consisting of C$_{1-6}$ alkyl, —(CH$_2$)$_n$O—, and —NR$^2$—.
4. The compound according to claim 1 wherein R$^1$ is optionally substituted phenyl, oxadiazolyl, pyrazolyl, thiazolyl, oxazolyl, quinolinyl, isoquinolinyl, pyridyl, pyrrolidinyl, oxopyrrolidinyl, piperidinyl, and pyrimidinyl.
5. The compound according to claim 4 wherein R$^1$ is phenyl.
6. The compound according to claim 1 wherein R is phenyl, quinolinyl, indolyl, isoquinolinyl, pyridyl, thiazolyl, and pyrimidinyl wherein said phenyl, quinolinyl, indolyl, isoquinolinyl, pyridyl, thiazolyl, and pyrimidinyl is optionally substituted with 1 to 3 groups of R$^a$.
7. The compound according to claim 6 wherein R is optionally substituted phenyl.

8. The compound according to claim 1 represented by formula II:

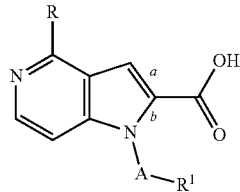

or a pharmaceutically acceptable salt thereof, wherein:
R is phenyl, quinolinyl, indolyl, isoquinolinyl, pyridyl, thiazolyl, or pyrimidinyl, wherein said phenyl, quinolinyl, indolyl, isoquinolinyl, pyridyl, thiazolyl, or pyrimidinyl is optionally substituted with 1 to 3 groups of $R^a$,
A is —(CH$_2$)$_n$O— or C$_{1-6}$ alkyl, and
$R^1$ is phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl, wherein said phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl is optionally substituted with 1 to 3 groups of $R^b$.

9. The compound according to claim 8 wherein R is optionally substituted phenyl, A is —(CH$_2$)$_n$O—, and $R^1$ is optionally substituted phenyl.

10. The compound according to claim 1 wherein $X^1$ is —N.

11. The compound according to claim 1 or a pharmaceutically acceptable salt thereof, wherein
$X^1$ is —N$^+$—O$^-$;
R is phenyl, quinolinyl, indolyl, isoquinolinyl, pyridyl, thiazolyl, or pyrimidinyl, said phenyl, quinolinyl, indolyl, isoquinolinyl, pyridyl, thiazolyl, or pyrimidinyl optionally substituted with 1 to 3 groups of $R^a$;
A is —(CH$_2$)$_n$O— or C$_{1-6}$ alkyl, and
$R^1$ is phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl, wherein said phenyl, oxadiazolyl, pyrrolidinyl, pyrazolyl, oxopyrrolidinyl, piperidinyl, thiazolyl, oxazolyl, quinolinyl, isoquinolinyl, pyridyl, or pyrimidinyl is optionally substituted with 1 to 3 groups of $R^b$.

12. A pharmaceutical composition comprising a therapeutically effective amount of a compound of claim 1 or a pharmaceutically acceptable salt thereof, and a pharmaceutically acceptable carrier.

13. A compound which is:
4-(3-Methoxyphenyl)-1-(3-phenylpropyl)-1H-pyrrolo[3, 2-c]pyridine-2-carboxylic acid,
4-(3-Methoxyphenyl)-1-[(2E)-3-phenylprop-2-en-1-yl]-1H-pyrrolo[3,2-c]pyridine-2-carboxylic acid,
3: 4-(3-Methoxyphenyl)-1-[2-oxo-2-(phenylamino) ethyl]-1H-pyrrolo[3,2-c]pyridine-2-carboxylic acid,
1-[2-(Benzylamino)-2-oxoethyl]-4-(3-methoxyphenyl)-1H-pyrrolo[3,2-c]pyridine-2-carboxylic acid,
5: 4-(3-Methoxyphenyl)-1-(3-phenylprop-2-yn-1-yl)-1H-pyrrolo[3,2-c]pyridine-2-carboxylic acid,
4-(3-Ethoxyphenyl)-1-(2-phenoxyethyl)-1H-pyrrolo[3,2-c]pyridine-2-carboxylic acid,
4-(3-ethoxyphenyl)-1-(2-phenylethyl)-1H-pyrrolo[3,2-c]pyridine-2-carboxylic acid,
4-(3-ethoxyphenyl)-1-(3-phenoxypropyl)-1H-pyrrolo[3, 2-c]pyridine-2-carboxylic acid,
1-[2-(4-chlorophenoxy)ethyl]-4-(3-ethoxyphenyl)-1H-pyrrolo[3,2-c]pyridine-2-carboxylic acid,
1-(biphenyl-4-ylmethyl)-4-(3-ethoxyphenyl)-1H-pyrrolo [3,2-c]pyridine-2-carboxylic acid,
1-[2-(benzylsulfonyl)ethyl]-4-(3-ethoxyphenyl)-1H-pyrrolo[3,2-c]pyridine-2-carboxylic acid,
4-(3-ethoxyphenyl)-1-[2-(phenylsulfonyl)ethyl]-1H-pyrrolo[3,2-c]pyridine-2-carboxylic acid,
1-[2-(benzyloxy)ethyl]-4-(3-ethoxyphenyl)-1H-pyrrolo [3,2-c]pyridine-2-carboxylic acid,
4-(3-ethoxyphenyl)-1-(4-phenoxybenzyl)-1H-pyrrolo[3, 2-c]pyridine-2-carboxylic acid,
4-(3-ethoxyphenyl)-1-[4-(phenoxymethyl)benzyl]-1H-pyrrolo[3,2-c]pyridine-2-carboxylic acid,
1-[(5-phenyl-1,2,4-oxadiazol-3-yl)methyl]-4-(quinolin-5-yl)-1H-pyrrolo[3,2-c]pyridine-2-carboxylic acid,
1-[2-(4-chlorophenoxy)ethyl]-4-[3-(propan-2-yloxy)phenyl]-1H-pyrrolo[3,2-c]pyridine-2-carboxylic acid,
1-[2-(4-chlorophenoxy)ethyl]-4-(3-propoxyphenyl)-1H-pyrrolo[3,2-c]pyridine-2-carboxylic acid,
1-[2-(4-chlorophenoxy)ethyl]-4-[3-(2-methylpropoxy) phenyl]-1H-pyrrolo[3,2-c]pyridine-2-carboxylic acid,
4-(3-Ethoxyphenyl)-1-[(1-phenylpyrrolidin-3-yl)methyl]-1H-pyrrolo[3,2-c]pyridine-2-carboxylic acid,
4-(3-Ethoxyphenyl)-1-[(5-phenyl-1H-pyrazol-3-yl)methyl]-1H-pyrrolo[3,2-c]pyridine-2-carboxylic acid,
4-(3-ethoxyphenyl)-1-[(5-oxo-1-phenylpyrrolidin-3-yl) methyl]-1H-pyrrolo[3,2-c]pyridine-2-carboxylic acid,
1-(2-{[1-(phenylcarbonyl)piperidin-4-yl]oxy}ethyl)-4-(3-propoxyphenyl)-1H-pyrrolo[3,2-c]pyridine-2-carboxylic acid,
1-{2-[(1-benzylpiperidin-4-yl)oxy]ethyl}-4-(3-propoxyphenyl)-1H-pyrrolo[3,2-c]pyridine-2-carboxylic acid,
4-(3-ethoxyphenyl)-1-({2-[4-(trifluoromethoxy)phenyl]-1,3-thiazol-4-yl}methyl)-1H-pyrrolo[3,2-c]pyridine-2-carboxylic acid,
4-(3-ethoxyphenyl)-1-({2-[4-(trifluoromethoxy)phenyl]-1,3-oxazol-4-yl}methyl)-1H-pyrrolo[3,2-c]pyridine-2-carboxylic acid,
4-(3-ethoxyphenyl)-1-[2-(quinolin-5-yloxy)ethyl]-1H-pyrrolo[3,2-c]pyridine-2-carboxylic acid,
4-(3-ethoxyphenyl)-1-[2-(isoquinolin-5-yloxy)ethyl]-1H-pyrrolo[3,2-c]pyridine-2-carboxylic acid,
4-(3-ethoxyphenyl)-1-[2-(isoquinolin-8-yloxy)ethyl]-1H-pyrrolo[3,2-c]pyridine-2-carboxylic acid,
4-(3-ethoxyphenyl)-1-{2-[4-(trifluoromethoxy)phenoxy] ethyl}-1H-pyrrolo[3,2-c]pyridine-2-carboxylic acid,
1-[2-(2,4-dichlorophenoxy)ethyl]-4-(3-ethoxyphenyl)-1H-pyrrolo[3,2-c]pyridine-2-carboxylic acid,
1-[2-(3,4-dichlorophenoxy)ethyl]-4-(3-ethoxyphenyl)-1H-pyrrolo[3,2-c]pyridine-2-carboxylic acid,
1-[2-(4-cyanophenoxy)ethyl]-4-(3-ethoxyphenyl)-1H-pyrrolo[3,2-c]pyridine-2-carboxylic acid,
4-(3-ethoxyphenyl)-1-{2-[4-(methylsulfonyl)phenoxy] ethyl}-1H-pyrrolo[3,2-c]pyridine-2-carboxylic acid,
4-(3-ethoxyphenyl)-1-{2-[4-(trifluoromethyl)phenoxy] ethyl}-1H-pyrrolo[3,2-c]pyridine-2-carboxylic acid,
4-(3-Ethoxyphenyl)-1-(2-{[6-(trifluoromethyl)pyridin-3-yl]oxy}ethyl)-1H-pyrrolo[3,2-c]pyridine-2-carboxylic acid,
1-{2-[(5-chloropyridin-2-yl)oxy]ethyl}-4-(3-ethoxyphenyl)-1H-pyrrolo[3,2-c]pyridine-2-carboxylic acid,
4-(3-ethoxyphenyl)-1-{2-[4-(2,2,2-trifluoroethoxy)phenoxy]ethyl}-1H-pyrrolo[3,2-c]pyridine-2-carboxylic acid, 4-(3-ethoxyphenyl)-1-[2-(4-phenoxyphenoxy)ethyl]-1H-pyrrolo[3,2-c]pyridine-2-carboxylic acid, 4-(3-ethoxyphenyl)-1-(2-{[2-(trifluoromethyl)pyrimidin-5-yl]oxy}ethyl)-1H-pyrrolo[3,2-c]pyridine-2-carboxylic acid, 4-(3-ethoxyphenyl)-1-(2-{[1-methyl-3-(trifluoromethyl)-1H-pyrazol-5-yl]oxy}ethyl)-1H-pyrrolo[3,2-c]pyridine-2-carboxylic acid, 1-[2-(4-benzylphenoxy)ethyl]-4-(3-ethoxyphenyl)-1H-pyrrolo[3,2-c]pyridine-2-carboxylic acid, 4-(3-ethoxyphenyl)-1-{2-[4-(phenylamino)phenoxy]ethyl}-1H-pyrrolo[3,2-c]pyridine-2-carboxylic acid, 4-(3-ethoxyphenyl)-1-{2-[4-(tetrahydro-2h-pyran-4-yloxy)phenoxy]ethyl}-1H-pyrrolo[3,2-c]pyridine-2-carboxylic acid, 4-(3-ethoxyphenyl)-1-{2-[4-(tetrahydrofuran-3-yloxy)phenoxy]ethyl}-1H-pyrrolo[3,2-c]pyridine-2-carboxylic acid, 4-(3-ethoxyphenyl)-1-{2-[4-(trifluoromethoxy)phenoxy]ethyl}-1H-pyrrolo[3,2-c]pyridine, 4-[(3-Methoxyphenyl)amino]-1-[(5-phenyl-1,2,4-oxadiazol-3-yl)methyl]-1H-pyrrolo[3,2-c]pyridine-2-carboxylic acid, 1-[(5-Phenyl-1,2,4-oxadiazol-3-yl)methyl]-4-(quinolin-8-yl)-1H-pyrrolo[3,2-c]pyridine-2-carboxylic acid, 4-(isoquinolin-5-yl)-1-[(5-phenyl-1,2,4-oxadiazol-3-yl)methyl]-1H-pyrrolo[3,2-c]pyridine-2-carboxylic acid, 4-(1-methyl-1H-indol-4-yl)-1-[(5-phenyl-1,2,4-oxadiazol-3-yl)methyl]-1H-pyrrolo[3,2-c]pyridine-2-carboxylic acid, 4-(Isoquinolin-4-yl)-1-[(5-phenyl-1,2,4-oxadiazol-3-yl)methyl]-1H-pyrrolo[3,2-c]pyridine-2-carboxylic acid, 1-[2-(4-Chlorophenoxy)ethyl]-4-(2-ethoxypyridin-4-yl)-1H-pyrrolo[3,2-c]pyridine-2-carboxylic acid, 4-(2-Ethoxy-1,3-thiazol-4-yl)-1-{2-[4-(trifluoromethoxy)phenoxy]ethyl}-1H-pyrrolo[3,2-c]pyridine-2-carboxylic acid, 4-[2-(propylamino)pyridin-4-yl]-1-{2-[4-(trifluoromethoxy)phenoxy]ethyl}-1H-pyrrolo[3,2-c]pyridine-2-carboxylic acid, 4-[2-(propylamino)-1,3-thiazol-5-yl]-1-{2-[4-(trifluoromethoxy)phenoxy]ethyl}-1H-pyrrolo[3,2-c]pyridine-2-carboxylic acid, 4-[2-(propylamino)pyrimidin-4-yl]-1-{2-[4-(trifluoromethoxy)phenoxy]ethyl}-1H-pyrrolo[3,2-c]pyridine-2-carboxylic acid, 4-{2-[(2-Hydroxyethyl)amino]pyridin-4-yl}-1-{2-[4-(trifluoromethoxy)phenoxy]ethyl}-1H-pyrrolo[3,2-c]pyridine-2-carboxylic acid, 4-(3-Ethoxyphenyl)-1-(2-{[4-(2,2,2-trifluoroethoxy)phenyl]amino}ethyl)-1H-pyrrolo[3,2-c]pyridine-2-carboxylic acid, 4-[2-(3-Methylpyrrolidin-1-yl)-1,3-thiazol-5-yl]-1-{2-[4-(trifluoromethoxy)phenoxy]ethyl}-1H-pyrrolo[3,2-c]pyridine-2-carboxylic acid, 1-[2-(4-Tert-butoxyphenoxy)ethyl]-4-(3-ethoxyphenyl)-1H-pyrrolo[3,2-c]pyridine-2-carboxylic acid, 4-(isoquinolin-5-yl)-1-{2-[4-(trifluoromethoxy)phenoxy]ethyl}-1H-pyrrolo[3,2-c]pyridine-2-carboxylic acid, 4-(quinolin-5-yl)-1-{2-[4-(trifluoromethoxy)phenoxy]ethyl}-1H-pyrrolo[3,2-c]pyridine-2-carboxylic acid, 4-(quinolin-4-yl)-1-{2-[4-(trifluoromethoxy)phenoxy]ethyl}-1H-pyrrolo[3,2-c]pyridine-2-carboxylic acid, 4-(isoquinolin-4-yl)-1-{2-[4-(trifluoromethoxy)phenoxy]ethyl}-1H-pyrrolo[3,2-c]pyridine-2-carboxylic acid, 4-(3-Ethoxyphenyl)-1-{2-[4-(pyridin-3-yloxy)phenoxy]ethyl}-1H-pyrrolo[3,2-c]pyridine-2-carboxylic acid, 4-(3-ethoxyphenyl)-1-{2-[4-(pyridin-2-yloxy)phenoxy]ethyl}-1H-pyrrolo[3,2-c]pyridine-2-carboxylic acid, 4-(3-ethoxyphenyl)-1-{2-[4-(pyridin-4-yloxy)phenoxy]ethyl}-1H-pyrrolo[3,2-c]pyridine-2-carboxylic acid, 4-(3-ethoxyphenyl)-1-{2-[4-(pyrimidin-2-yloxy)phenoxy]ethyl}-1H-pyrrolo[3,2-c]pyridine-2-carboxylic acid, 4-(3-ethoxyphenyl)-1-{2-[4-(pyrimidin-5-yloxy)phenoxy]ethyl}-1H-pyrrolo[3,2-c]pyridine-2-carboxylic acid, 4-(3-ethoxyphenyl)-1-{2-[4-(pyrazin-2-yloxy)phenoxy]ethyl}-1H-pyrrolo[3,2-c]pyridine-2-carboxylic acid, 4-(3-ethoxyphenyl)-1-{2-[4-(1,3-thiazol-2-yloxy)phenoxy]ethyl}-1H-pyrrolo[3,2-c]pyridine-2-carboxylic acid, and 1-{2-[4-(Trifluoromethoxy)phenoxy]ethyl}-1H-pyrrolo[3,2-c]pyridine-2-carboxylic acid, or a pharmaceutically acceptable salt thereof.

14. A compound according to claim 13 which is:

4-[2-(propylamino)pyrimidin-4-yl]-1-{2-[4-(trifluoromethoxy)phenoxy]ethyl}-1H-pyrrolo[3,2-c]pyridine-2-carboxylic acid, 4-[2-(propylamino)pyridin-4-yl]-1-{2-[4-(trifluoromethoxy)phenoxy]ethyl}-1H-pyrrolo[3,2-c]pyridine-2-carboxylic acid, 1-[2-(4-Tert-butoxyphenoxy)ethyl]-4-(3-ethoxyphenyl)-1H-pyrrolo[3,2-c]pyridine-2-carboxylic acid, 4-(isoquinolin-5-yl)-1-{2-[4-(trifluoromethoxy)phenoxy]ethyl}-1H-pyrrolo[3,2-c]pyridine-2-carboxylic acid, 4-(quinolin-5-yl)-1-{2-[4-(trifluoromethoxy)phenoxy]ethyl}-1H-pyrrolo[3,2-c]pyridine-2-carboxylic acid, 4-(quinolin-4-yl)-1-{2-[4-(trifluoromethoxy)phenoxy]ethyl}-1H-pyrrolo[3,2-c]pyridine-2-carboxylic acid, 4-(isoquinolin-4-yl)-1-{2-[4-(trifluoromethoxy)phenoxy]ethyl}-1H-pyrrolo[3,2-c]pyridine-2-carboxylic acid, 4-(3-Ethoxyphenyl)-1-{2-[4-(trifluoromethoxy)phenoxy]ethyl}-1H-pyrrolo[3,2-c]pyridine-2-carboxylic acid, 4-(3-ethoxyphenyl)-1-[2-(4-phenoxyphenoxy)ethyl]-1H-pyrrolo[3,2-c]pyridine-2-carboxylic acid, and 1-[2-(4-benzylphenoxy)ethyl]-4-(3-ethoxyphenyl)-1H-pyrrolo[3,2-c]pyridine-2-carboxylic acid, or a pharmaceutically acceptable salt thereof.

* * * * *